(12) United States Patent
Ebetino et al.

(10) Patent No.: US 12,285,489 B2
(45) Date of Patent: Apr. 29, 2025

(54) BONE TARGETED ANTIMICROBIAL OXAZOLIDINONE RELATED COMPOUNDS, FORMULATIONS THEREOF, AND USES THEREOF

(71) Applicants: Frank Hallock Ebetino, Venice, FL (US); Shuting Sun, Temple City, CA (US); Charles E. McKenna, Pacific Palisades, CA (US); Keivan Sadrerafi, Pasadena, CA (US); Philip Cherian, Pasadena, CA (US)

(72) Inventors: Frank Hallock Ebetino, Venice, FL (US); Shuting Sun, Temple City, CA (US); Charles E. McKenna, Pacific Palisades, CA (US); Keivan Sadrerafi, Pasadena, CA (US); Philip Cherian, Pasadena, CA (US)

( * ) Notice: Subject to any disclaimer, the term of this patent is extended or adjusted under 35 U.S.C. 154(b) by 825 days.

(21) Appl. No.: 17/255,446

(22) PCT Filed: Jun. 25, 2019

(86) PCT No.: PCT/US2019/039018
§ 371 (c)(1),
(2) Date: Dec. 23, 2020

(87) PCT Pub. No.: WO2020/005964
PCT Pub. Date: Jan. 2, 2020

(65) Prior Publication Data
US 2021/0369849 A1 Dec. 2, 2021

Related U.S. Application Data

(60) Provisional application No. 62/690,053, filed on Jun. 26, 2018.

(51) Int. Cl.
| | |
|---|---|
| A61K 31/541 | (2006.01) |
| A61K 9/00 | (2006.01) |
| A61K 31/422 | (2006.01) |
| A61K 31/4439 | (2006.01) |
| A61K 31/496 | (2006.01) |
| A61K 31/5377 | (2006.01) |
| A61K 47/54 | (2017.01) |
| A61L 27/36 | (2006.01) |
| A61L 27/54 | (2006.01) |

(52) U.S. Cl.
CPC .......... *A61K 47/548* (2017.08); *A61K 9/0024* (2013.01); *A61K 31/422* (2013.01); *A61K 31/4439* (2013.01); *A61K 31/496* (2013.01); *A61K 31/5377* (2013.01); *A61K 31/541* (2013.01); *A61K 47/542* (2017.08); *A61L 27/3608* (2013.01); *A61L 27/54* (2013.01); *A61L 2300/216* (2013.01); *A61L 2300/404* (2013.01); *A61L 2430/02* (2013.01)

(58) Field of Classification Search
CPC .................................................... A61K 47/548
See application file for complete search history.

(56) References Cited

U.S. PATENT DOCUMENTS

| | | | |
|---|---|---|---|
| 2008/0287396 A1 | 11/2008 | Delorme et al. | |
| 2016/0095932 A1 | 4/2016 | Karpeisky et al. | |

FOREIGN PATENT DOCUMENTS

| | | |
|---|---|---|
| JP | 2008-536911 A | 9/2008 |
| WO | 2007/138381 A2 | 12/2007 |
| WO | 2017/210611 A1 | 12/2017 |

OTHER PUBLICATIONS

Japanese Office Action for Patent Application No. 2021-521740, dated Jul. 11, 2023, pp. 1-6.
Extended European Search Report for Application No. 19824932.8, dated Mar. 7, 2022, pp. 1-9.
International Search Report & Written Opinion for WO2020/005964 (PCT/US2019/039018), dated Oct. 28, 2019, pp. 1-4.
International Preliminary Report on Patentability for WO2020/005964 (PCT/US2019/039018), dated Dec. 29, 2020, pp. 1-8.
Giger Elisabeth Vet al: "Biomedical applications of bisphosphonates", Journal of Controlled Release, Elsevier, Amsterdam, NL, vol. 167, No. 2, Feb. 8, 2013 (Feb. 8, 2013), pp. 175-188.
Karen Joy Shaw et al: "The oxazolidinones: past, present, and future: The oxazolidinones: past, present, and future", Annals of the New York Academy of Sciences, vol. 1241, No. 1, Dec. 1, 2011 (Dec. 1, 2011), pp. 48-70.
Chinese Office Action for Patent Application No. 2019800495895, dated Feb. 27, 2024, pp. 1-22 (Translation Included).
The Application and Research Progress of New Anti-MRSA drugs, Lai Chong-fa et al., World Notes on Antibiotics, vol. 38, No. 4, pp. 166-172 and 178 Jul. 31, 2017.

*Primary Examiner* — Paul V Ward
(74) *Attorney, Agent, or Firm* — Thomas | Horstemeyer, LLP

(57) ABSTRACT

Described herein are bisphosphonate oxazolidinone compounds, and conjugates and pharmaceutical formulations thereof, that can include a bisphosphonate and an oxazolidinone (or an oxazolidinone antimicrobial or antibiotic agent, substituent or derivative thereof), where the oxazolidinone can be releasably coupled to the bisphosphonate. Also provided herein are methods of making and methods of using the bisphosphonate oxazolidinone compounds, conjugates and pharmaceutical formulations thereof. Also provided herein are methods of use of the compounds, conjugates and formulations for treating a bone disease or for use in preparing a formulation for the treatment a bone disease.

21 Claims, 32 Drawing Sheets

Risedronate  Zoledronate

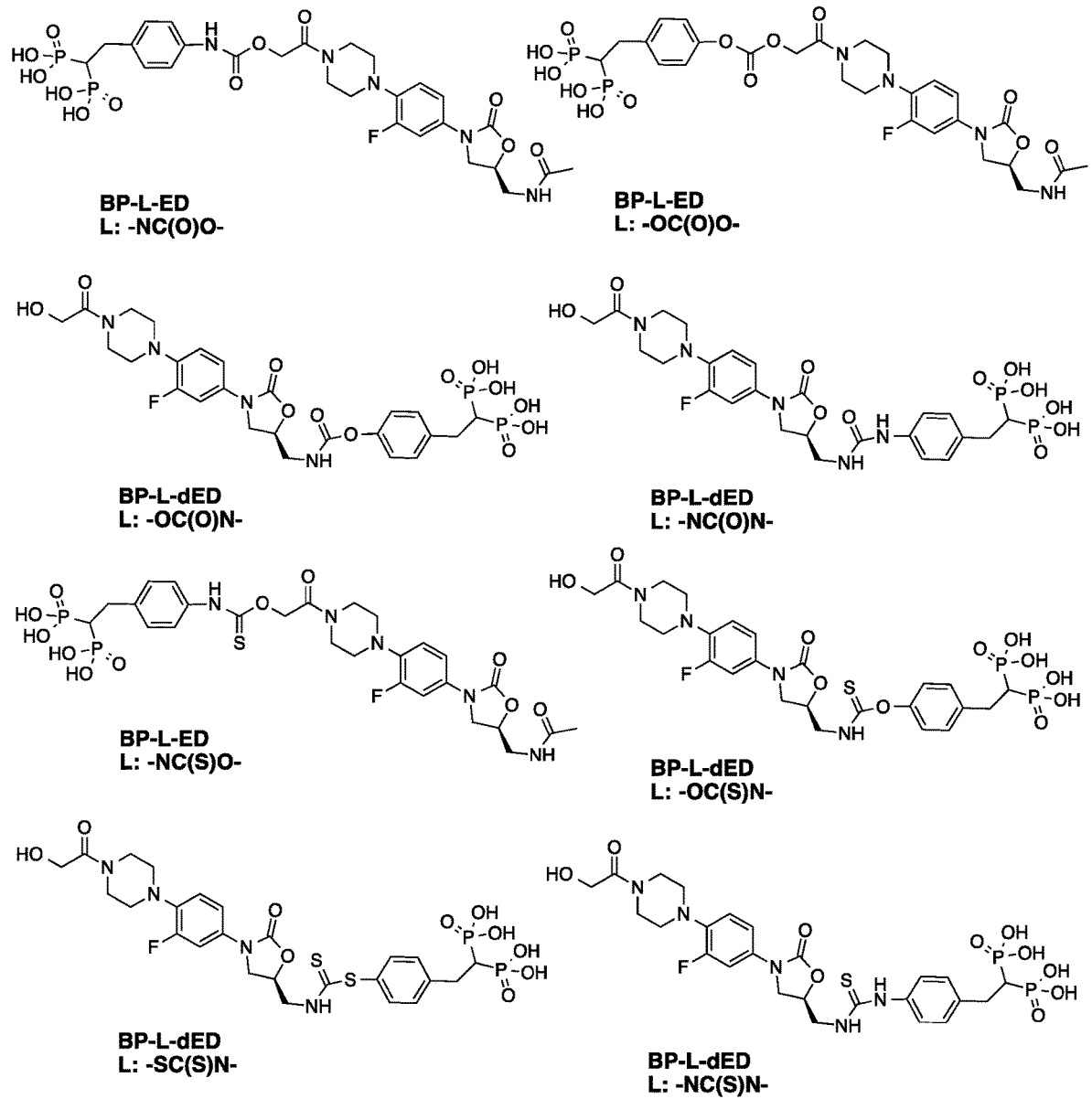
FIG. 6 cont'd (1)

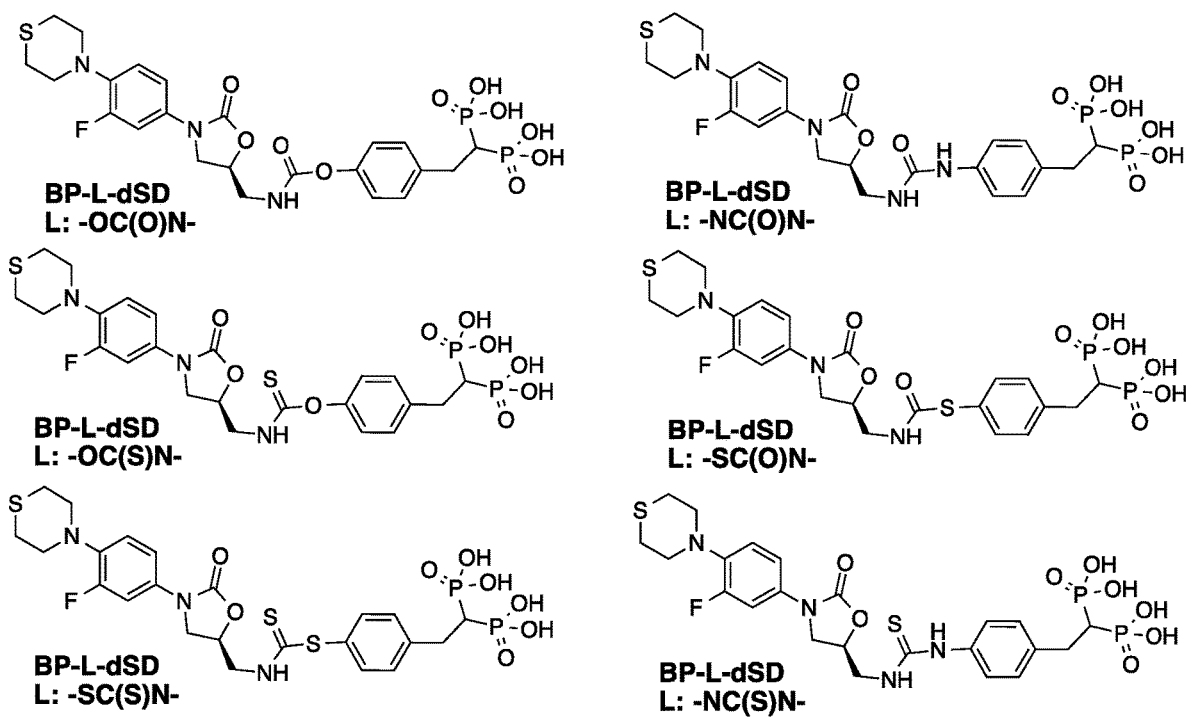
FIG. 6 cont'd (2)

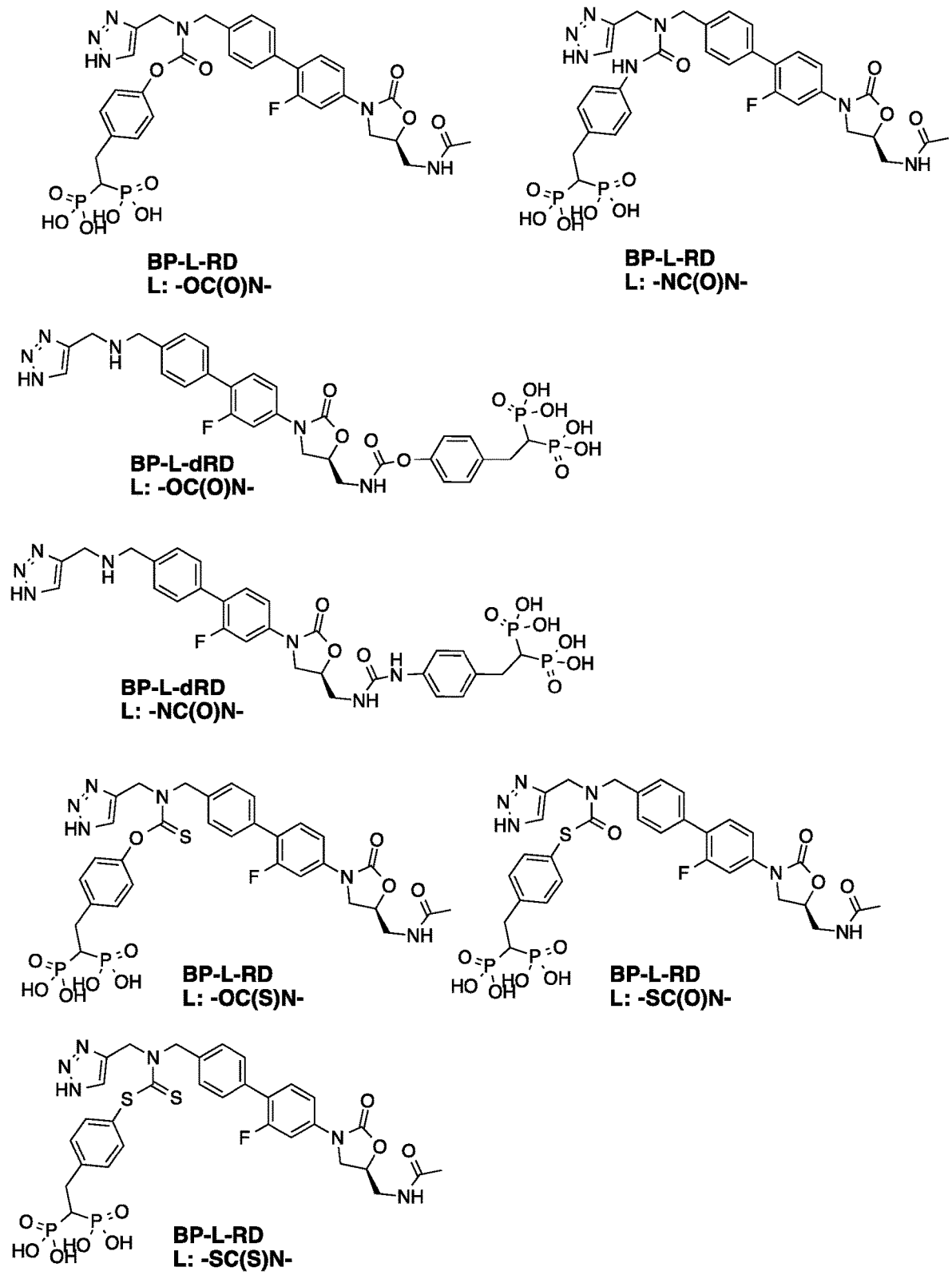
FIG. 6 cont'd (3)

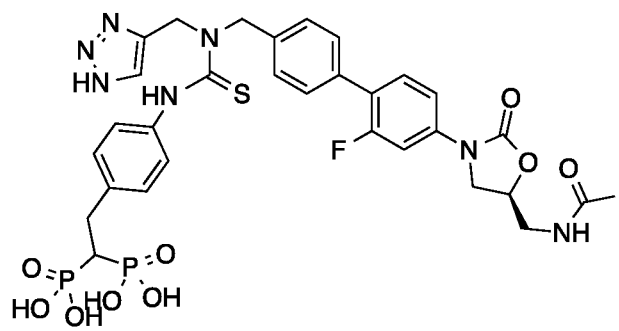
BP-L-RD
L: -NC(S)N-
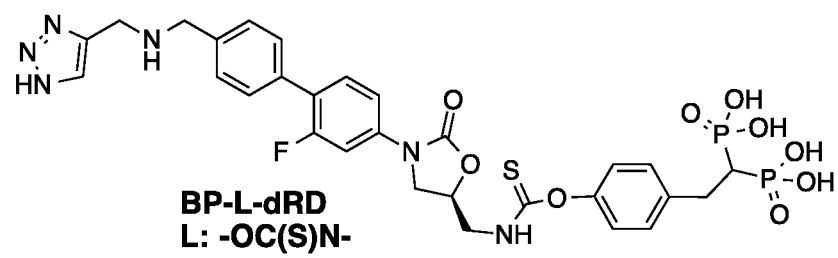
BP-L-dRD
L: -OC(S)N-
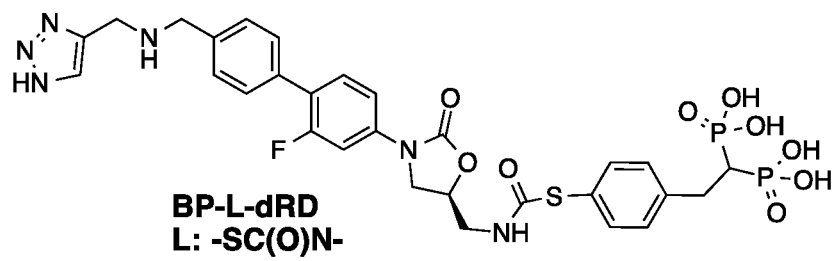
BP-L-dRD
L: -SC(O)N-
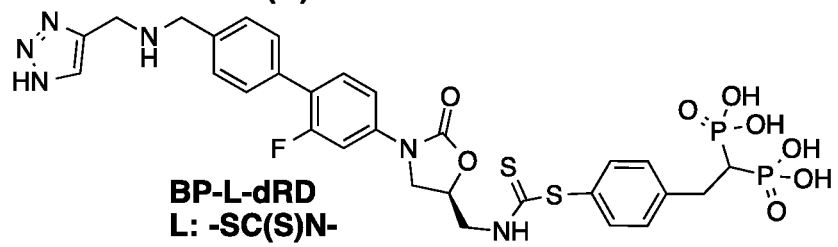
BP-L-dRD
L: -SC(S)N-
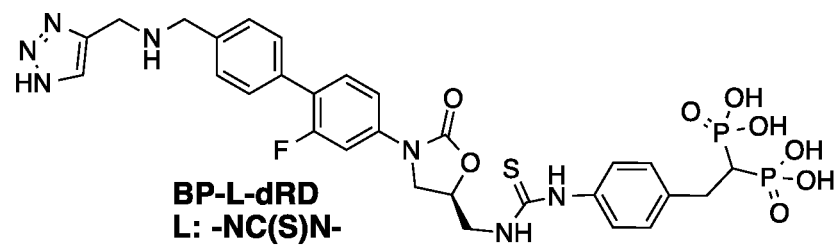
BP-L-dRD
L: -NC(S)N-
FIG. 6 cont'd (4)

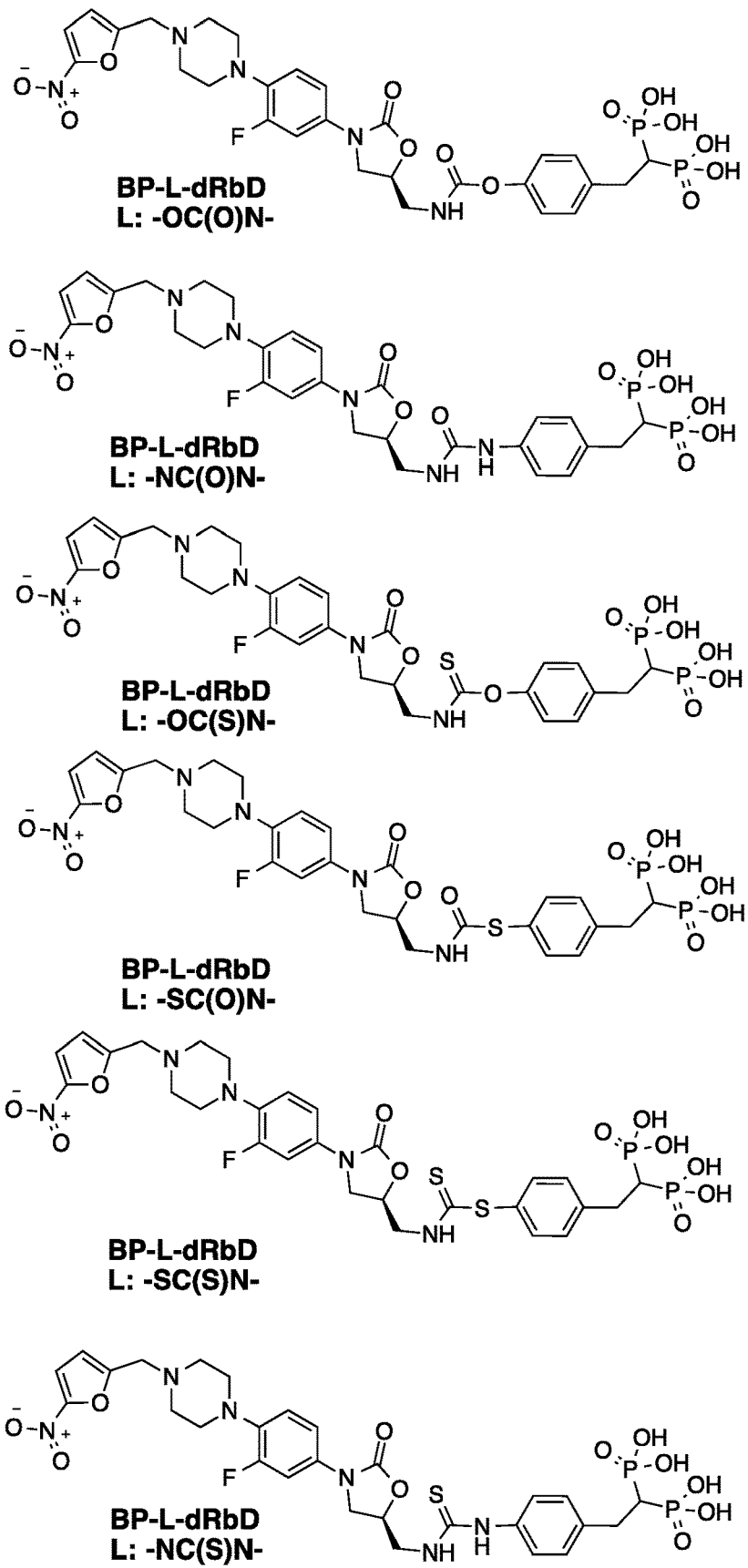
FIG. 6 cont'd (5)

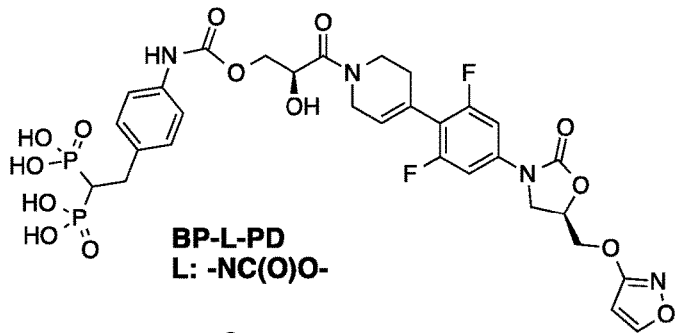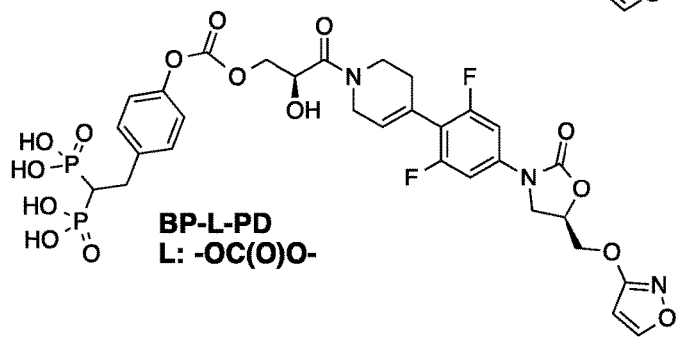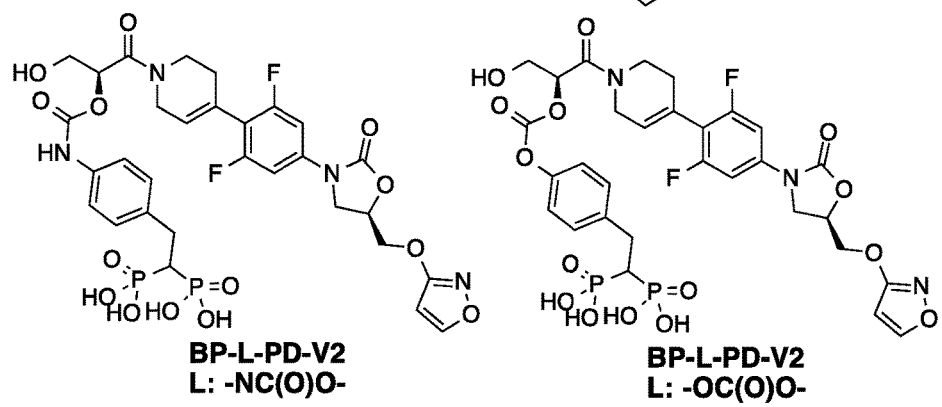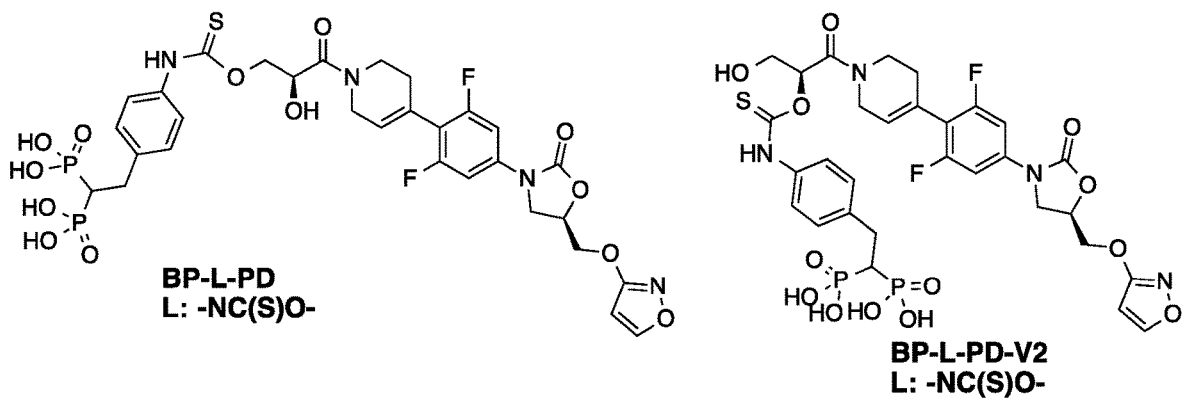
FIG. 6 cont'd (6)

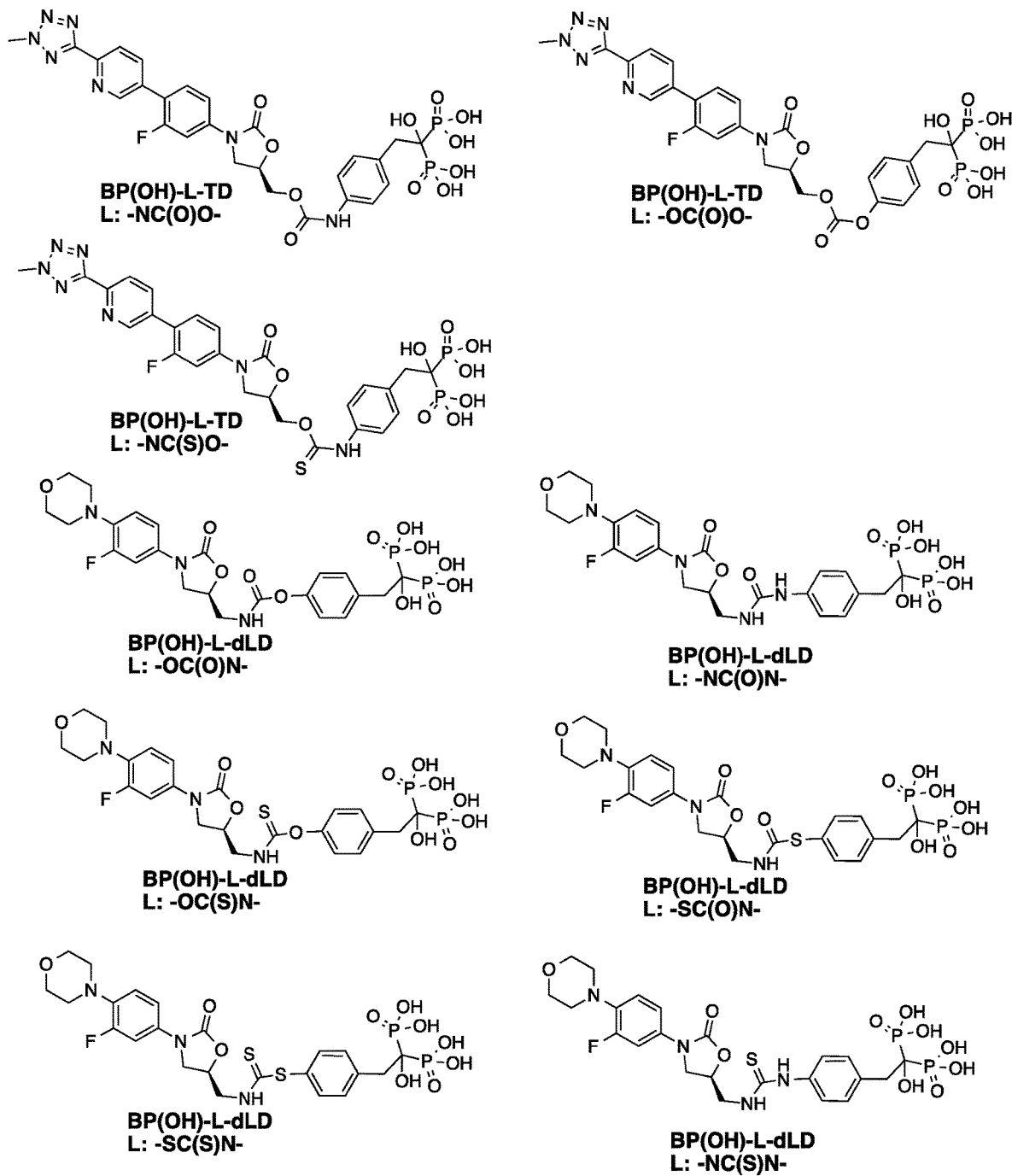
FIG. 6 cont'd (7)

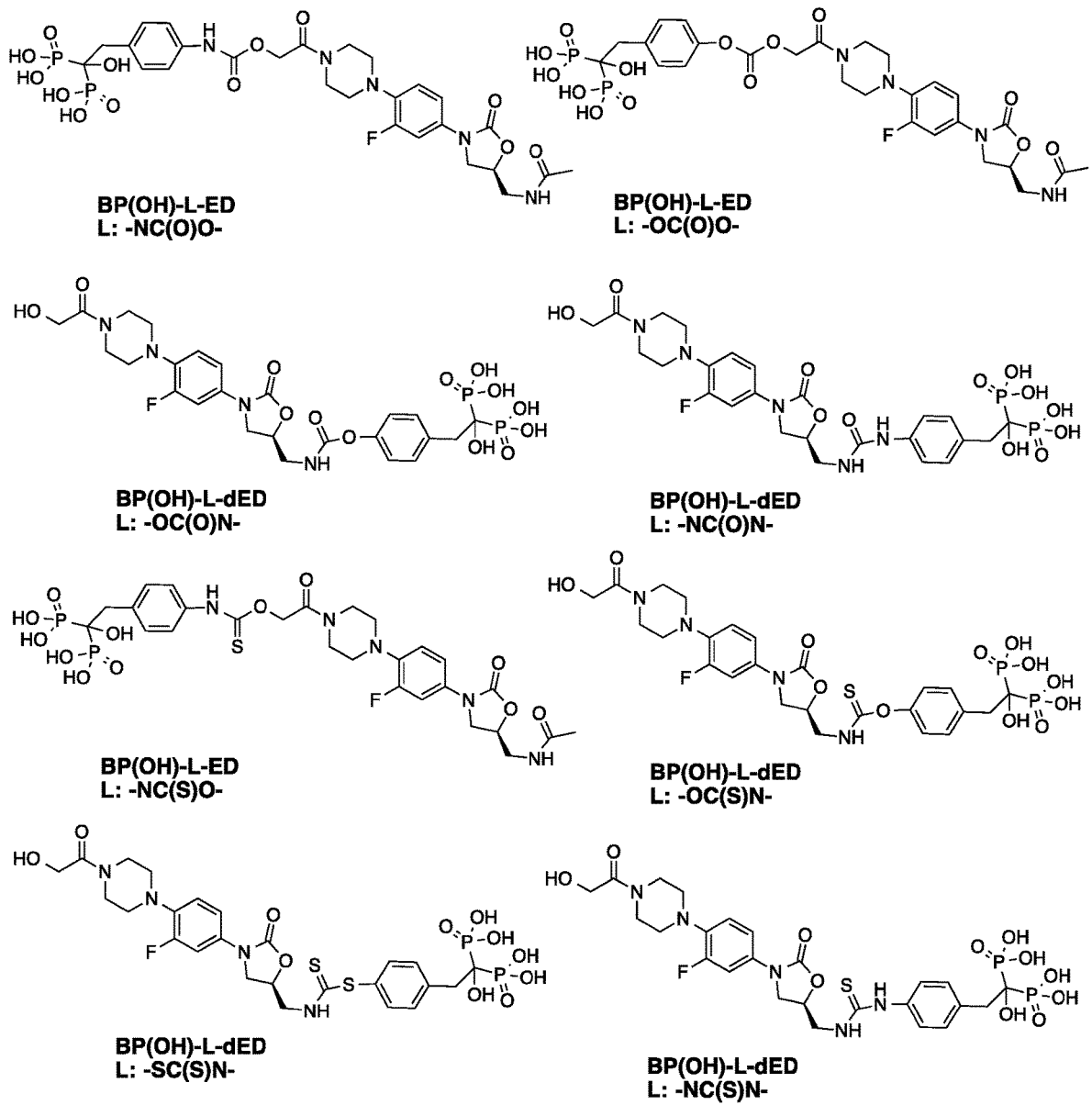
FIG. 6 cont'd (8)

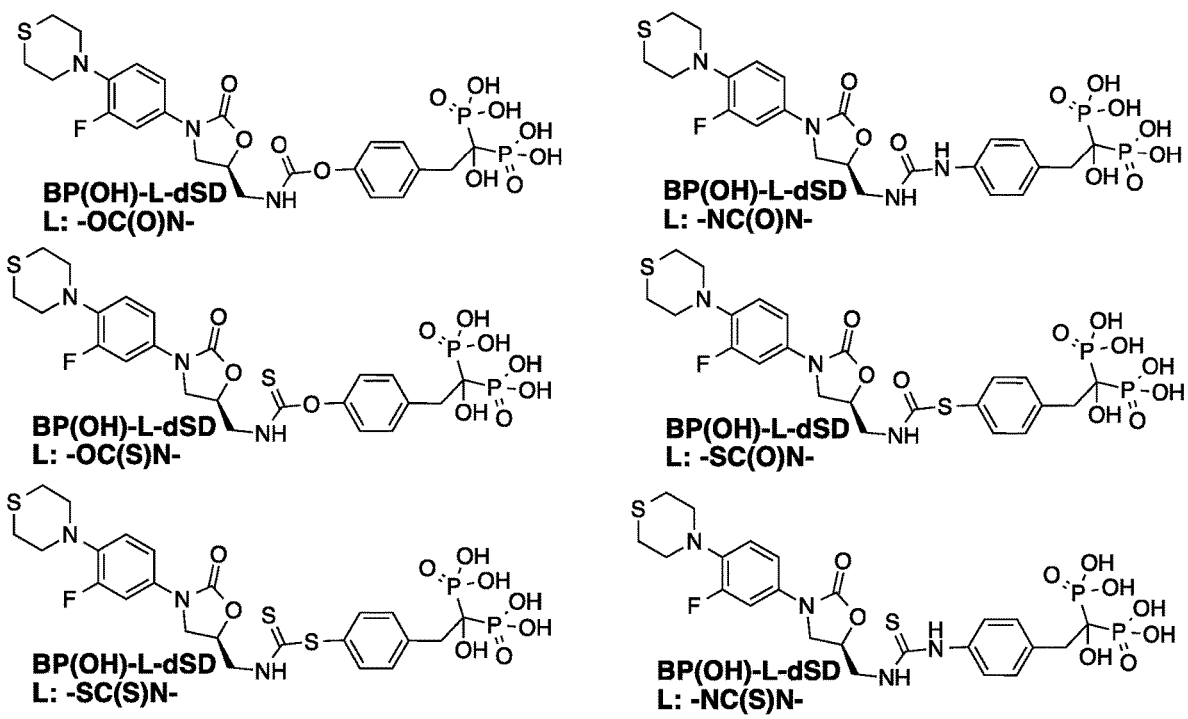
FIG. 6 cont'd (9)

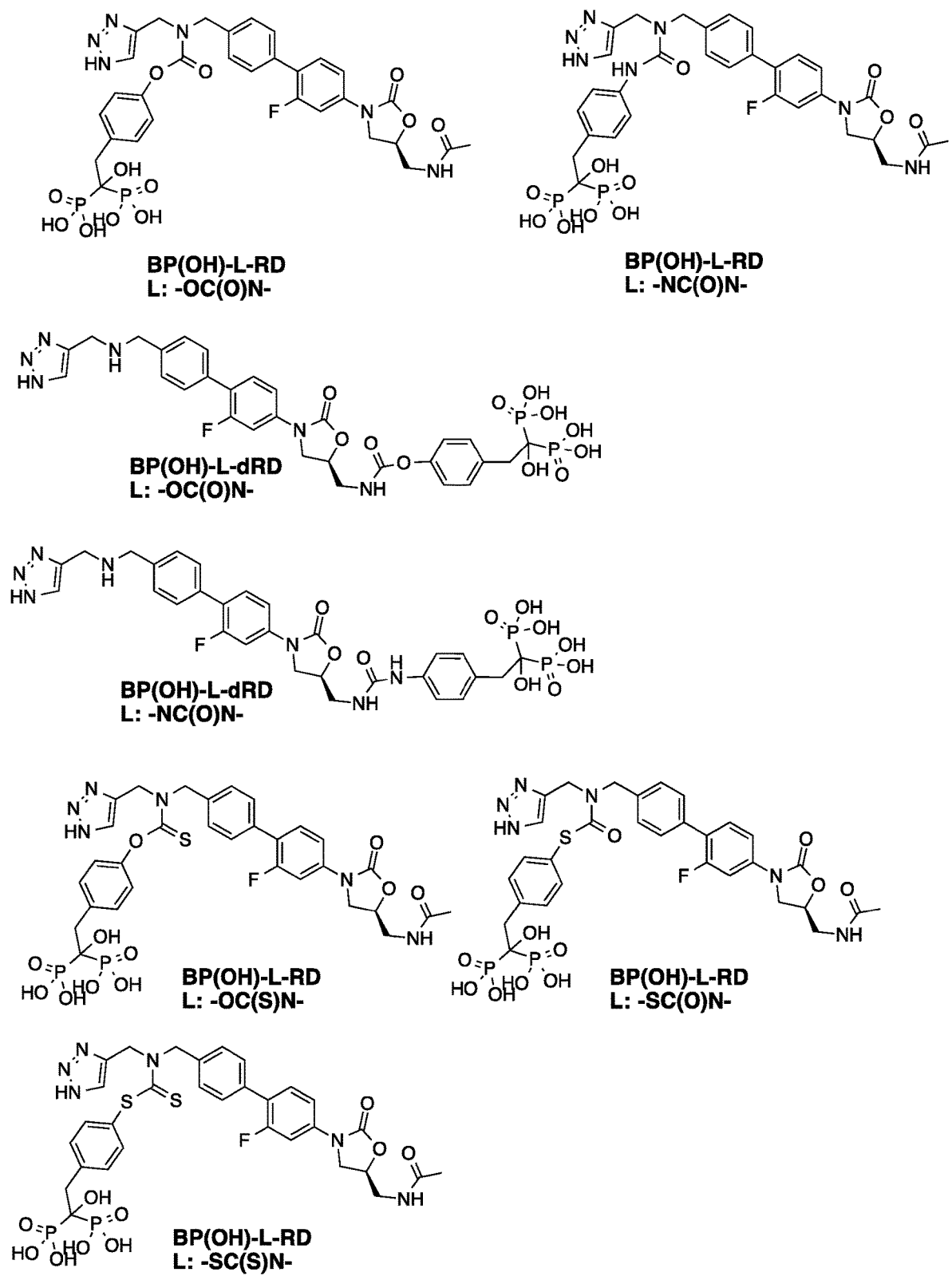
FIG. 6 cont'd (10)

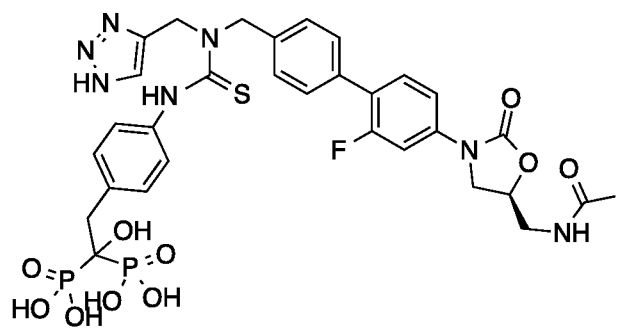
BP(OH)-L-RD
L: -NC(S)N-
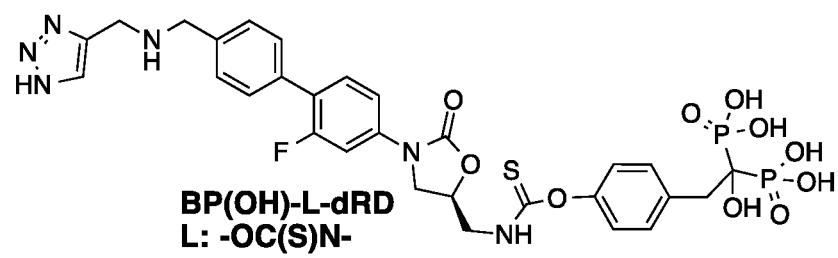
BP(OH)-L-dRD
L: -OC(S)N-
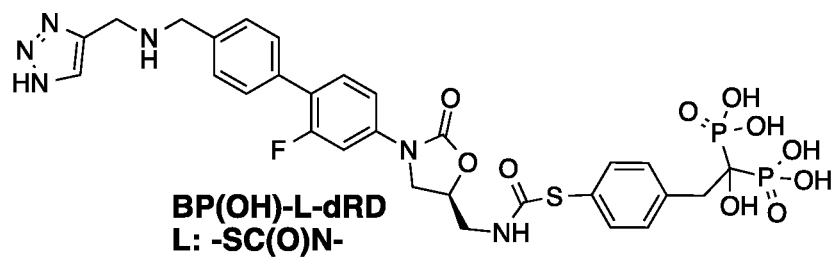
BP(OH)-L-dRD
L: -SC(O)N-
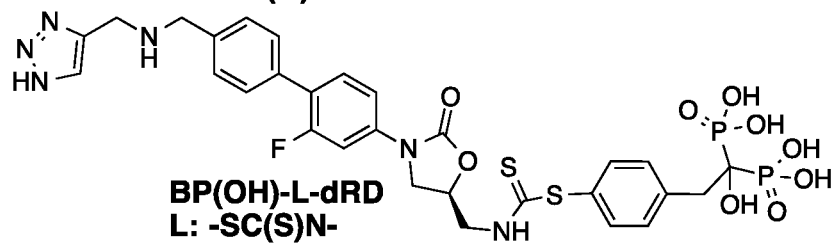
BP(OH)-L-dRD
L: -SC(S)N-
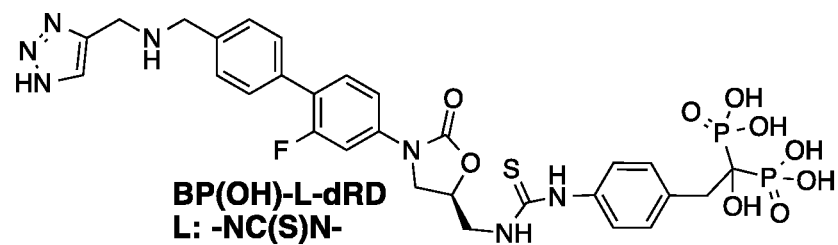
BP(OH)-L-dRD
L: -NC(S)N-
FIG. 6 cont'd (11)

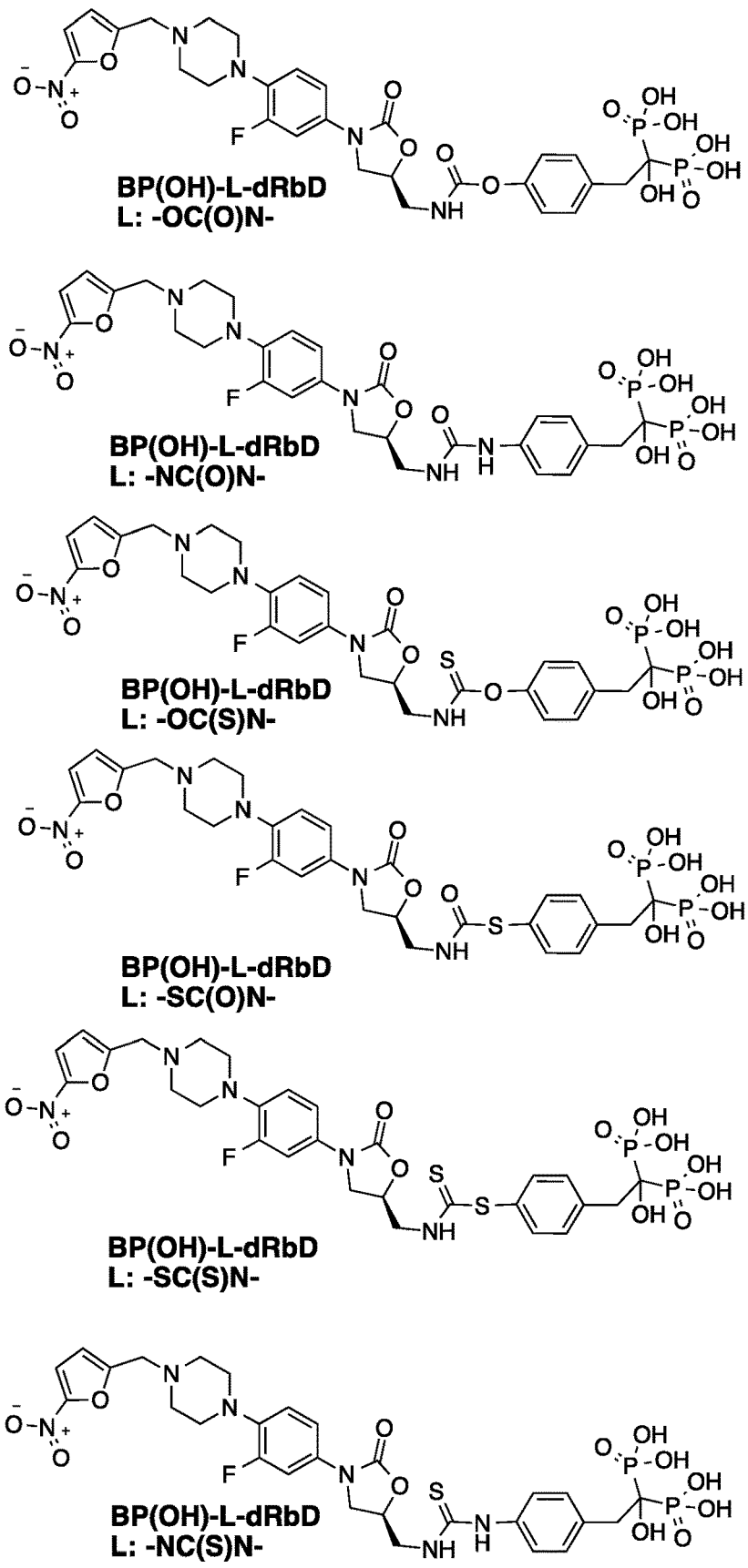
FIG. 6 cont'd (12)

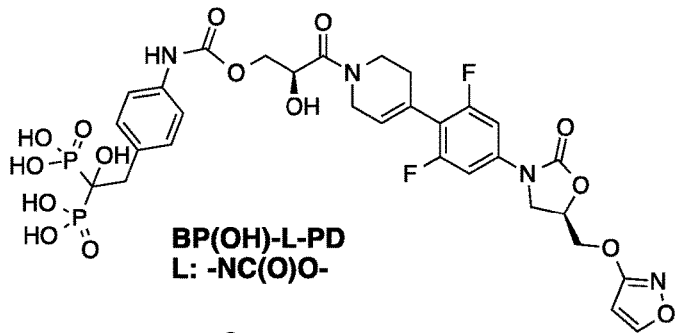
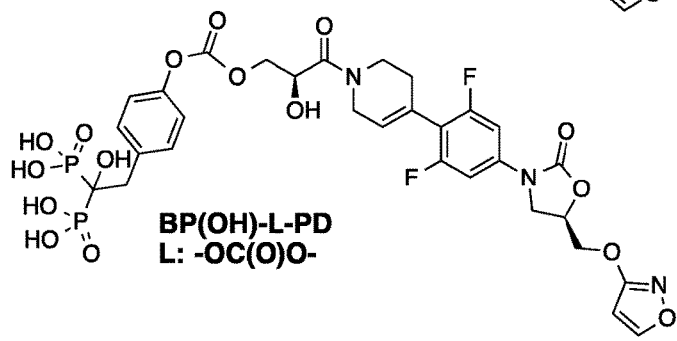
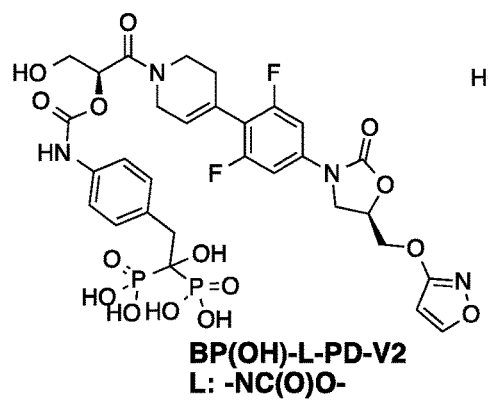
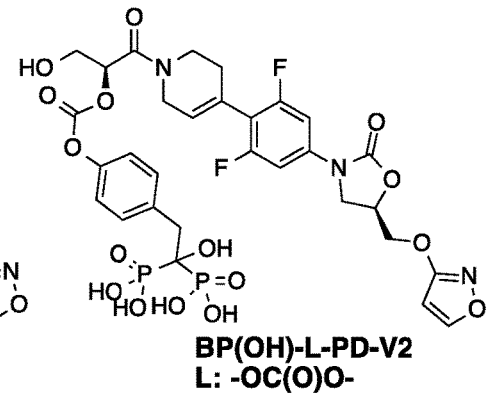
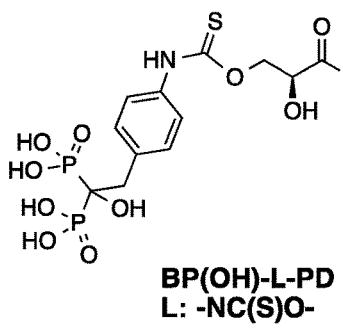
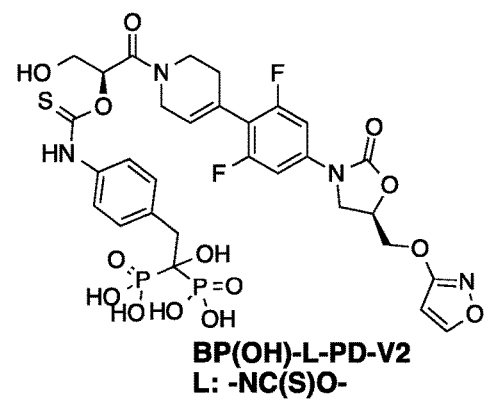
FIG. 6 cont'd (13)

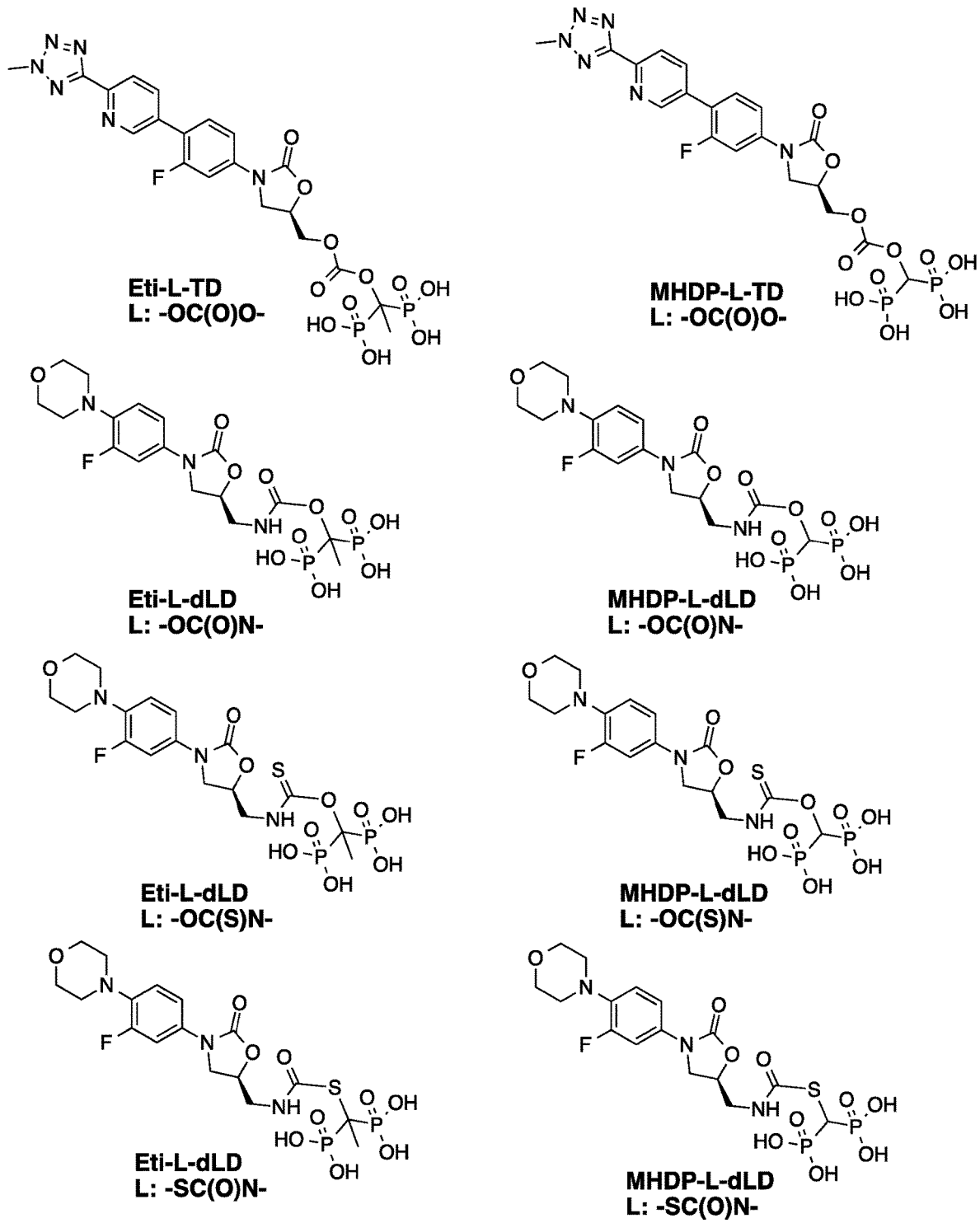
FIG. 6 cont'd (14)

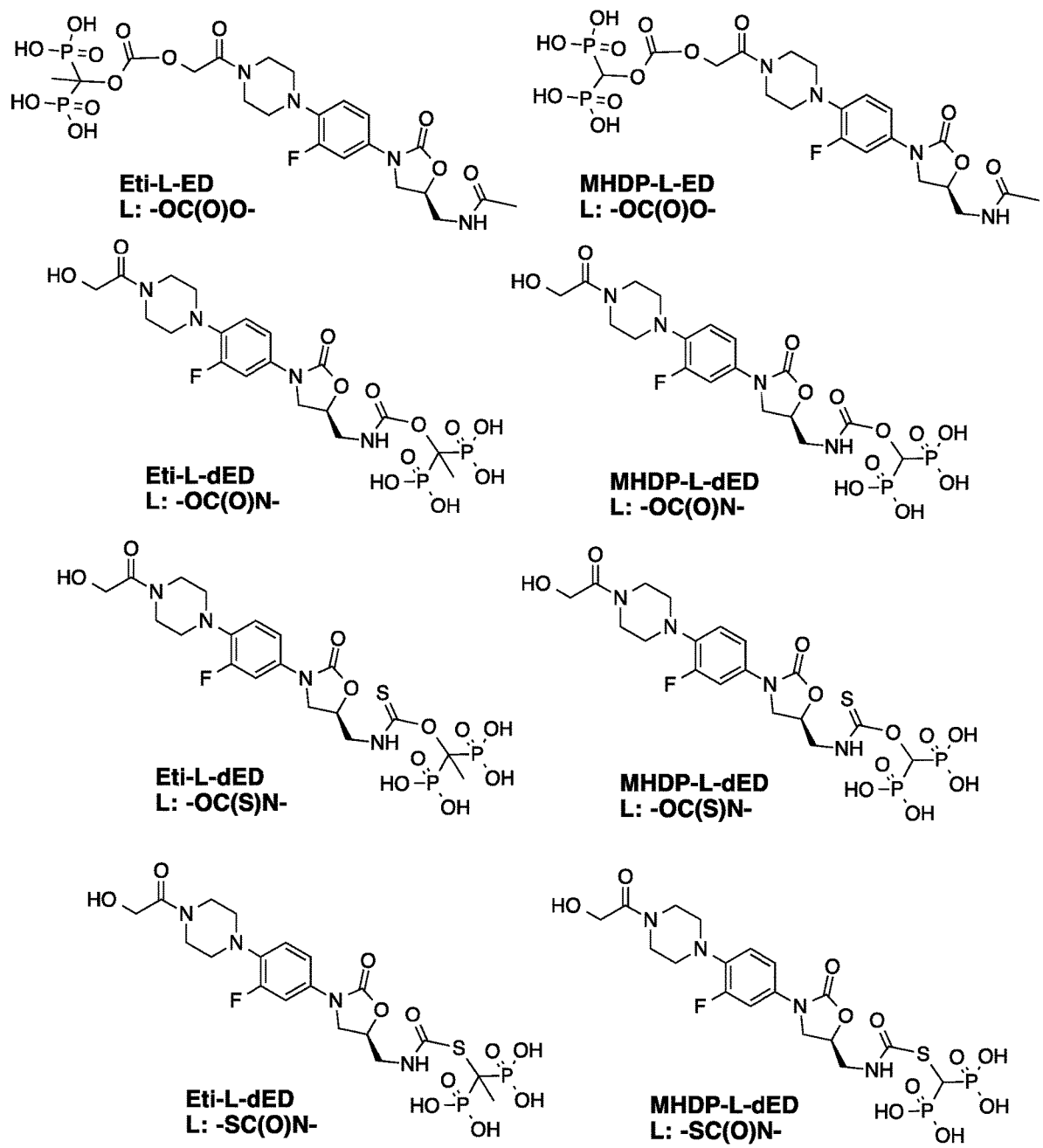
FIG. 6 cont'd (15)

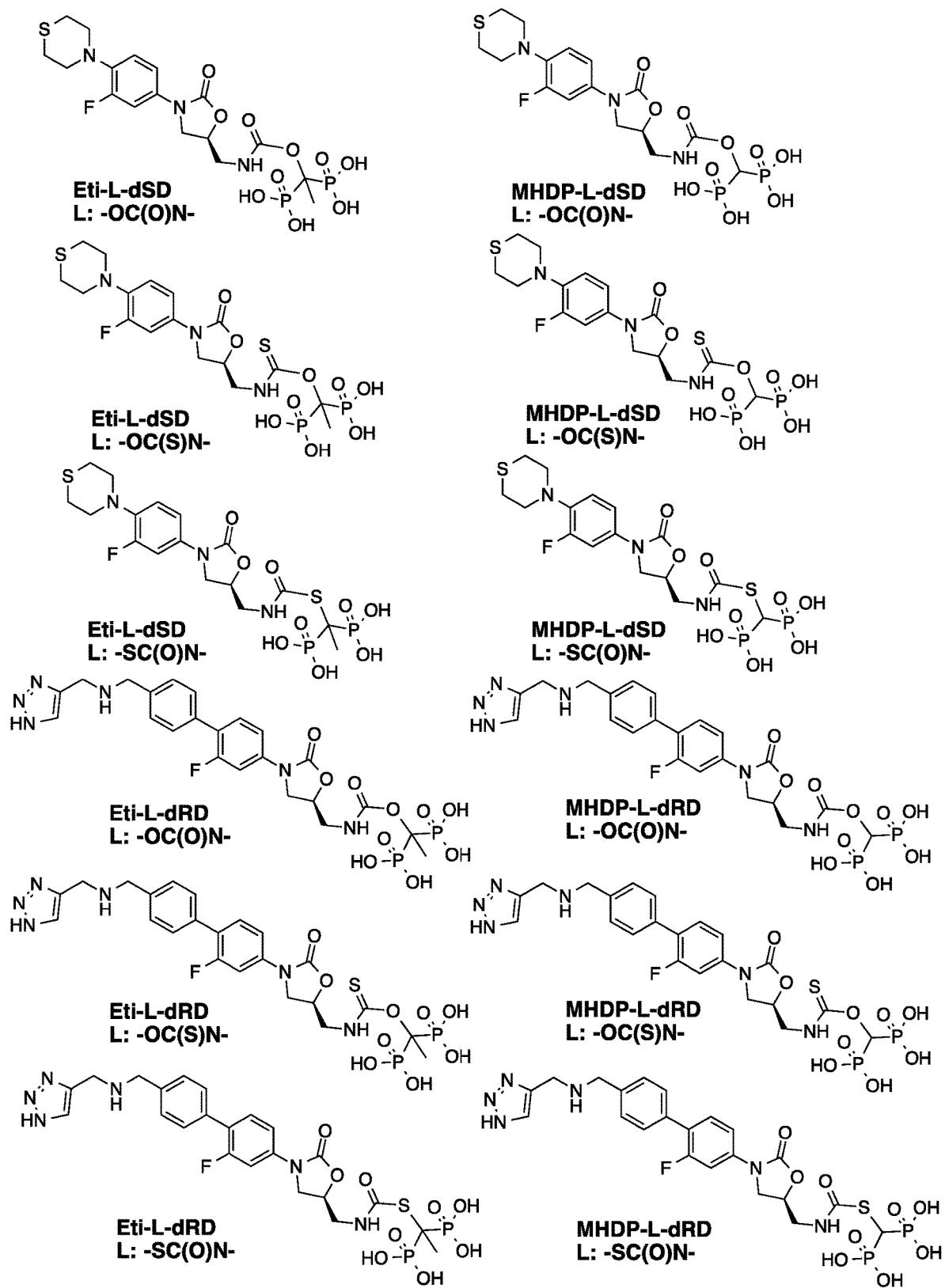
FIG. 6 cont'd (16)

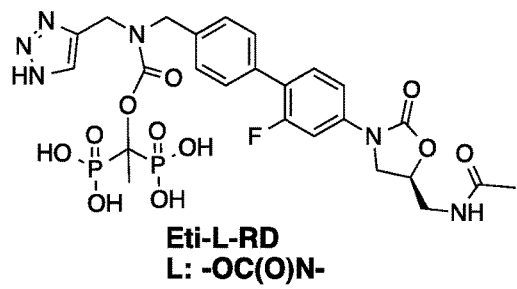
Eti-L-RD
L: -OC(O)N-
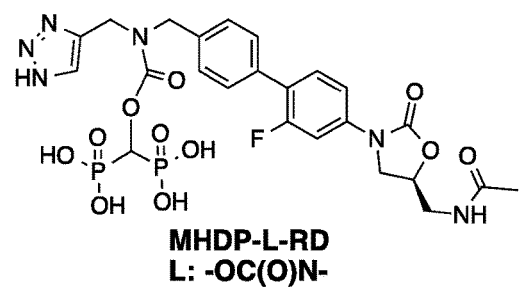
MHDP-L-RD
L: -OC(O)N-
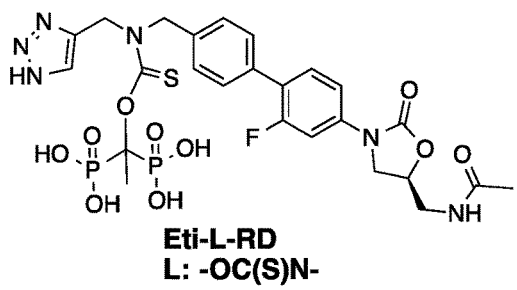
Eti-L-RD
L: -OC(S)N-
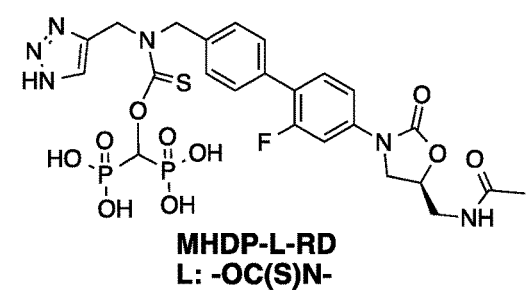
MHDP-L-RD
L: -OC(S)N-
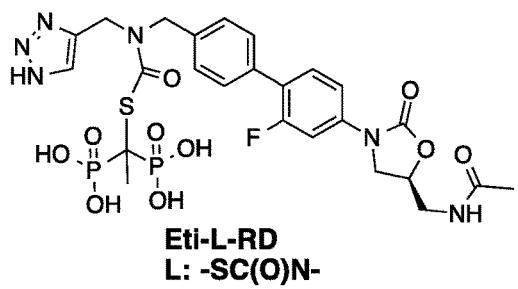
Eti-L-RD
L: -SC(O)N-
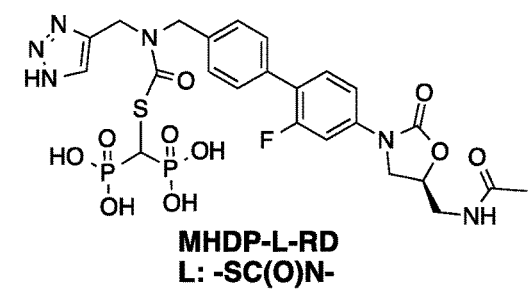
MHDP-L-RD
L: -SC(O)N-
FIG. 6 cont'd (17)

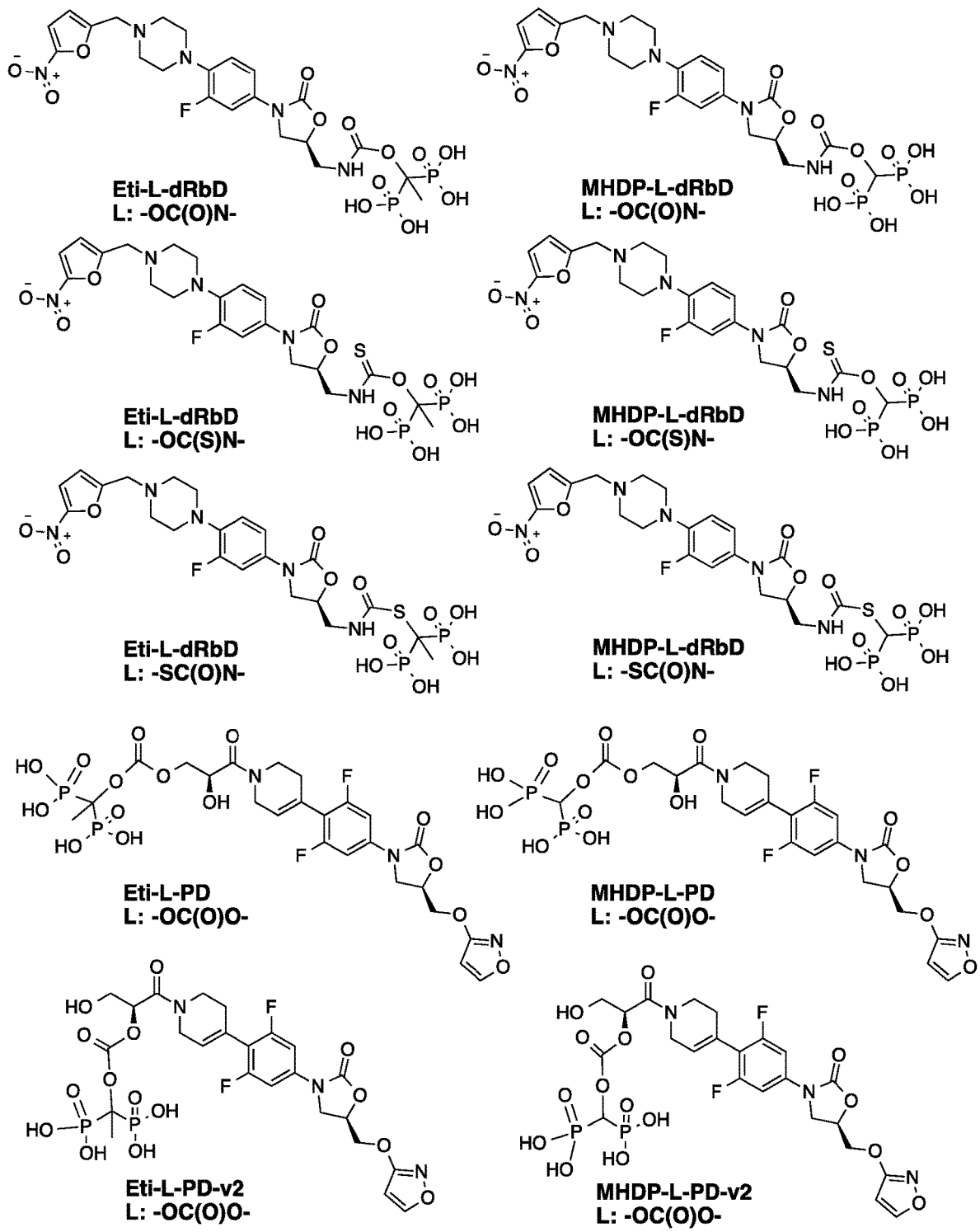
FIG. 6 cont'd (18)

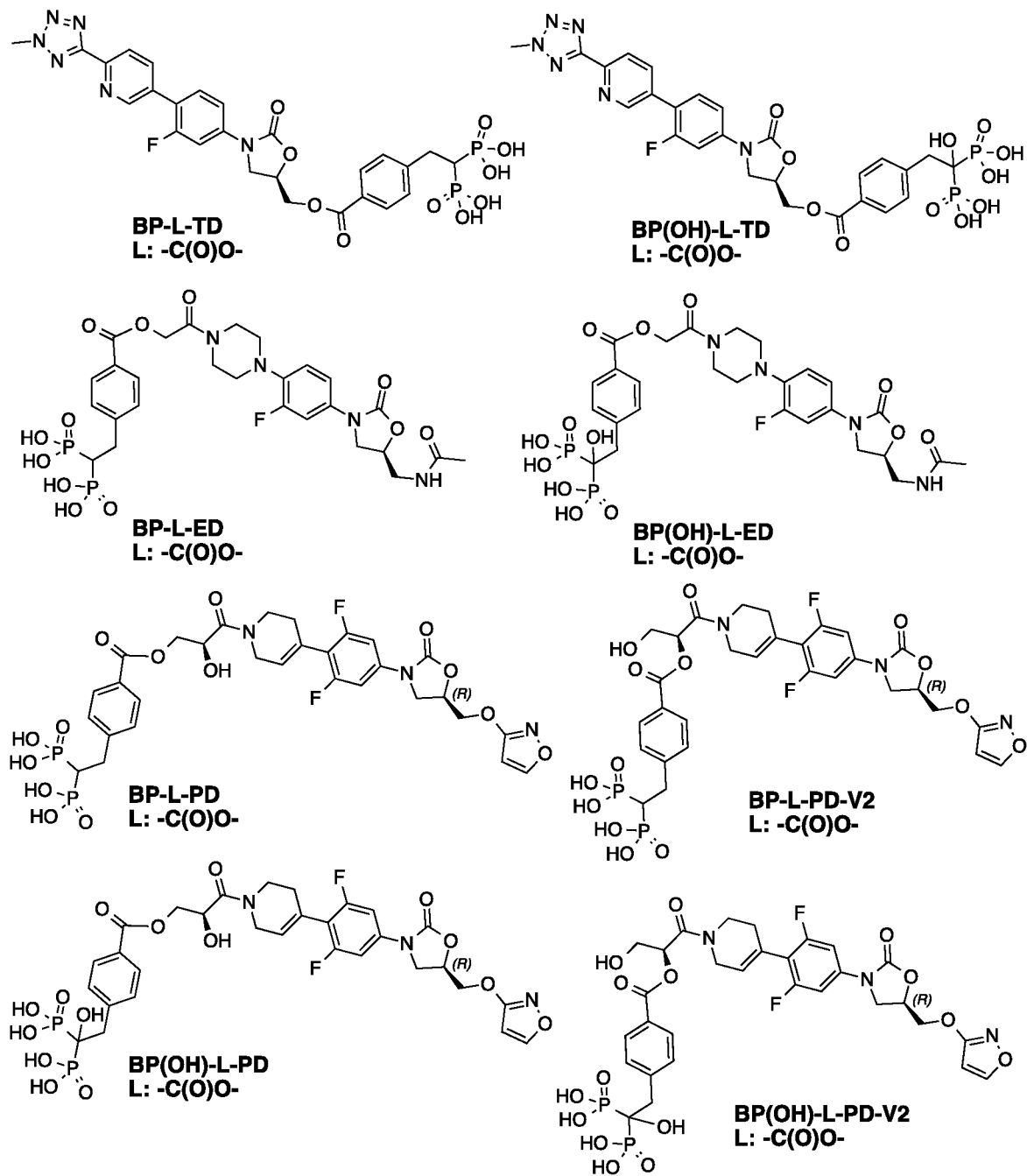
FIG. 6 cont'd (19)

BONE TARGETED ANTIMICROBIAL OXAZOLIDINONE RELATED COMPOUNDS, FORMULATIONS THEREOF, AND USES THEREOF

CROSS-REFERENCE TO RELATED APPLICATIONS

This application is the National Stage of International Application No. PCT/US2019/039018, filed Jun. 25, 2019, which claims priority to US 62/690,053, filed Jun. 26, 2018, which are entirely incorporated herein by reference.

STATEMENT REGARDING FEDERALLY SPONSORED RESEARCH OR DEVELOPMENT

This invention was made with government support under grant number 1R43AI125060-01 awarded by the NIH. The U.S. government has certain rights in the invention.

BACKGROUND

Bone and joint infections affect millions of adults and children worldwide. The overall incidence in the United States is 3-6 million persons, with specific populations having different risks. For diabetics, the annual incidence of foot ulcers is about 1 in 30, with underlying osteomyelitis in up to two-thirds of the cases. In children, recently reported annual incidence ranges from $\frac{1}{4000}$ to $\frac{1}{15000}$. However, in the Pediatric Health Information System (PHIS) database of administrative data from U.S. pediatric hospitals, we found 10,245 (0.5%) discharges with a diagnosis of osteomyelitis among 2,247,889 in a 5-year period from 2009-2013, for a rough annual incidence of approximately $\frac{1}{1100}$ hospitalizations.

A number of Gram-positive and Gram-negative bacteria, as well as fungi and mycobacteria can cause bone and joint infections. By far the most common organism implicated in bone and joint infections is *Staphylococcus aureus*, both methicillin-susceptible (MSSA) and methicillin-resistant (MRSA).

The standard of care for bone and joint infections usually requires systemic administration of antibiotics. For acute infections, intravenous antibiotics are generally prescribed for 2-6 weeks. Prolonged courses of oral antibiotics may follow for chronic infections, or infections associated with retained implanted hardware. Both for acute and chronic infections, these extended courses of therapy can lead to drug-related adverse events in a significant percentage of patients—15% in one estimate for a cohort treated for infections with MSSA. Moreover, it is known that nephrotoxicity with vancomycin, the most common therapy for MRSA infections, occurs in as much as 43% of patients, and increases with duration of therapy.

Persistent bone infections such as jaw osteomyelitis, osteomyelitis at other skeletal sites and osteonecrosis can culminate in significant bone resorption and destruction of bone and hydroxyapatite (HA) mineral. Bone and HA resorption is thought to be induced and mediated not only by bone cells, i.e. osteoclasts, but also microbial biofilm pathogens in combination with host inflammatory responses and osteoclastogenic activity. Treatment of infectious bone disease is mainly antimicrobial therapy with or without surgical intervention depending on clinicopathologic factors. Surgery can involve conservative removal of infected bone or more aggressive modalities such as resection.

To overcome the many challenges associated with treating bone infections, it has become common practice by clinicians to use local delivery systems for achieving higher therapeutic antibacterial concentrations in bone. For example, polymethylmethacrylate beads represent the majority of non-biodegradable carrier systems used to deliver antibiotics to orthopedic infections, but they require surgical removal upon completion of drug release. They also tend to release antibiotics in an initial burst pattern that quickly depletes the bulk of the drug from the carrier beads, followed by a slow release at lower concentrations that may not be adequate to control infection and may foster development of resistance. These concerns limit the usefulness of this approach in the majority of bone and joint infections.

Dentistry has used local delivery of antimicrobials to treat infected jawbone associated with conditions like periodontal bone loss, jaw osteomyelitis and osteonecrosis in order to reach high local concentrations of drug, but these modalities are often ineffective without surgical intervention and bone bioavailability of antibiotic is poor. Antibiotic-impregnated cement, used primarily at the time of first debridement of an infected implant to improve control of the infection, is not generally used in the treatment of bone and joint infections of native bone without implanted hardware. Concerns about prolonged sub-therapeutic antibiotic concentrations and selection of resistant organisms also apply to cement.

Localized delivery of antimicrobial agents to bone is a significant step forward in treating infectious bone disease, but still has penetration limitations and potential eukaryotic cell cytotoxicity; thus research and the development of more effective and physiologically targeted delivery systems are in high demand. An ideal antibiotic delivery system is one that targets bone tissue without the need for surgical implantation or removal. Such targeting also minimizes systemic doses and exposure of tissues other than bone to antibiotics, therefore reducing the risk of adverse effects or selective pressure facilitating the emergence of resistant organisms. Reduced dosing frequency made possible by achieving prolonged concentrations of the antibiotic at the site of infection is another potential major benefit.

SUMMARY

Provided herein, in various aspects, are BP oxazolidinone (or oxazolidone) antibiotic compounds, conjugates and formulations to address the aforementioned needs. The BP oxazolidinone antibiotic compounds, conjugates and formulations can contain a bisphosphonate (BP) that can be releasably conjugated to an oxazolidinone antibiotic, such as tedizolid. In any one or more embodiments, the BP oxazolidinone conjugate can be administered systemically to selectively deliver an oxazolidinone to the skeleton and in particular, infected bone sites, or locally when combined with bone grafts or bone graft substitutes (i.e. can target bone, bone infections, or other high bone metabolism sites) in a subject. In any one or more embodiments, the BP oxazolidinone compound or conjugate can release the oxazolidinone, in particular an oxazolidinone antibiotic compound, substituent or derivative thereof. Also provided herein are methods of synthesizing BP oxazolidinone compounds, conjugates and methods of treating or preventing osteomyelitis or other bone infections with one or more of the BP oxazolidinone compounds, conjugates and/or formulations provided herein.

In any one or more aspects, the compound or conjugate can be a compound according to the general Formula (1), below.

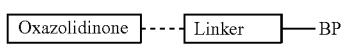

Formula (1)

In any one or more aspects, the compound or conjugate can have the following formula,

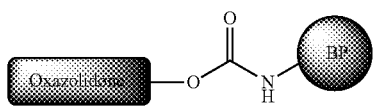

Formula (2)

In a particular embodiment, the compound or conjugate can be a tedizolid analog linked to a bisphosphonate as in either Formula (3) or (4) below.

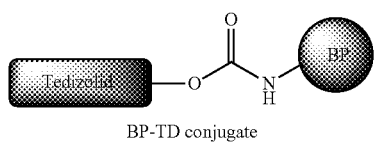

Formula (3)

BP-TD conjugate

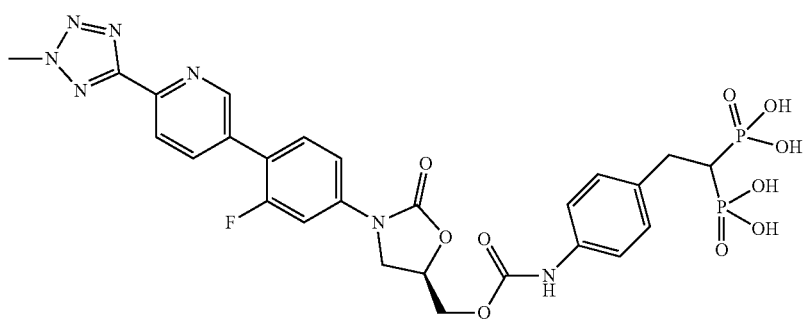

Formula (4)

Also provided herein are pharmaceutical compositions containing a compound or conjugate according to Formula (1), or in particular Formula (2), Formula (3), or Formula (4), and a pharmaceutically acceptable carrier.

Also provided herein are methods of treating a bone infection in a subject in need thereof that can include the step of administering an amount of the compound or conjugate according to Formula (1), or in particular Formula (2), Formula (3) or Formula (4), or a pharmaceutical formulation containing a compound according to Formula (1), or in particular Formula (2), Formula (3) or Formula (4), to a subject in need thereof.

Also provided herein are compounds, conjugates and antimicrobial and antibiotic agents containing a bisphosphonate (BP) and an oxazolidinone compound, wherein the oxazolidinone compound is releasably or reversibly coupled to the bisphosphonate via a linker, as described herein. Preferred releasable linkers are more or less stable in the bloodstream shortly after administration and more or less slowly cleaved in the bone/skeletal compartments of the body to slowly release oxazolidinone antibiotic compounds, substituents or derivatives locally.

In any one or more aspects herein, the BP can be selected from the group of: hydroxyl phenyl alkyl or aryl bisphosphonates, hydroxyl phenyl (or aryl) alkyl hydroxyl bisphosphonates, amino phenyl(or aryl) alkyl bisphosphonates, amino phenyl(or aryl) alkyl hydroxyl bisphosphonates, hydroxyl alkyl bisphosphonates, hydroxyl alkyl hydroxyl bisphosphonates, hydroxyl alkyl phenyl(or aryl) alkyl bisphosphonates, hydroxyl phenyl(or aryl) alkyl hydroxyl bisphosphonates, amino phenyl(or aryl) alkyl bisphosphonates, amino phenyl(or aryl) alkyl hydroxyl bisphosphonates, hydroxyl alkyl bisphosphonates, hydroxyl alkyl hydroxyl bisphosphonates, hydroxypyridyl alkyl bisphosphonates, pyridyl alkyl bisphosphonates, hydroxyl imadazoyl alkyl bisphosphonates, imidazoyl alkyl bisphosphonates, etidronate, pamidronate, neridronate, olpadronate, alendronate, ibandronate, risedronate, zoledronate, minodronate and combinations thereof, wherein all the compounds can be optionally further substituted or are unsubstituted. In particular, the BP can be selected from the group consisting of etidronate, methylene hydroxyl bisphosphonate acid (MHDP), pamidronate, alendronate, risedronate, zolendronate, minodronate, and combinations thereof.

In any one or more aspects herein, the oxazolidinone (or oxazolidone) is an oxazolidinone antimicrobial or antibiotic compound or agent. The oxazolidinone compound can be a compound containing a 2-oxazolidinone (also referred to as 2-oxazolidone). The oxazolidinone compound can be selected from the group of: linezolid, tedizolid, eperizolid, posizolid, radezolid, ranbezolid, sutezolid, and combinations thereof. The oxazolidinone can be, in particular, an antimicrobial or antibiotic substituent (for example, a suitable substituent) or derivative of any of the foregoing.

In some aspects, the BP is etidronate. In some aspects, the oxazolidinone is tedizolid. In other aspects, the oxazolidinone is tedizolid and the BP can be another BP described herein, such as pamidronate, neridronate, olpadronate, alendronate, ibandronate, minodronate, risedronate, zoledronate, hydroxymethylenebisphosphonate, and combinations thereof.

Analogs of the oxazolidinone compound of the present disclosure can have a structure according to Formula (5),

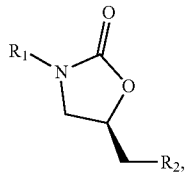

Formula (5)

where $R^1$ can be known components of oxazolidinone antibiotic substituents or oxazolidinone derivative antimicrobial or antibiotic compounds, and can include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups; and where $R^2$ can be substituents including a releasable linker, as described herein, involved in the linkage to a bisphosphonate, as described herein, and can include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

The linker can be a compound that is cleavable, meaning that it reversibly couples the oxazolidinone antimicrobial or antibiotic compound, in particular an oxaxolidinone antimicrobial or antibiotic substituent or derivative thereof, to the BP. As used herein, the term "cleavable" can mean a group that is chemically or biochemically unstable under physiological conditions. In any one or more aspects, the linker can be a carbamate, having a structure or formula (6) below

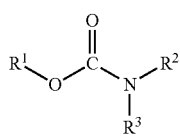

Formula (6)

for coupling an oxazolidinone, $R^1$, to a BP, $R^2$, as described herein, and $R^3$ can be substituted and unsubstituted alkyl, acetyl, benzoyl or other amides, phenyl and substituted phenyl, preferably H.

In any one or more aspects, the linker can be a carbonate, having a structure or formula (7) below

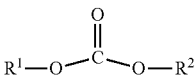

Formula (7)

for coupling an oxazolidinone, $R^1$, to a BP, $R^2$, as described herein.

In any one or more aspects, the linker can be an aryl carbamate linker. The linker can be an O-thioaryl carbamate linker. The linker can be an S-thioaryl carbamate linker. The linker can be a phenyl carbamate linker. The linker can be a thiocarbamate linker. The linker can be an O-thiocarbamate linker. The linker can be an S-thiocarbamate linker. The linker can be an ester linker. The linker can be a dithiocarbamate. The linker can be a urea linker. The linker can be attached to the $R^2$ group of Formula (5) and couple to BP, as described herein, thereto. In any one or more aspects, the linker can be exemplified by any one of Formula (8)-Formula (12) below, wherein: $R^1$ can be an oxazolidinone or an oxazolidinone substituent or derivative and $R^2$ can be a BP, both as described herein; and $R^3$ can be substituted and unsubstituted alkyl, acetyl, benzoyl or other amides, phenyl and substituted phenyl, preferably H.

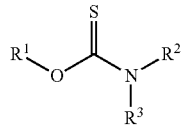

Formula (8)

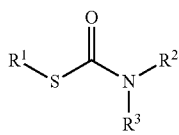

Formula (9)

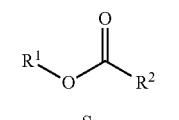

Formula (10)

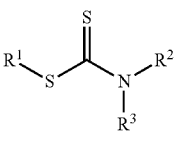

Formula (11)

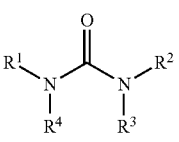

Formula (12)

In any one or more aspects, the alpha position of the methylidenebisphosphonate moiety can be substituted by hydroxy, fluoro, chloro, bromo or iodo. In some aspects, the bisphosphonate can include a para-hydroxyphenylethylidene group or derivative thereof. In some aspects, ethylidenebisphosphonate does not contain an alpha-hydroxy at the alpha position.

In any one or more aspects, the compound or conjugate has a formula according to Formula (1), or more particularly Formula (2), Formula (3), Formula (4), or Formula (5) above.

Also provided herein are pharmaceutical formulations that can contain a bisphosphonate and an oxazolidinone antibiotic compound, wherein the oxazolidinone antibiotic compound is releasably coupled to the bisphosphonate via a linker; and a pharmaceutically acceptable carrier. Preferred releasable linkers are more or less stable in the bloodstream shortly after administration and more or less slowly cleaved in the bone/skeletal compartments of the body to slowly release oxazolidinone antibiotic compounds, substituents or derivatives locally.

In any one or more aspects, the bisphosphonate can be selected from the group of: hydroxyl phenyl alkyl or aryl bisphosphonates, hydroxyl phenyl (or aryl) alkyl hydroxyl bisphosphonates, amino phenyl(or aryl) alkyl bisphosphonates, amino phenyl(or aryl) alkyl hydroxyl bisphosphonates, hydroxyl alkyl bisphosphonates, hydroxyl alkyl hydroxyl bisphosphonates, hydroxyl alkyl phenyl(or aryl) alkyl bisphosphonates, hydroxyl phenyl(or aryl) alkyl hydroxyl bisphosphonates, amino phenyl(or aryl) alkyl bisphosphonates, amino phenyl(or aryl) alkyl hydroxyl bisphosphonates, hydroxyl alkyl bisphosphonates, hydroxyl alkyl hydroxyl bisphosphonates, hydroxypyridyl alkyl bisphosphonates, pyridyl alkyl bisphosphonates, hydroxyl imidazoyl alkyl bisphosphonates, imidazoyl alkyl bisphosphonates, etidronate, pamidronate, neridronate, olpadronate, alendronate, ibandronate, risedronate, zoledronate, minodronate and combinations thereof, wherein all the compounds can be optionally further substituted or are unsubstituted. In particular, the BP can be selected from the group consisting of etidronate, methylene hydroxyl bisphosphonate acid (MHDP), pamidronate, alendronate, risedronate, zolendronate, minodronate, and combinations thereof.

In any one or more aspects herein, the oxazolidinone (or oxazolidone) is an oxazolidinone antimicrobial or antibiotic compound or agent. The oxazolidinone compound can be a compound containing 2-oxazolidinone. The oxazolidinone compound can be selected from the group of: linezolid, tedizolid, eperizolid, posizolid, radezolid, ranbezolid, sutezolid, and combinations thereof. The oxazolidinone can be, in particular, an antimicrobial or antibiotic substituent (for example, a suitable substituent) or derivative of any of the foregoing.

In some aspects, the BP is etidronate. In some aspects, the oxazolidinone is tedizolid. In other aspects, the oxazolidinone is tedizolid and the BP can be another BP described herein, such as pamidronate, neridronate, olpadronate, alendronate, ibandronate, minodronate, risedronate, zoledronate, hydroxymethylenebisphosphonate, and combinations thereof.

Analogs of the oxazolidinone antibiotic compound can have a structure according to Formula (5)

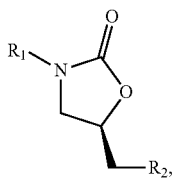

Formula (5)

where $R^1$ can be known components of oxazolidinone antibiotic substituents or oxazolidinone derivative antimicrobial or antibiotic compounds, and can include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups; and where $R^2$ can be substituents including a releasable linker, as describe herein, involved in the linkage to a bisphosphonate, as described herein, and can include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

The linker can be a compound that is cleavable, meaning that it reversibly couples the oxazolidinone antimicrobial compound to the BP. In any one or more aspects, the linker can be a carbamate, having a structure or formula (6) above, for coupling an oxazolidinone, $R^1$, to a BP, $R^2$, as described herein, and $R^3$ can be substituted and unsubstituted alkyl, acetyl, benzoyl or other amides, phenyl and substituted phenyl, preferably H.

In any one or more aspects, the linker can be a carbonate, having a structure or formula (7) above for coupling an oxazolidinone, $R^1$, to a BP, $R^2$, as described herein.

In any one or more aspects, the linker can be a carbamate linker. The linker can be an aryl carbamate linker. The linker can be an O-thioaryl carbamate linker. The linker can be an S-thioaryl carbamate linker. The linker can be a phenyl carbamate linker. The linker can be a thiocarbamate linker. The linker is can be an O-thiocarbamate linker. The linker can be an S-thiocarbamate linker. The linker can be an ester linker. The linker can be a dithiocarbamate. The linker can be a urea linker. The linker can be attached to the $R^2$ group of Formula (5) and couple to a BP, as described herein, thereto. In any one or more aspects, the linker can be exemplified by any one of Formula (8)-Formula (12) above, wherein: $R^1$ can be an oxazolidinone or an oxazolidinone substituent or derivative and $R^2$ can be a BP, both as described herein; and $R^3$ can be substituted and unsubstituted alkyl, acetyl, benzoyl or other amides, phenyl and substituted phenyl, preferably H.

In any one or more aspects, the alpha position of the methylidenebisphosphonate moiety can be substituted by hydroxy, fluoro, chloro, bromo or iodo. In some aspects, the bisphosphonate can include a para-hydroxyphenylethylidene group or a para-hydroxyphenylalkylidene group or derivative thereof. In some aspects, hydroxyethylidenebisphosphonate/hydroxyphenylalkylidene does not contain an alpha-hydroxy at the alpha position.

In some aspects, the formulation can include a compound or conjugate having a formula according to Formula (1), or more particularly Formula (2), Formula (3), Formula (4) or Formula (5) above.

The amount of the compound or conjugate in the pharmaceutical formulation can be an amount effective to kill or inhibit bacteria. The amount of the compound or conjugate in the pharmaceutical formulation can be an amount effective to treat, inhibit, or prevent a bone disease. The amount of the compound or conjugate in the pharmaceutical formulation can be an amount effective to treat, inhibit, or prevent osteomyelitis, osteonecrosis, peri-implantitis, and/or periodontitis. The amount of the compound or conjugate in the pharmaceutical formulation can be an amount effective for prophylaxis treatment of any of the foregoing.

Also provided herein are methods of treating a bone disease, such as a hematogenous or local osteomyelitis including juvenile osteomyelitis and infections related to prosthetic joint replacements or osteonecrosis, in a subject in need thereof that can include the step of administering an amount of a compound as provided herein or pharmaceutical formulation thereof to the subject in need thereof.

Also provided herein are methods of treating peri-implantitis or periodontitis in a subject in need thereof, the method comprising administering an amount of administering an amount of a compound as provided herein or pharmaceutical formulation thereof to the subject in need thereof.

Also provided herein are methods of treating bone infections in diabetic patients including diabetic foot diseases in a subject in need thereof, the method comprising administering an amount of administering an amount of a compound as provided herein or pharmaceutical formulation thereof to the subject in need thereof. A reduction in related amputations, debridement, of limbs and infected skeletal sites will result from these more powerful localized modes of antibiotic therapies.

Also provided herein are bone graft compositions that can include a bone graft material and a compound as described herein or a pharmaceutical formulation thereof, wherein the compound or pharmaceutical formulation thereof is attached to, integrated with, chemisorbed to, or mixed with the bone graft material. The bone graft material can be autograft bone material, allograft bone material, xenograft bone material, a synthetic bone graft material, or any combination thereof.

Also provided herein are methods that can include the step of implanting the bone graft composition as described herein in a subject in need thereof.

Also provided herein are methods of preventing or prophylaxis treatment of biofilm infection at an osseous or implant surgical site, or at a surgical site where bone grafting is performed, where the methods can include the step of administering a compound as described herein to a subject in need thereof.

Also provided herein are methods of preventing or prophylaxis treatment of biofilm infection at an osseous or implant surgical site, or at a surgical site where bone grafting is performed, where the method can include the step of implanting a bone graft composition as described herein to a subject in need thereof.

Further, in an embodiment, a method is provided of preparing a bisphosphonate-antimicrobial agent conjugate thereof, comprising linking a bisphosphonate with an oxazolidinone antimicrobial agent. In any one or more aspects thereof, the antimicrobial agent can comprise an oxazolidinone substituent or derivative or 2-oxazolidinone. The bisphosphonate can have a formula of

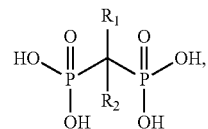

wherein either $R_1$ or $R_2$ contains an alkyl (hydroxy phenyl) group, an alkylhydroxyl group, an alkyl phenylamino group, an alkylamino group, an alkyl (hydroxy heterocyclic) group, or an alkyl aminoheterocyclic group. The bisphosphonate can be methylidene bisphosphonate and the alpha position of the methylidenebisphosphonate moiety is substituted by hydroxy, fluoro, chloro, bromo or iodo. The bisphosphonate can be ethylidene bisphosphonate and the alpha position of the ethylidenebisphosphonate is substituted by hydroxy, fluoro, chloro, bromo or iodo. The antimicrobial agent can contain a primary amine group, or a secondary amine group, or a hydroxyl group. The linking between the bisphosphonate and the antimicrobial agent is reversible in vivo to release the oxazolidinone antimicrobial agent at a targeted site with a therapeutically effective rate and dose. A carbamate linker is used for the linking between the bisphosphonate and the oxazolidinone antimicrobial agent, preferably an aryl carbamate linker. A carbonate linker is used for the linking between the bisphosphonate and the oxazolidinone antimicrobial agent. An ester linker is used for the linking between the bisphosphonate and the oxazolidinone antimicrobial agent. A urea (carbamide) linker is used for the linking tween the bisphosphonate and the oxazolidinone antimicrobial agent. Either an S-thiocarbamate or an O-thiocarbamate linker is used for the linking between the bisphosphonate and the oxazolidinone antimicrobial agent. A dithiocarbamate linker is used for the linking between the bisphosphonate and the oxazolidinone antimicrobial agent. A thio-urea (thiocarbamide) linker is used for the linking between the bisphosphonate and the oxazolidinone antimicrobial agent. The oxazolidinone antimicrobial agent can contain a hydroxymethyl substituent on an oxazolidinone heterocyclic group. The oxazolidinone antimicrobial agent can be tedizolid. The oxazolidinone antimicrobial agent can be linezolid or its deacetyl-analog. The oxazolidinone antimicrobial agent can be eperezolid, sutezolid, radezolid, ranbezolid, their deacetyl-analogs, or posizolid. The bisphosphonate can be 4-aminophenylethylidene bisphosphonate.

In any one or more embodiments herein, a bisphosphonate-antimicrobial agent is provided prepared by any one or more aspects of the aforementioned method.

In any one or more embodiments herein, a bisphosphonate-antimicrobial agent is provided. The bisphosphonate-antimicrobial agent can be a 4-aminophenylethylidene bisphosphonate linked via a carbamate to tedizolid (TD) of the general formula (BP-L-TD), wherein BP is 4-aminophenylethylidene bisphosphonate, L is —NC(O)O—, and TD is tedizolid. The bisphosphonate-antimicrobial agent can consist of 4-hydroxyphenylethylidene bisphosphonate linked via a carbonate to tedizolid (TD) of the general formula (BP-L-TD), wherein BP is 4-hydroxyphenylethylidene bisphosphonate, L is —OC(O)O—, and TD is tedizolid. The bisphosphonate-antimicrobial agent can consist of 4-aminophenylethylidene bisphosphonate linked via a carbamate to tedizolid (TD) of the general formula (BP-L-TD), wherein BP is 4-aminophenylethylidene bisphosphonate, L is —NC(S)O—, and TD is tedizolid. The bisphosphonate-antimicrobial agent can consist of 4-hydroxyphenylethylidene bisphosphonate linked via a carbamate to deacetyl-linezolid (dLD)

of the general formula (BP-L-dLD), wherein BP is 4-hydroxyphenylethylidene bisphosphonate, L is —OC(O)N—, and dLD is deacetyl-linezolid. The bisphosphonate-antimicrobial agent can consist of 4-hydroxyphenylethylidene bisphosphonate linked via a carbamate to deacetyl-linezolid (dLD) of the general formula (BP-L-dLD), wherein BP is 4-hydroxyphenylethylidene bisphosphonate, L is —OC(S)N— or —SC(O)N— or —SC(S)N—, and dLD is deacetyl-linezolid. The bisphosphonate-antimicrobial agent can consist of 4-aminophenylethylidene bisphosphonate linked via a urea to deacetyl-linezolid (dLD) of the general formula (BP-L-dLD), wherein BP is 4-aminophenylethylidene bisphosphonate, L is —NC(O)N— or —NC(S)N—, and dLD is deacetyl-linezolid. The bisphosphonate-antimicrobial agent can consist of 4-hydroxyphenylethylidene bisphosphonate linked via a carbamate to eperezolid (ED) of the general formula (BP-L-ED), wherein BP is 4-hydroxyphenylethylidene bisphosphonate, L is —NC(O)O—, and ED is eperezolid. The bisphosphonate-antimicrobial agent can consist of 4-hydroxyphenylethylidene bisphosphonate linked via a carbamate to eperezolid (ED) of the general formula (BP-L-ED), wherein BP is 4-hydroxyphenylethylidene bisphosphonate, L is —NC(S)O—, and ED is eperezolid. The bisphosphonate-antimicrobial agent can consist of 4-hydroxyphenylethylidene bisphosphonate linked via a carbonate to eperezolid (ED) of the general formula (BP-L-ED), wherein BP is 4-hydroxyphenylethylidene bisphosphonate, L is —OC(O)O—, and ED is eperezolid. The bisphosphonate-antimicrobial agent can consist of 4-hydroxyphenylethylidene bisphosphonate linked via a carbamate to deacetyl-eperezolid (dED) of the general formula (BP-L-dED), wherein BP is 4-hydroxyphenylethylidene bisphosphonate, L is —OC(O)N—, and dED is deacetyl-eperezolid. The bisphosphonate-antimicrobial agent can consist of 4-hydroxyphenylethylidene bisphosphonate linked via a carbamate to deacetyl-eperezolid (dED) of the general formula (BP-L-dED), wherein BP is 4-hydroxyphenylethylidene bisphosphonate, L is —OC(S)N— or —SC(O)N— or —SC(S)N—, and dED is deacetyl-eperezolid. The bisphosphonate-antimicrobial agent can consist of 4-aminophenylethylidene bisphosphonate linked via a urea to deacetyl-eperezolid (dED) of the general formula (BP-L-dED), wherein BP is 4-aminophenylethylidene bisphosphonate, L is —NC(O)N— or —NC(S)N—, and dED is deacetyl-eperezolid. The bisphosphonate-antimicrobial agent can consist of 4-hydroxyphenylethylidene bisphosphonate linked via a carbamate to deacetyl-sutezolid (dSD) of the general formula (BP-L-dSD), wherein BP is 4-hydroxyphenylethylidene bisphosphonate, L is —OC(O)N—, and dSD is deacetyl-sutezolid. The bisphosphonate-antimicrobial agent can consist of 4-hydroxyphenylethylidene bisphosphonate linked via a carbamate to deacetyl-sutezolid (dSD) of the general formula (BP-L-dSD), wherein BP is 4-hydroxyphenylethylidene bisphosphonate, L is —OC(S)N— or —SC(O)N— or —SC(S)N—, and dSD is deacetyl-sutezolid. The bisphosphonate-antimicrobial agent can consist of 4-aminophenylethylidene bisphosphonate linked via a urea to deacetyl-sutezolid (dSD) of the general formula (BP-L-dSD), wherein BP is 4-aminophenylethylidene bisphosphonate, L is —NC(O)N— or —NC(S)N—, and dSD is deacetyl-sutezolid. The bisphosphonate-antimicrobial agent can consist of 4-aminophenylethylidene bisphosphonate linked via a carbamate to radezolid (dRD) of the general formula (BP-L-RD), wherein BP is 4-aminophenylethylidene bisphosphonate, L is —OC(O)N—, and RD is radezolid. The bisphosphonate-antimicrobial agent can consist of 4-aminophenylethylidene bisphosphonate linked via a carbamate to radezolid (dRD) of the general formula (BP-L-RD), wherein BP is 4-aminophenylethylidene bisphosphonate, L is —OC(S)N— or —SC(O)N— or —SC(S)N—, and RD is radezolid. The bisphosphonate-antimicrobial agent can consist of 4-aminophenylethylidene bisphosphonate linked via a urea to deacetyl-radezolid (dRD) of the general formula (BP-L-RD), wherein BP is 4-aminophenylethylidene bisphosphonate, L is —NC(O)N— or —NC(S)N—, and RD is radezolid. The bisphosphonate-antimicrobial agent can consist of 4-aminophenylethylidene bisphosphonate linked via a carbamate to deacetyl-radezolid (dRD) of the general formula (BP-L-dRD), wherein BP is 4-aminophenylethylidene bisphosphonate, L is —OC(O)N—, and dRD is deacetyl-radezolid. The bisphosphonate-antimicrobial agent can consist of 4-aminophenylethylidene bisphosphonate linked via a carbamate to deacetyl-radezolid (dRD) of the general formula (BP-L-dRD), wherein BP is 4-aminophenylethylidene bisphosphonate, L is —OC(S)N— or —SC(O)N— or —SC(S)N—, and dRD is deacetyl-radezolid. The bisphosphonate-antimicrobial agent can consist of 4-aminophenylethylidene bisphosphonate linked via a urea to deacetyl-radezolid (dRD) of the general formula (BP-L-dRD), wherein BP is 4-aminophenylethylidene bisphosphonate, L is —NC(O)N— or —NC(S)N—, and dRD is deacetyl-radezolid. The bisphosphonate-antimicrobial agent can consist of 4-hydroxyphenylethylidene bisphosphonate linked via a carbamate to deacetyl-ranbezolid (dRbD) of the general formula (BP-L-dRbD), wherein BP is 4-hydroxyphenylethylidene bisphosphonate, L is —OC(O)N— and dRbD is deacetyl-ranbezolid. The bisphosphonate-antimicrobial agent can consist of 4-hydroxyphenylethylidene bisphosphonate linked via a carbamate to deacetyl-ranbezolid (dRbD) of the general formula (BP-L-dRbD), wherein BP is 4-hydroxyphenylethylidene bisphosphonate, L is —OC(S)N— or —SC(O)N— or —SC(S)N—, and dRbD is deacetyl-ranbezolid. The bisphosphonate-antimicrobial agent can consist of 4-aminophenylethylidene bisphosphonate linked via a urea to deacetyl-ranbezolid (dRbD) of the general formula (BP-L-dRbD), wherein BP is 4-aminophenylethylidene bisphosphonate, L is —NC(O)N— or —NC(S)N—, and dRbD is deacetyl-ranbezolid. The bisphosphonate-antimicrobial agent can consist of 4-aminophenylethylidene bisphosphonate linked via a carbamate to posizolid (PD) of the general formula (BP-L-PD), wherein BP is 4-aminophenylethylidene bisphosphonate, L is —NC(O)O—, and PD is posizolid. The bisphosphonate-antimicrobial agent can consist of 4-aminophenylethylidene bisphosphonate linked via a carbamate to posizolid (PD) of the general formula (BP-L-PD), wherein BP is 4-aminophenylethylidene bisphosphonate, L is —NC(S)O—, and PD is posizolid. The bisphosphonate-antimicrobial agent can consist of 4-hydroxyphenylethylidene bisphosphonate linked via a carbonate to posizolid (PD) of the general formula (BP-L-PD), wherein BP is 4-hydroxyphenylethylidene bisphosphonate, L is —OC(O)O—, and PD is posizolid. The bisphosphonate-antimicrobial agent can be as substantially described by any one of the conjugates in FIG. 7 herein.

In any one or more embodiments herein, a bisphosphonate-antimicrobial agent of any one or more aspects herein can be useful, or can be used for the preparation of a formulation, for treatment of a bone disease. The bone infectious disease can be selected from the group consisting of osteomyelitis, osteolytic bone infections, osteonecrosis, diabetic chronic osteomyelitis, diabetic foot, periodontitis and other jaw infections. The bisphosphonate-antimicrobial agent can be useful for treatment of peripheral (non-bone infections) associated and not associated with bone related infections.

In any one or more embodiments herein, the aforementioned bisphosphonate-antimicrobial agent of any one or more aspects herein can be configured for delivery and release of a target molecule at osseous sites. A formulation comprising a bisphosphonate-antimicrobial as described in any one or more aspects herein, can be provided in the form of an oral rinse solution, a buffered solution for intravenous or parenteral use, or powder/tablet form for enteric administration, or microspheres for direct placement into bone infection sites during surgery. A formulation comprising the bisphosphonate-antimicrobial can comprise an effective amount of the bisphosphonate-antimicrobial agent for the treatment of a bone infectious disease.

In any one or more embodiments herein, a bone graft composition is provided comprising: a bone graft material and the bisphosphonate-antimicrobial agent, wherein the bisphosphonate-antimicrobial agent is attached to, integrated with, chemisorbed to, or mixed with the bone graft material. The bone graft material can be autograft bone material, allograft bone material, xenograft bone material, a synthetic bone graft material, or any combination thereof.

In any one or more embodiments herein, a method is provided comprising: implanting the aforementioned bone graft composition into a subject in need thereof.

In any one or more embodiments herein, a method is provided of preventing biofilm infection at an osseous or implant surgical site, or at a surgical site where bone grafting is performed, where the method comprises: administering the bisphosphonate-antimicrobial agent as described in any one or more aspects herein, to a subject in need thereof, or where the method comprises: implanting the bone graft composition to a subject in need thereof.

Other compounds, compositions, conjugated, formulations, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
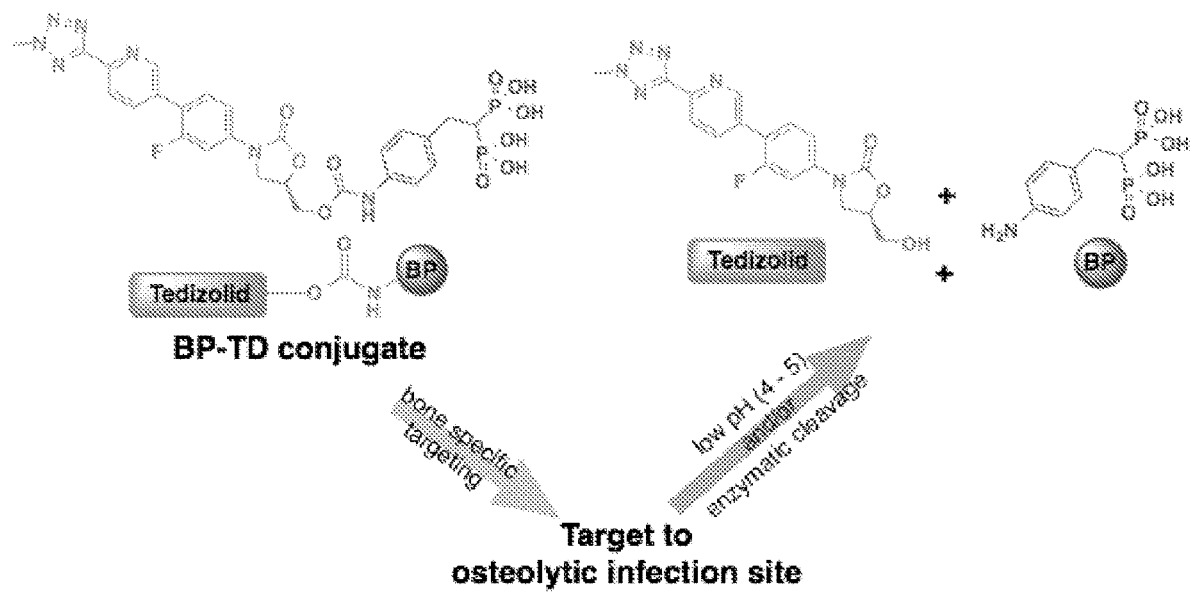
FIG. 1 depicts an exemplary BP-TD conjugate and tedizolid release mechanism of the present disclosure.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, pharmacology, organic chemistry, biochemistry, botany and the like, which are within the skill of the art. Such techniques are explained fully in the literature.

Definitions

Unless otherwise specified herein, the following definitions are provided.

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term "farm animal" includes a horse, sheep, goat, chicken, pig, cow, donkey, llama, alpaca, turkey, and the like.

As used herein, "control" can refer to an alternative subject or sample used in an experiment for comparison purposes and included to minimize or distinguish the effect of variables other than an independent variable.

As used herein, "analog" or "analogue," such as an analogue of a bisphosphonate described herein, can refer to a structurally close member of the parent molecule or an appended parent molecule such as a bisphosphonate.

As used herein, "conjugated" can refer to direct attachment of two or more compounds to one another via one or more covalent or non-covalent bonds. The term "conjugated" as used herein can also refer to indirect attachment of two or more compounds to one another through an intermediate compound, such as a linker.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "active agent" or "active ingredient" refers to a component or components of a composition to which the whole or part of the effect of the composition is attributed.

As used herein, "dose," "unit dose," or "dosage" refers to physically discrete units suitable for use in a subject, each unit containing a predetermined quantity of a BP conjugate, such as a BP quinolone conjugate, composition or formulation described herein calculated to produce the desired response or responses in association with its administration.

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters, amides, hydroxamic acids, or hydrazides. Derivatives include compounds in which hydroxyl groups in the parent compound have been derivatized to form O-acyl, O-carbamoyl, or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring, as an example, with saturated or unsaturated cyclohexane or other more complex, e.g., nitrogen-containing rings, and extensions of these rings with various groups.

As used herein, "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

As used herein, "substituent" or "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl)$C_1$-$C_6$ alkoxy, $C_3$-$C_7$ heterocycloalkyl, ($C_3$-$C_7$ heterocycloalkyl)$C_1$-$C_6$ alkyl, ($C_3$-$C_7$ heterocycloalkyl) $C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, aralkyl, heteroaralkyl, aralkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

The term "alkyl" refers to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl can have 30 or fewer carbon atoms in its backbone (e.g., $C_1$-$C_{30}$ for straight chains, and $C_3$-$C_{30}$ for branched chains). In other embodiments, a straight chain or branched chain alkyl can contain 20 or fewer, 15 or fewer, or 10 or fewer carbon atoms in its backbone. Likewise, in some embodiments cycloalkyls can have 3-10 carbon atoms in their ring structure. In some of these embodiments, the cycloalkyl can have 5, 6, or 7 carbons in the ring structure.

The term "alkyl" (or "lower alkyl") as used herein is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl," as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy," as used herein, refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

The terms "amine" and "amino" (and its protonated form) are art-recognized and refer to both unsubstituted and substituted amines, e.g., a moiety that can be represented by the general formula:

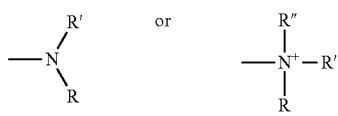

wherein R, R', and R" each independently represent a hydrogen, an alkyl, an alkenyl, —(CH$_2$)$_m$—R$_C$ or R and R' taken together with the N atom to which they are attached complete a heterocycle having from 4 to 8 atoms in the ring structure; R$_C$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

The term "amido" is art-recognized as an amino-substituted carbonyl and includes a moiety that can be represented by the general formula:

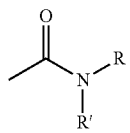

wherein R and R' are as defined above.

As used herein, "aryl" refers to C$_5$-C$_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof. The term "aryl" includes phenyl.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1, 5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

The term "aralkyl," as used herein, refers to an alkyl group substituted with an aryl group (e.g., an aromatic or heteroaromatic group).

The term "aralkyloxy" can be represented by —O-aralkyl, wherein aralkyl is as defined above.

The term "carbocycle," as used herein, refers to an aromatic or non-aromatic ring(s) in which each atom of the ring(s) is carbon.

"Heterocycle" or "heterocyclic," as used herein, refers to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, (C$_1$-C$_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like. The terms "heterocycle" or "heterocyclic" can be used to describe a compound that can include a heterocycle or heterocyclic ring.

The term "carbonyl" is art-recognized and includes such moieties as can be represented by the general formula:

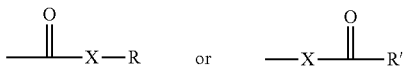

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

The term "heteroatom" as used herein means an atom of any element other than carbon or hydrogen. Exemplary heteroatoms include, but are not limited to, boron, nitrogen, oxygen, phosphorus, sulfur, silicon, arsenic, and selenium. Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

The term "hydroxy" refers to a OH radical.

As used herein, the term "nitro" refers to —$NO_2$; the term "halogen" designates —F, —Cl, —Br, or —I; the term "sulfhydryl" refers to —SH; the term "hydroxyl" refers to —OH; and the term "sulfonyl" refers to —$SO_2$—

As used herein, "carbamate" can be used to refer to a compound derived from carbamic acid ($NH_2COOH$) and can include carbamate esters. "Carbamates" can have the general structure of:

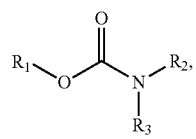

where $R_1$, $R_2$, and $R_3$ can be any permissible substituent.

As used herein, "carbonate" can be used to refer to a compound derived from carbonic acid ($H_2CO_3$) and can include carbonate esters. "Carbonates" can have the general structure of:

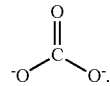

As used herein, "effective amount" can refer to the amount of a composition described herein or pharmaceutical formulation described herein that will elicit a desired biological or medical response of a tissue, system, animal, plant, protozoan, bacteria, yeast or human that is being sought by the researcher, veterinarian, medical doctor or other clinician. The desired biological response can be modulation of bone formation and/or remodeling, including but not limited to modulation of bone resorption and/or uptake of the BP conjugates, such as the BP quinolone conjugates, described herein. The effective amount will vary depending on the exact chemical structure of the composition or pharmaceutical formulation, the causative agent and/or severity of the infection, disease, disorder, syndrome, or symptom thereof being treated or prevented, the route of administration, the time of administration, the rate of excretion, the drug combination, the judgment of the treating physician, the dosage form, and the age, weight, general health, sex and/or diet of the subject to be treated. "Effective amount" can refer to the amount of a compositions described herein that is effective to inhibit the growth of or reproduction of a microorganism, including but not limited to a bacterium or population thereof "Effective amount" can refer to the amount of a compositions described herein that is kill a microorganism, including but not limited to a bacterium or population thereof "Effective amount" can refer to the amount of a compositions described herein that is effective to treat and/or prevent osteomyelitis in a subject in need thereof.

The term "oxazolidinone antimicrobial molecule," "oxazolidinone antimicrobial agent," or "substituents" or "derivatives thereof" and related terms, have the same meaning and refer to antimicrobial agents which are part of the well-known class of "oxazolidinones," also referred to as "oxazolidones", as described in more detail herein.

As used herein, "therapeutic" generally can refer to treating, healing, and/or ameliorating a disease, disorder, condition, or side effect, or to decreasing in the rate of advancement of a disease, disorder, condition, or side effect. The term also includes within its scope enhancing normal physiological function, palliative treatment, and partial remediation of a disease, disorder, condition, side effect, or symptom thereof.

The term "antibacterial" includes those compounds that inhibit, halt or reverse growth of bacteria, those compounds that inhibit, halt, or reverse the activity of bacterial enzymes or biochemical pathways, those compounds that kill or injure bacteria, and those compounds that block or slow the development of a bacterial infection.

As used herein, the terms "treating" and "treatment" can refer generally to obtaining a desired pharmacological and/or physiological effect. The effect may be prophylactic in terms of preventing or partially preventing a disease, symptom or condition thereof. And as used herein are intended to mean, at least, the mitigation of a disease condition associated with a bacterial infection in a subject, including mammals, such as a human, that is alleviated by a reduction of growth, replication, and/or propagation of any bacterium such as Gram-positive organisms, and includes curing, healing, inhibiting, relieving from, improving and/or alleviating, in whole or in part, the disease condition.

The term "prophylaxis" is intended to mean at least a reduction in the likelihood that a disease condition associated with a bacterial infection will develop in a mammal, preferably a human. The terms "prevent" and "prevention" are intended to mean blocking or stopping a disease condition associated with a bacterial infection from developing in a mammal, preferably a human. In particular, the terms are related to the treatment of a mammal to reduce the likelihood ("prophylaxis") or prevent the occurrence of a bacterial infection, such as bacterial infection that may occur during or following a surgery involving bone reparation or replacement. The terms also include reducing the likelihood ("prophylaxis") of or preventing a bacterial infection when the mammal is found to be predisposed to having a disease condition but not yet diagnosed as having it. For example, one can reduce the likelihood or prevent a bacterial infection in a mammal by administering a compound of Formula (1) and/or Formula (2), or a pharmaceutically acceptable prodrug, salt, active metabolite, or solvate thereof, before occurrence of such infection.

As used herein, "synergistic effect," "synergism," or "synergy" refers to an effect arising between two or more molecules, compounds, substances, factors, or compositions that is greater than or different from the sum of their individual effects.

As used herein, "additive effect" refers to an effect arising between two or more molecules, compounds, substances, factors, or compositions that is equal to or the same as the sum of their individual effects.

The term "biocompatible", as used herein, refers to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

As used herein, the term "osteomyelitis" can refer to acute or chronic osteomyelitis, and/or diabetic foot osteomyelitis, diabetic chronic osteomyelitis, prosthetic joint infections, periodontitis, peri-implantitis, osteonecrosis, and/or hematogenous osteomyelitis and/or other bone infections.

Discussion

Methylenebisphosphonates or substituted methylidine bisphosphonate moieties, commonly referred to as "bisphosphonates" (BPs) are therapeutic agents for the treatment of many bone disorders. The bisphosphonate P—C—P group mimics the P—O—P bond of the naturally-occurring mediator of bone metabolism, inorganic pyrophosphate. The structural relationship of pyrophosphate and methylene bisphosphonates in acid form is shown below. Individual BPs can be defined by the covalently attached substituents $R_1$ and $R_2$.

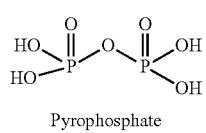

Pyrophosphate

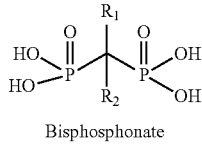

Bisphosphonate

The bridging carbon of the bisphosphonate can be substituted with modifying groups ($R_1$, $R_2$) to confer specific biological properties on the derivative. BPs exhibit strong binding affinity to HA, the major inorganic material found in bone, particularly at sites of high bone turnover, and they are exceptionally stable to both chemical and biological degradation. It is often underappreciated that BPs also traverse through soft and hard tissues of the body (e.g. endothelium, periosteum, HA) to target bone and the canalicular network and vascular canals within bones. These highly specific bone-targeting properties of BPs make them ideal carriers to deliver drugs or macromolecules to bone surfaces.

The Oxazolidinone antibiotics are an ideal small molecule class of antibiotics effective against the major pathogens associated with bone infections. This series is led by tedizolid, one of the most recently licensed drugs active against S. aureus (MSSA and MRSA). Tedizolid is a second-generation oxazolidinone, following the first-generation linezolid. Tedizolid was FDA-approved for U.S. marketing in June 2014 as treatment of acute bacterial skin and skin structure infections (ABSSSI). Six days of once-daily tedizolid was non-inferior to 10 days of twice-daily linezolid in two phase 3 studies. The drug appears to have fewer gastrointestinal side effects and hematologic suppression than linezolid, although experience with courses longer than 6 days has not been published, so the true incidence of toxicity if it were to be given for prolonged courses typical of bone and joint infections remains unknown. Nevertheless, the drug's overall potency against S. aureus and apparent safety, coupled with desirable chemical properties, make it an attractive candidate for specific delivery to bone for the treatment of infectious bone diseases.

From the foregoing description, there is an important yet unmet medical need for improved antimicrobial agents to treat bone infections. Embodiments of the disclosure provided herein can provide bone-targeted antimicrobial agents to treat bone infections and, in some embodiments, overcome the deficiencies of traditional treatment compositions and methods. Generally, the compositions described herein can include a bisphosphonate-antimicrobial (BP-Ab) conjugate that contains an antimicrobial agent, e.g., an oxazolidinone, in particular an oxazolidinone antimicrobial or antibiotic substituent or derivative, such as tedizolid (TD), to a bisphosphonate (BP).

The compositions provided herein can employ a "target and release linker" strategy, where a releasable and bone-specific targeting bisphosphonate-antimicrobial (BP-Ab) conjugate can be made by attaching the antimicrobial agent, e.g., an oxazolidinone, to a pharmacologically inert BP or pharmacologically active BP using a cleavable or reversible linker, such as carbamate, hydrazone, et al., or carbonate, so that the antimicrobial agent can be released upon binding to bone surfaces by the decreased pH and/or enzymatic environment which is typically found at active sites of bone resorption or infection. An exemplary BP-Oxazolidinone release mechanism is depicted in FIG. 1 using tedizolid (TD) as an exemplary oxazolidinone. This BP-Ab conjugate can have the ability to deliver and release the antimicrobial agent specifically to the targeted infectious osteolytic site, thus offering a unique treatment option by providing a higher concentration of antimicrobial agent at the disease site and relatively lower systemic levels. Other oxazolidinone-BP compounds and conjugates, as described herein, can have the same or similar activity.

Also provided herein are formulations that can include an amount of a compound, conjugate or composition described herein and an additional compound (such as, but not limited to, a carrier, diluent, or other active agent or ingredient). The formulation can be a pharmaceutical formulation that can contain a pharmaceutically acceptable carrier. The compositions and/or formulations can be administered to a subject. The subject can have a bone infection. The compositions and formulations provided herein can be used to treat and/or prevent bone infection. The compositions and formulations provide herein can provide, in some embodiments, bone specific delivery of an antimicrobial agent.

The general concept of targeting active drug species to the bone compartment with BP has been discussed in a number of reports. However, no drugs have yet been developed, as early attempts led to either systemically unstable prodrugs or non-cleavable conjugates that were found mostly to inactivate either component of the conjugate by interfering with the pharmacophoric requirements. This suggests that target and release strategies are likely chemical class-dependent (taking into consideration compatibilities of the functional groups of each component) as well as biochemical target-dependent, and the design for any particular chemical class must be customized for its use. Therefore, provided herein are embodiments of a novel approach to develop a bone targeted antimicrobial agent with a linkage that can be metabolically stable in the bloodstream and metabolically labile on bone to facilitate appropriate release.

In particular, in any one or more aspects herein, the linkages utilized herein are designed to allow maximum local antibacterial efficacy at the site of an infection where higher bone turnover exists, while also limiting exposure of lower turnover skeletal sites, non-skeletal sites, and distant compartments throughout the body from any adverse effect due to antibiotic or bisphosphonate components or conjugate. Thus, for example, the aryl carbamate linkers herein are specifically selected to have maximum stability in the bloodstream, while still having sensitivity to chemically cleave and release oxazolidinone antibiotics at skeletal sites of bacterial infection, due to their sensitivity to the enzymatic processes and pH characteristics of that environment. Furthermore, select, but not all, embodiments in this disclosure, include the use of bisphosphonates that do not have significant pharmacological activity for the targeting component of these drug conjugates. These "nonantiresorptive" or weak antiresorptive bisphosphonates have the characteristics of only targeting the antibiotic to the bone compartments described and do not have properties to otherwise affect bone metabolism directly. Examples include aryl carbamates and aryl thiocarbamates derived from substituted and unsubstituted 2-[4-aminophenyl]ethane 1,1 bisphosphonate and 2-[4-hydroxyphenyl]ethane 1,1 bisphosphonate. Also, included are carbamates derived from substituted and unsubstituted 2-[3-aminophenyl]ethane 1,1 bisphosphonate and 2-[3-hydroxyphenyl]ethane 1,1 bisphosphonate substituted and unsubstituted 2-[2-aminophenyl] ethane 1,1 bisphosphonate and 2-[2-hydroxyphenyl]ethane 1,1 bisphosphonate. Furthermore, aryl dithiocarbamates, derived from substituted and unsubstituted 2-[4-thiophenyl] ethane 1,1 bisphosphonate, 2-[3-thiophenyl]ethane 1,1 bisphosphonate, and 2-[2-thiophenyl]ethane 1,1 bisphosphonate.

Figure 2:
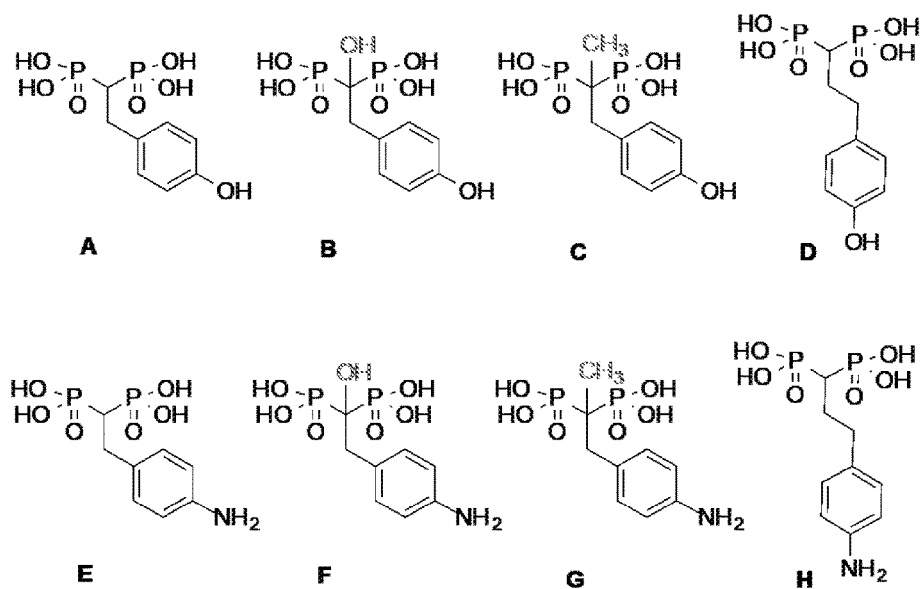
FIG. 2 depicts examples of pharmacologically inert BPs used in conjugation: medium (A/E), high (B/F), and low (C/G) affinity BPs and longer phenylalkyl chain BP (D/H).

In any one or more aspects the BP of the conjugate can be a pharmacologically inert BP. Examples of pharmacologically inert BPs that can be conjugated with an oxazolidinone as described herein are shown in FIG. 2.

As an example, the inert BP series for the conjugation can be 4-hydroxyphenylethylidene BP (FIG. 2A) or 4-aminophenylethylidene BP (FIG. 2E) having a medium mineral affinity. Further analogs such as hydroxy BP (FIGS. 2B and 2F) (higher mineral affinity) and methyl BP (FIGS. 2C and 2G) (lower mineral affinity) can be used to adjust the concentration of the BP-Ab conjugates at bone. Phenyl alkyl BPs with different chain lengths such as in FIGS. 2D and 2H (propyl or butyl vs. ethyl phenyl) can also be utilized to optimize the conjugation chemistry yields and conjugate stability.

Bisphosphonate (BP) Oxazolidinone Conjugates and Formulations Thereof

BP Oxazolidinone Conjugates

Provided herein are BP oxazolidinone compounds, conjugates and formulations thereof. A BP can be conjugated to an oxazolidinone via a linker. In embodiments, the linker is a releasable linker. The oxazolidinone can be releasably attached via a linker to the BP. Thus, in any one or more embodiments, the BP oxazolidinone compound or conjugate can selectively deliver and release the oxazolidinone, in particular an oxazolidinone antimicrobial or antibiotic substituent or derivative, at or near bone, bone grafts, or bone graft substitutes (FIG. 1). In other words, the BP conjugate can provide targeted delivery of oxazolidinones, such as tedizolid (TD), to bone and/or the areas proximate to bone.

The BP of the BP oxazolidinone conjugates provided herein can be any BP including but not limited to, hydroxyl phenyl alkyl or aryl bisphosphonates, hydroxyl phenyl (or aryl) alkyl hydroxyl bisphosphonates, amino phenyl(or aryl) alkyl bisphosphonates, amino phenyl(or aryl) alkyl hydroxyl bisphosphonates, hydroxyl alkyl bisphosphonates, hydroxyl alkyl hydroxyl bisphosphonates hydroxyl alkyl phenyl(or aryl) alkyl bisphosphonates, hydroxyl phenyl(or aryl) alkyl hydroxyl bisphosphonates, amino phenyl(or aryl) alkyl bisphosphonates, amino phenyl(or aryl) alkyl hydroxyl bisphosphonates, hydroxyl alkyl bisphosphonates, hydroxyl alkyl hydroxyl bisphosphonates (all of the former being further unsubstituted or substituted, etidronate, pamidronate, neridronate, olpadronate, alendronate, ibandronate, minodronate, risedronate, zoledronate, hydroxymethylenebisphosphonate, and combinations thereof. Bisphosphonate may also be substituted for phosphono phosphinic acid or phosphono carboxylic acid. In embodiments, the BP can be pamidronate, alendronate, risedronate, zoledronate, minodronate, neridronate, etidronate, which can be unmodified or modified as described herein.

Figure 4A:
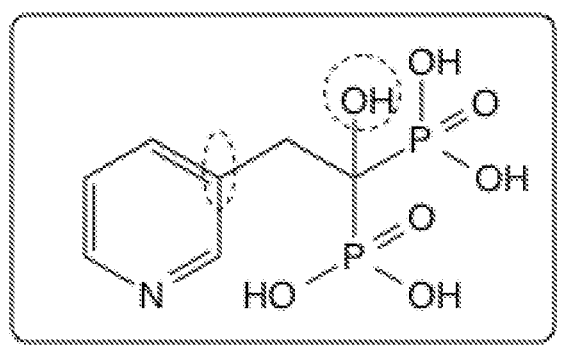
FIG. 4A depicts an alpha-hydroxy modified risedronate and zoledronate.
Figure 4A:
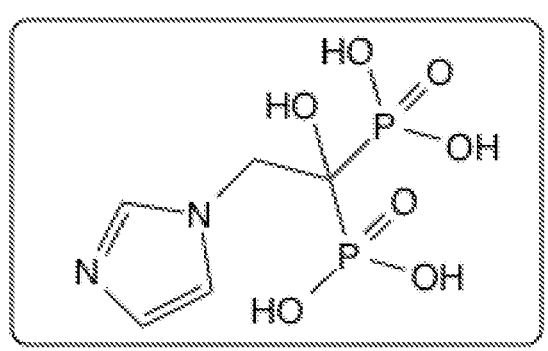
Figure 4B:
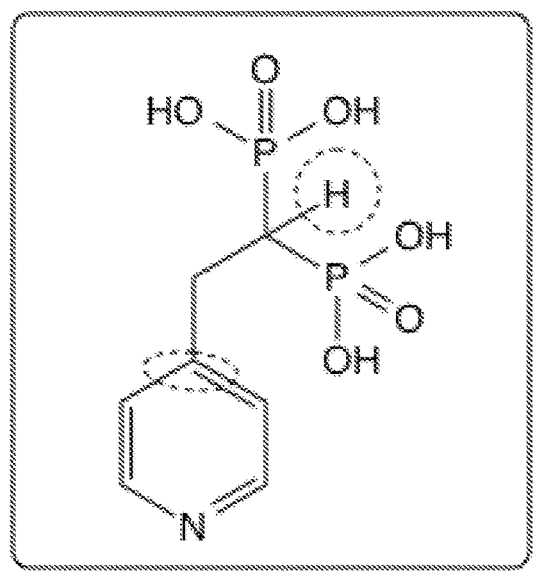
FIG. 4B depicts 1) a BP modified by substituting or removing the alpha-hydroxy group (pPyrEBP); 2) a BP modified by substituting at the para-position of pyridine ring (p-RIS). The circled H is attached to the alpha carbon of the bisphosphonate substituted carbon chain.
Figure 4B:
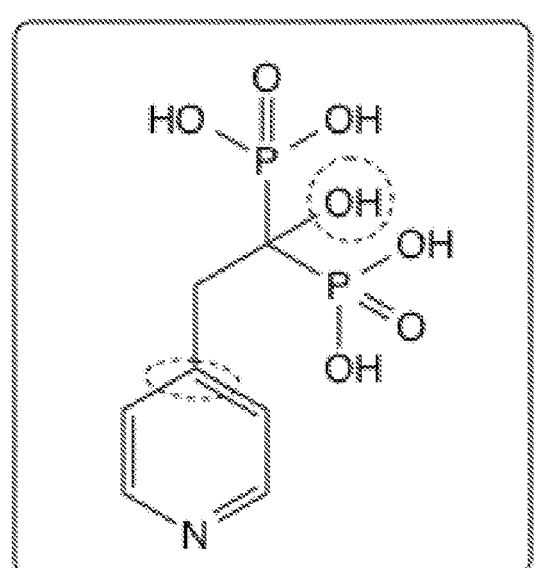

The BP can be modified to contain an alpha-hydroxy group (e.g. alpha-hydroxy modified risedronate and zoledronate, FIG. 4A) Other BPs can be modified in the same way. In some embodiments, the BP can be modified by substituting or removing the alpha-hydroxy group. (FIG. 4B, e.g. p-PyrEBP). Removal or substitution of the alpha-hydroxyl group can reduce or eliminate the anti-resorptive effect of the BP as compared to an unmodified equivalent BP. As such, in any one or more embodiments, the BP conjugates provided herein can contain a BP that lacks the alpha-hydroxy group or has a substituted alpha-hydroxy group. Suitable substitutions for the alpha-hydroxy group can include, but are not limited to, H, alkyl, aryl, alkyl aryl. Further additional molecules conjugated to the BP can also affect the anti-resorptive effect. For example, when the oxazolidone and/or linker is coupled to the BP having a para-substituted side change, the anti-resorptive effect can be significantly reduced or eliminated. In any one or more embodiments, the BP can be modified to include both an alpha hydroxyl deletion or substitution and a para-substituted side chain.

In BPs containing an aryl or phenyl, the aryl or phenyl can be substituted with a suitable substituent at any position on the ring. In any one or more embodiments, the aryl or phenyl ring of the BP is substituted with one or more electron donating species (e.g. F, N, and Cl).

Non-pharmacologically active BP variants may also be used for the purpose of delivery absent BP action.

The oxazolidinone can have a generic structure according to Formula (5), where $R^1$ can be known components of oxazolidinone antimicrobial or antibiotic substituent or derivative compounds, and can include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups; and where $R^2$ can be substituents including a releasable linker, as described herein, involved in the linkage to a bisphosphonate, as described herein, and can include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

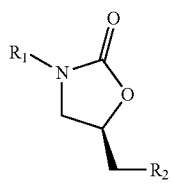

Formula (5)

The BP can be conjugated to the oxazolidinone, in particular an oxazolidinone antimicrobial or antibiotic substituent or derivative, via a releasable linker, as described herein. In any one or more aspects, the linker can be a carbamate or a carbonate of the structure of Formula (6) or Formula (7), respectively. In some embodiments the releasable linker can be a phenyl carbamate linker. The releasable linker can be an aryl carbamate linker. In some embodiments the linker can be an aryl thiocarbamate linker. In some embodiments the linker can be a phenyl thiocarbamate linker. In some embodiments the thiocarbamate linker can be an O-thiocarbamate linker. In some embodiments, the thiocarbamate linker can be an S-thiocarbamate linker. In some embodiments the linker can be a urea linker. In some embodiments, the linker can be an aryl dithiocarbamate linker. In some embodiments, the linker can be an ester linker.

Figure 3:
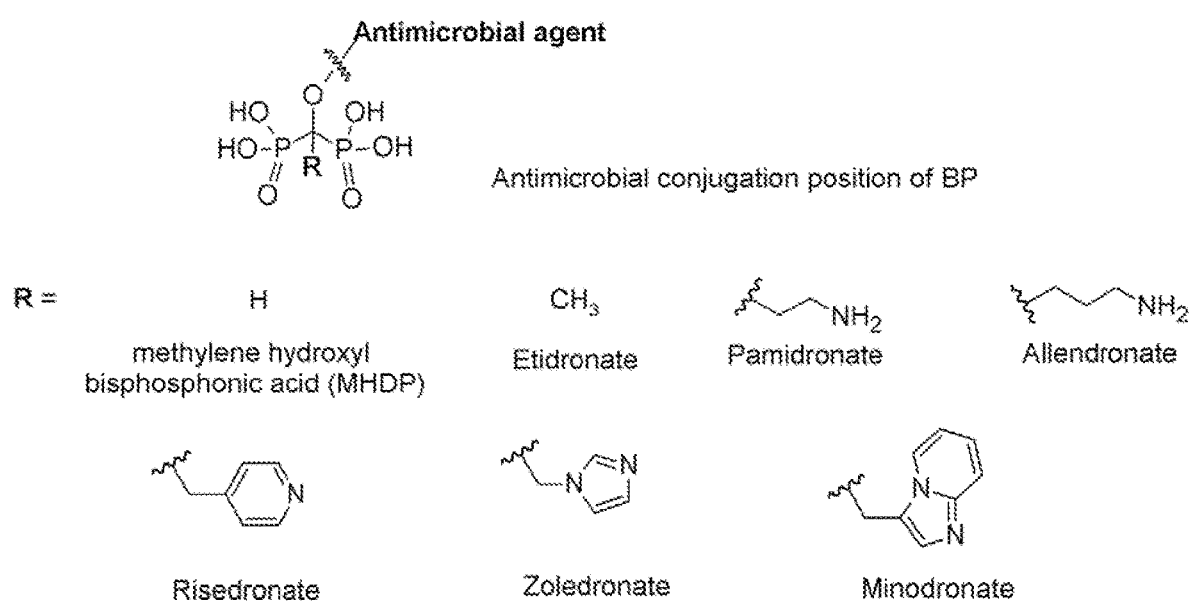
FIG. 3 depicts examples of pharmacologically active BPs that can be used in the present conjugation.

In some aspects, an alpha-hydroxy containing BP can be conjugated to the oxazolidinone (or oxazolidone), such as a tedizolid (TD), at a geminal OH group on the BP as shown below. This can be achieved, for example, using a hydroxy-derived carbamate. This can be particularly advantageous for conjugating pharmacologically active BP variants as shown in FIG. 3. In some aspects, the oxazolidinone, such as TD, can be directly conjugated (e.g. no linker) to geminal OH group of the BP. In some aspects, the oxazolidinone can be indirectly conjugated via a linker at the geminal OH group of the BP.

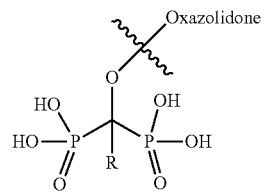

conjugates between alpha-OH containing BP and oxazolidone

In some aspects, an amino phenyl containing BP, such as any one of the pharmacologically inert BP variants shown in FIG. 2, can be conjugated to the oxazolidinone, such as Tedizolid (TD), preferably by an aryl carbamate linker, as shown below. This can have the advantage of controlling the release of the oxazolidinone antimicrobial compound as compared to the oxazolidinone compounds conjugated to the active BP variants of, for example, FIG. 3. The inactive BP variants can have less side effects than the active BP variants, such as potentially lower toxicity than the active BP variants in which case higher concentrations or dosages of the compounds and conjugates incorporating the inactive BP variants can be used as compared to the compounds and conjugates incorporating active BP variants.

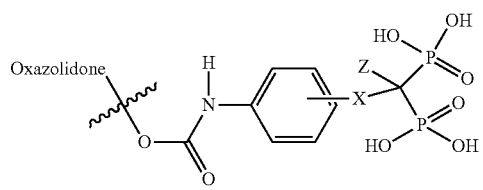

In some aspects, the compound can have a formula according to Formula (2), Formula (3), Formula (4), or Formula (5).

Formula (2)

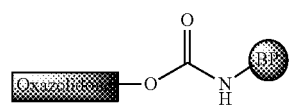

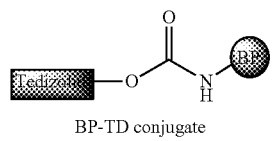

BP-TD conjugate

Formula (3)

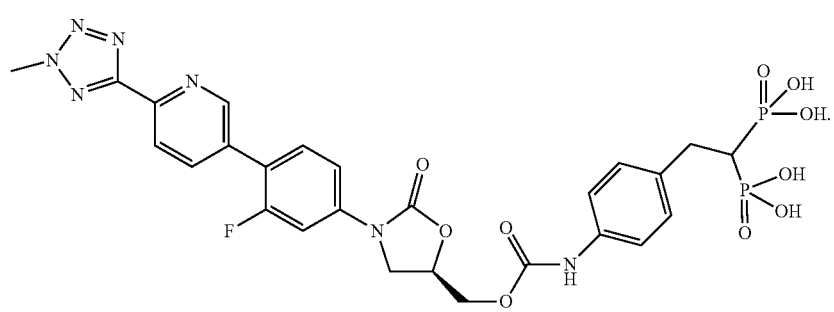

Formula (4)

BP Oxazolidinone Conjugate Pharmaceutical Formulations

Also described herein are formulations, including pharmaceutical formulations, which can contain an amount of a BP oxazolidinone conjugate or compound as described elsewhere herein. The amount can be an effective amount. The amount can be effective to inhibit the growth and/or reproduction of a bacterium. The amount can be effective to kill a bacterium. The amount can be effective to treat or inhibit, or used as a prophylaxis agent against, a bone disease, in particular an infectious bone disease. The amount can be effective to treat or inhibit osteomyelitis, osteolytic bone infections, osteonecrosis, diabetic chronic osteomyelitis, diabetic foot, periodontitis and other jaw infections.

Formulations, including pharmaceutical formulations can be formulated for delivery via a variety of routes and can contain a pharmaceutically acceptable carrier. Techniques and formulations generally can be found in *Remmington's Pharmaceutical Sciences*, Meade Publishing Co., Easton, Pa. (20th Ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers such as Hank's solution or Ringer's solution. In addition, the BP oxazolidinone conjugates and/or compounds herein can be formulated in solid form and re-dissolved or suspended immediately prior to use. Lyophilized forms are also included. Formulations, including pharmaceutical formulations, of the BP oxazolidinone compounds or conjugates can be characterized as being at least sterile and pyrogen-free. These formulations include formulations for human and veterinary use.

Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxyl methylcellulose, and polyvinyl pyrrolidone, which do not deleteriously react with BP oxazolidinone compound or conjugate.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the BP oxazolidinone compound or conjugate.

Another formulation includes the addition of one or more BP oxazolidinone compounds and/or conjugates to bone graft material or bone void fillers for the prevention or treatment of osteomyelitis, peri-implantitis or peri-prosthetic infections, and for socket preservation after dental extractions.

A pharmaceutical formulation can be formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Formulations, including pharmaceutical formulations, suitable for injectable use can include sterile aqueous solutions (where water soluble) or dispersions and sterile powders for the extemporaneous preparation of sterile injectable solutions or dispersions. For intravenous administration, suitable carriers can include physiological saline, bacteriostatic water, Cremophor EM™ (BASF, Parsippany, N.J.) or phosphate buffered saline (PBS). Injectable pharmaceutical formulations can be sterile and can be fluid to the extent that easy syringability exists. Injectable pharmaceutical formulations can be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it can be useful to include isotonic agents, for example, sugars, polyalcohols such as mannitol, sorbitol, and sodium chloride in the composition.

Sterile injectable solutions can be prepared by incorporating any one or more of the BP oxazolidinone compounds or conjugates described herein in an amount in an appropriate solvent with one or a combination of ingredients enumerated herein, as required, followed by filtered sterilization. Generally, dispersions can be prepared by incorporating the one or more BP oxazolidinone compounds or conjugates into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Systemic administration can also be by transmucosal or transdermal means. For transmucosal or transdermal administration, penetrants appropriate to the barrier to be permeated can be used in the formulation. Such penetrants are generally known in the art, and include, for example, for transmucosal administration, detergents, bile salts, and fluidic acid derivatives. Transmucosal administration can be accomplished through the use of nasal sprays or suppositories. For transdermal administration, the BP oxazolidinone conjugates can be formulated into ointments, salves, gels, or creams as generally known in the art. In some embodiments, the one or more BP oxazolidinone compounds and/or conjugates can be applied via transdermal delivery systems, which can slowly release the BP oxazolidinone conjugates for percutaneous absorption. Permeation enhancers can be used to facilitate transdermal penetration of the active factors in the conditioned media. Transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

For oral administration, a formulation, as described herein, can be presented as capsules, tablets, powders, granules, or as a suspension or solution. The formulation can contain conventional additives, such as lactose, mannitol, cornstarch or potato starch, binders, crystalline cellulose, cellulose derivatives, acacia, cornstarch, gelatins, disintegrators, potato starch, sodium carboxymethylcellulose, dibasic calcium phosphate, anhydrous or sodium starch glycolate, lubricants, and/or or magnesium stearate.

For parenteral administration (i.e., administration through a route other than the alimentary canal), the formulations described herein can be combined with a sterile aqueous solution that is isotonic with the blood of the subject. Such a formulation can be prepared by dissolving the active ingredient (e.g. the BP oxazolidinone compound or conjugate) in water containing physiologically-compatible substances, such as sodium chloride, glycine and the like, and having a buffered pH compatible with physiological conditions, so as to produce an aqueous solution, then rendering the solution sterile. The formulation can be presented in unit or multi-dose containers, such as sealed ampoules or vials. The formulation can be delivered by injection, infusion, or other means known in the art.

For transdermal administration, the formulations described herein can be combined with skin penetration enhancers, such as propylene glycol, polyethylene glycol, isopropanol, ethanol, oleic acid, N-methylpyrrolidone and the like, which increase the permeability of the skin to the nucleic acid vectors of the invention and permit the nucleic acid vectors to penetrate through the skin and into the bloodstream. The formulations and/or compositions described herein can be further combined with a polymeric substance, such as ethylcellulose, hydroxypropyl cellulose, ethylene/vinyl acetate, polyvinyl pyrrolidone, and the like, to provide the composition in gel form, which can be dissolved in a solvent, such as methylene chloride, evaporated to the desired viscosity and then applied to backing material to provide a patch.

For inclusion in bone graft substitutes or bone void fillers to prevent local post-operative infection or graft failure after surgery, and to provide sustained local release of antibiotic at the graft site, the formulations described herein can be combined with any xenograft (bovine), autograft (self) or allograft (cadaver) material or synthetic bone substitute, particularly substances, materials or surfaces containing hydroxyapatite. For example, a powder formulation can be premixed by the treating surgeon or clinician bedside/chair-side with any existing bone graft substitute on the market or with an autologous graft. This formulation can be further combined with any previously described formulation, and can be combined with products containing hydroxyapatites, tricalcium phosphates, collagen, aliphatic polyesters (poly (lactic) acids (PLA), poly(glycolic)acids (PGA), and polycaprolactone (PCL), polyhydroxybutyrate (PHB), methacrylates, polymethylmethacrylates, resins, monomers, polymers, cancellous bone allografts, human fibrin, platelet rich plasma, platelet rich fibrin, plaster of Paris, apatite, synthetic hydroxyapaptite, coralline hydroxyapatite, wollastonite (calcium silicate), calcium sulfate, bioactive glasses, ceramics, titanium, devitalized bone matrix, non-collagenous proteins, collagen, and autolyzed antigen extracted allogenic bone. In this embodiment the bone graft material combined with BP-oxazolidinone conjugate can be in the formulation of a paste, powder, putty, gel, hydrogel, matrix, granules, particles, freeze-dried powder, freeze-dried bone, demineralized freeze-dried bone, fresh or fresh-frozen bone, corticocancellous mix, pellets, strips, plugs, membranes, lyophilized powder reconstituted to form wet paste, spherules, sponges, blocks, morsels, sticks, wedges, cements, or amorphous particles; many of these may also be in injectable formulations or as a combination of two or more aforementioned formulations (e.g. injectable paste with sponge).

In another embodiment, one or more BP-oxazolidinone compounds or conjugates can be combined with factor-based bone grafts containing natural or recombinant growth factors, such as transforming growth factor-beta (TGF-beta), platelet-derived growth factor (PDGF), fibroblast growth factors (FGF), and/or bone morphogenic protein (BMP). In another embodiment, one or more BP oxazolidinone compounds or conjugates, as described herein, can be combined with cell-based bone grafts used in regenerative medicine and dentistry including embryonic stem cells and/or adults stem cells, tissue-specific stem cells, hematopoietic stem cells, epidermal stem cells, epithelial stem cells, gingival stem cells, periodontal ligament stem cells, adipose stem cells, bone marrow stem cells, and blood stem cells. Therefore, a bone graft with the property of osteoconduction, osteoinduction, osteopromotion, osteogenesis, or any combination thereof can be combined with one or more BP oxazolidinone compounds or conjugates for clinical or therapeutic use.

Dosage Forms

The BP oxazolidinone compounds, conjugates and formulations described herein can be provided in unit dose form such as a tablet, capsule, single-dose injection or infusion vial, or as a predetermined dose for mixing with bone graft material as in formulations described above. Where appropriate, the dosage forms described herein can be microencapsulated. The dosage form can also be prepared to prolong or sustain the release of any ingredient. In some embodiments, the complexed active agent can be the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Coatings may be formed with a different ratio of water-soluble polymer, water insoluble polymers, and/or pH dependent polymers, with or without water insoluble/water soluble non polymeric excipient, to produce the desired release profile. The coatings can be either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Effective Amounts

The formulations can contain an effective amount of a BP oxazolidinone conjugate (effective for inhibiting and/or killing a bacterium) described herein. In some embodiments, the effective amount ranges from about 0.001 pg to about 1,000 g or more of the BP oxazolidinone compound or conjugate described herein. In some embodiments, the effective amount of the BP oxazolidinone compound or conjugate described herein can range from about 0.001 mg/kg body weight to about 1,000 mg/kg body weight. In yet other embodiments, the effective amount of the BP oxazolidinone compound or conjugate can range from about 1% w/w to about 99% or more w/w, w/v, or v/v of the total formulation. In some embodiments, the effective amount of the BP oxazolidinone compound or conjugate is effective at killing a bacterium that is the causative agent of osteomyelitis and all its subtypes (e.g. diabetic foot osteomyelitis), jaw osteonecrosis, and periodontitis including, but not limited to any strain or species of *Staphylococcus, Pseudomonas, Aggregatibacter, Actinomyces, Streptococcus, Haemophilus, Salmonella, Serratia, Enterobacter, Fusobacterium, Bacteroides, Porphyromonas, Prevotella, Veillonella, Campylobacter, Peptostreptococcus, Eikenella, Treponema, Dialister, Micromonas, Yersinia, Tannerella*, and *Escherichia.*

Methods of Using the BP Oxazolidinone Compounds and Conjugates

An amount, including an effective amount, of the BP oxazolidinone compounds, conjugates and formulations thereof described herein can be administered to a subject in need thereof. In some embodiments the subject in need thereof can have a bone infection, disease, disorder, or a symptom thereof. In some embodiments, the subject in need thereof can be suspected of having or is otherwise predisposed to having a bone infection, disease, disorder, or a symptom thereof. In some embodiments, the subject in need thereof may be at risk for developing an osteomyelitis, osteonecrosis, peri-prosthetic infection, and/or peri-implantitis. In embodiments, the disease or disorder can be osteomyelitis and all its subtypes, osteonecrosis, peri-implantitis or periodontitis. In some embodiments the subject in need thereof has a bone that is infected with a microorganism, such as a bacteria. In some embodiments, the bacteria can be any strain or species of *Staphylococcus, Pseudomonas, Aggregatibacter, Actinomyces, Streptococcus, Haemophilus, Salmonella, Serratia, Enterobacter, Fusobacterium, Bacteroides, Porphyromonas, Prevotella, Veillonella, Campylobacter, Peptostreptococcus, Eikenella, Treponema, Dialister, Micromonas, Yersinia, Tannerella*, and *Escherichia*. In some embodiments, the bacteria can form biofilms. In some embodiments, osteomyelitis can be treated in a subject in need thereof by administering an amount, such as an effective amount, of BP oxazolidinone compound, conjugate or formulation described herein to the subject in need thereof. In some embodiments, the compositions, compounds and formulations provided herein can be used in osteonecrosis treatment and/or prevention, distraction osteogenesis, cleft repair, repair of critical supra-alveolar defects, jawbone reconstruction, and any other reconstructions or repair of a bone and/or joint.

Administration of the BP oxazolidinone compounds and conjugates is not restricted to a single route but can encompass administration by multiple routes. For instance, exemplary administrations by multiple routes include, among others, a combination of intradermal and intramuscular administration, or intradermal and subcutaneous administration. Multiple administrations can be sequential or concurrent. Other modes of application by multiple routes will be apparent to the skilled artisan.

The pharmaceutical formulations can be administered to a subject by any suitable method that allows the agent to exert its effect on the subject in vivo. For example, the formulations and the compounds and compositions described herein can be administered to the subject by known procedures including, but not limited to, by oral administration, sublingual or buccal administration, parenteral administration, transdermal administration, via inhalation, via nasal delivery, vaginally, rectally, and intramuscularly. The formulations and the compounds and compositions described herein can be administered parenterally, by epifascial, intracapsular, intracutaneous, subcutaneous, intradermal, intrathecal, intramuscular, intraperitoneal, intrasternal, intravascular, intravenous, parenchymatous, and/or sublingual delivery. Delivery can be by injection, infusion, catheter delivery, or some other means, such as by tablet or spray. Delivery can also be by a carrier such as hydroxyapatite or bone in the case of anti-infective bone graft material at a surgical site. Delivery can be via attachment or other association with a bone graft material.

Examples

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

In any one or more aspects, the BP of the conjugate can be a pharmacologically inert BP. Examples of pharmacologically inert BPs that can be conjugated with oxazolidinone as described herein are shown in FIG. 2. As an example, the inert BP series (FIG. 2) for the conjugation can be 4-hydroxyphenylethylidene BP (FIG. 2A) or 4-aminophenylethylidene BP (FIG. 2E). Further analogs such as hydroxy BP (FIGS. 2B and 2F) (higher mineral affinity) and methyl BP (FIGS. 2C and 2G) (lower mineral affinity) can be used to adjust the concentrations of the BP-Ab conjugates at bone. Phenyl alkyl BPs with different chain lengths such as shown in FIGS. 2D and 2H (propyl or butyl vs. ethyl or phenyl) can also be utilized to optimize the conjugation chemistry yields and conjugate stability.

As an example, a BP with high or intermediate pharmacological activity, e.g., etidronate, methylene hydroxyl bisphosphonic acid (MHDP), pamidronate, alendronate, risedronate, zoledronate, minodronate, et al. as depicted in FIG. 3 can also be used in the conjugation to provide a well-studied bisphosphonate component or a dual active agent that protects against bone loss and bone infections since it is known that bone resorption occurs at sites of infection.

Figure 5:
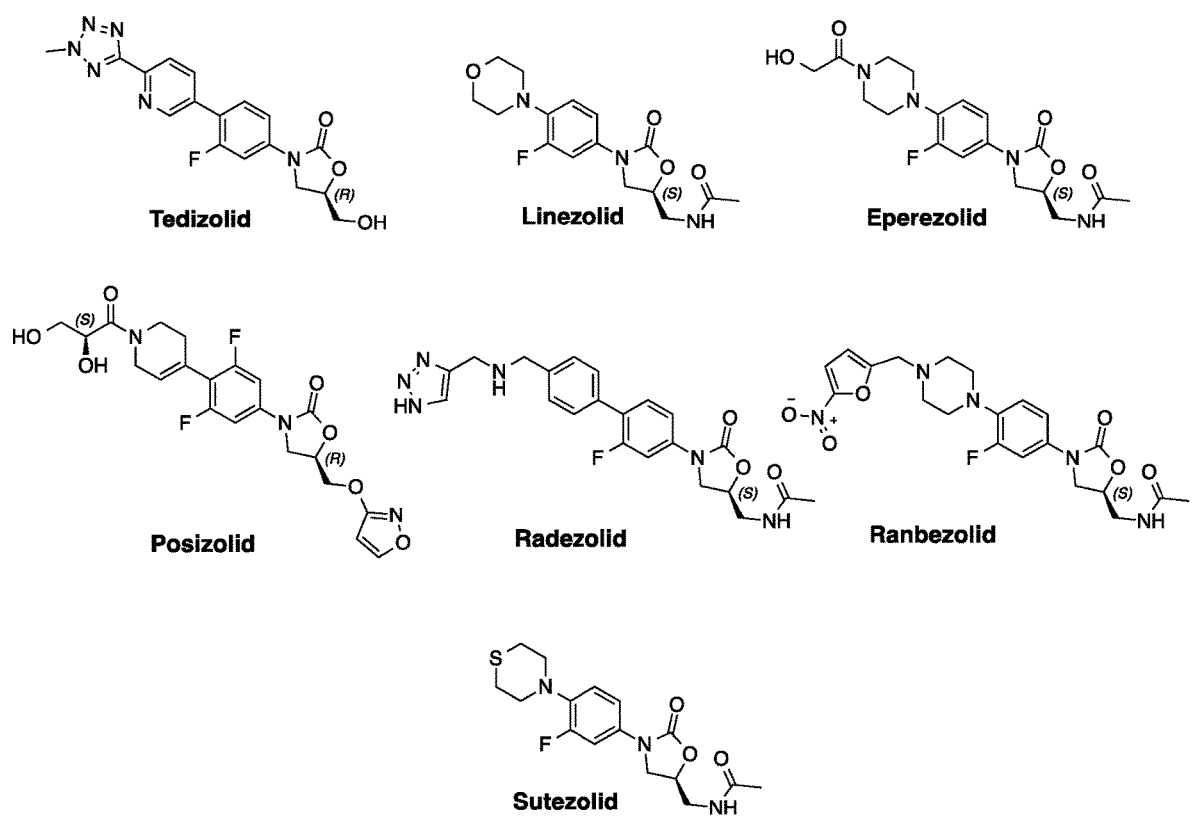
FIG. 5 depicts examples of oxazolidinone antibacterial agents that can be used in conjugation with bisphosphonates.
Figure 6:
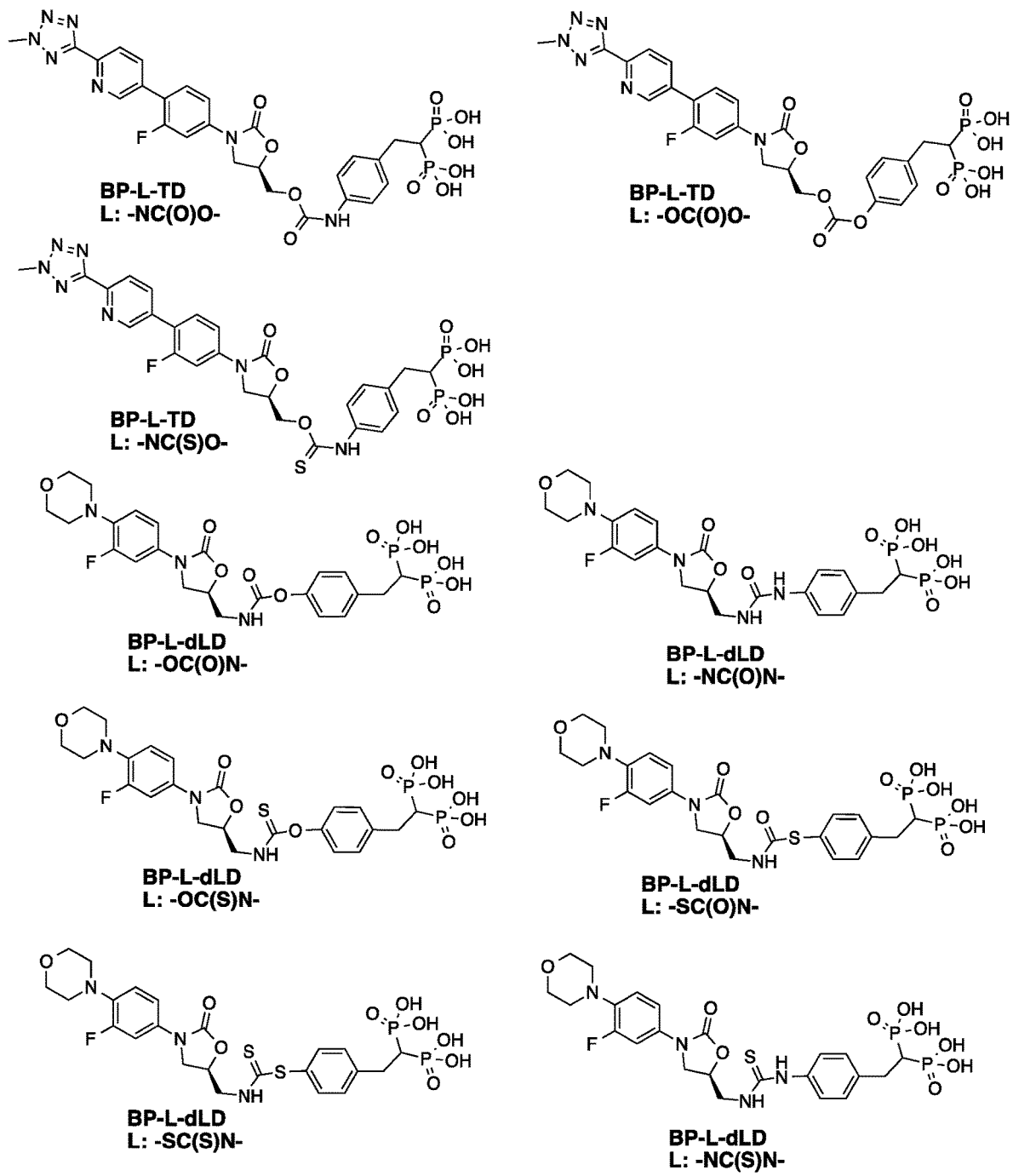
FIG. 6 depicts examples of bisphosphonate-oxazolidinone conjugates of the present disclosure.

As an example, the antimicrobial agents of the present conjugates and compounds can be an oxazolidinone analog of Formula (5) herein or any of oxazolidinone agents shown in FIG. 5. The oxazolidinone antimicrobial or antibiotic agents can be substituents or derivatives of an oxazolidinone. For example, in the case of linezolid, the terminal amido, or amino-substituted carbonyl group, can be substituted with a linker to provide release of a des-acetyl (or deacetyl) linezolid as the active agent. The same can be applied to experezolid, radezolid, ranbezolid and sutezolid. Oxazolidinone antimicrobials remain a mainstay for the treatment of skin infections in adults, tedizolid (TD, FIG. 5) or linezolid (LD, FIG. 5). The introduction of an active antimicrobial or antibiotic compound like TD or LD into a BP molecule can enhance its ability to bind to, concentrate in, and be retained by infected bone—a high bone turnover site often difficult to treat. Some bisphosphonate-oxazolidinone conjugates of the present disclosure are exemplified in FIG. 6.

Figure 7:
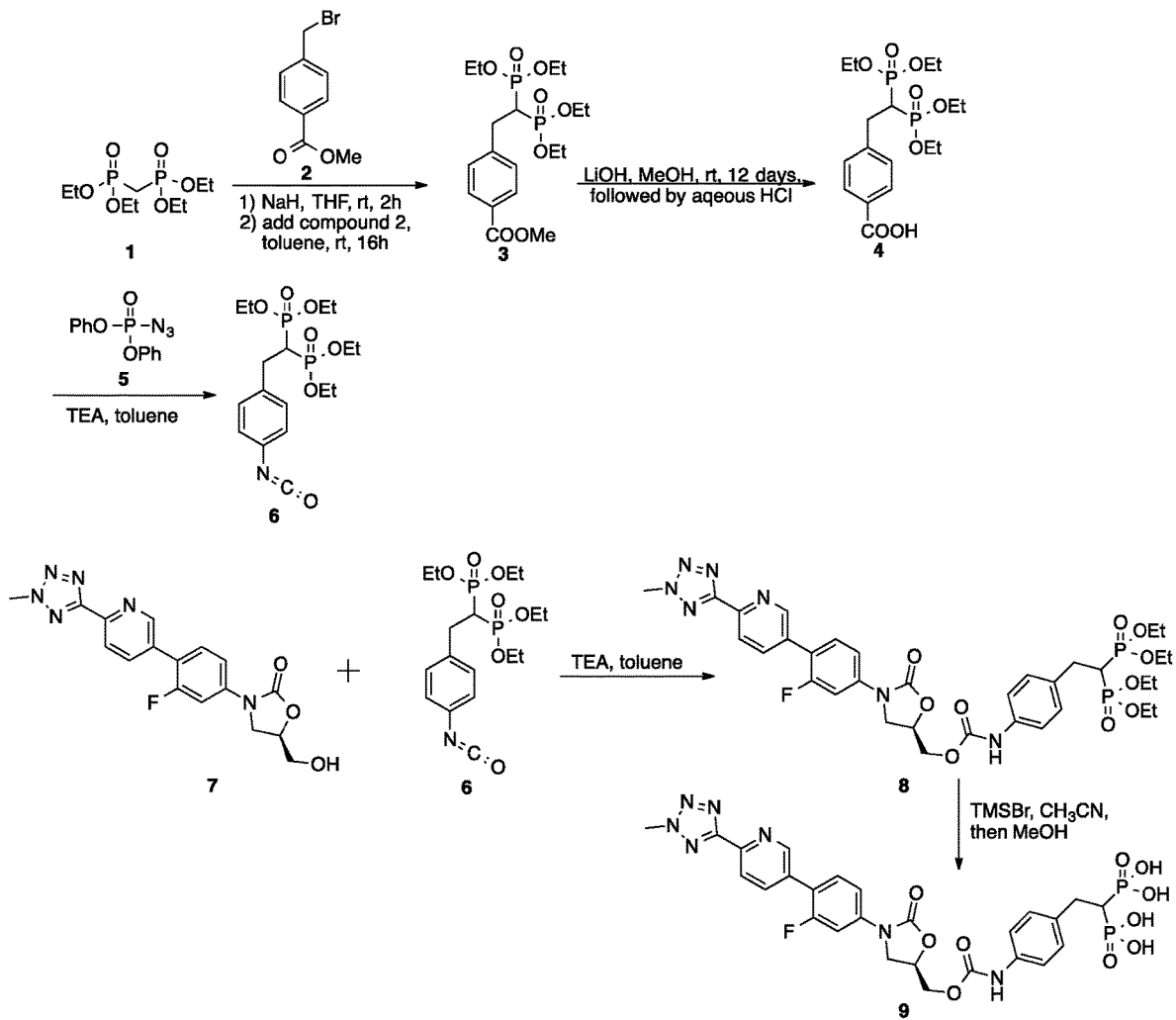
FIG. 7 depicts an exemplary synthesis of a BP-L-TD (L: —OC(O)N—) conjugate.

The synthesis of a BP-linker-tedizolid (BP-L-TD, L: —OC(O)N—) conjugate is exemplified in the synthesis scheme depicted in FIG. 7. The chemistry is also applicable to other oxazolidinones, such as eperezolid, posizolid, et al.

Figure 8:
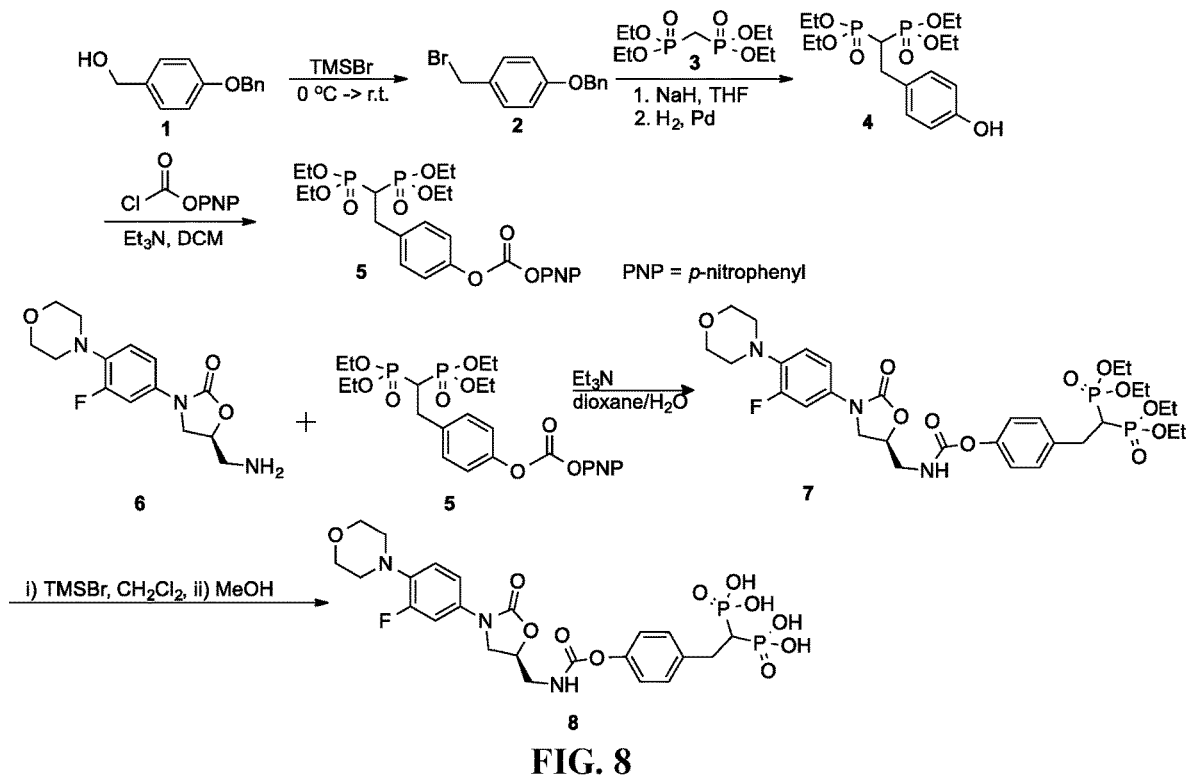
FIG. 8 depicts an exemplary synthesis of a BP-L-dLD (L: —OC(O)N—) conjugate.

The synthesis of a BP-linker-deacetyl-linezolid (BP-L-dLD, L: —OC(O)N—) conjugate is exemplified in the synthesis scheme depicted in FIG. 8. This chemistry is also applicable to other deacetyl-oxazolidinones, such as eperezolid, radezolid, ranbezolid, sutezolid, et al.

Figure 9:
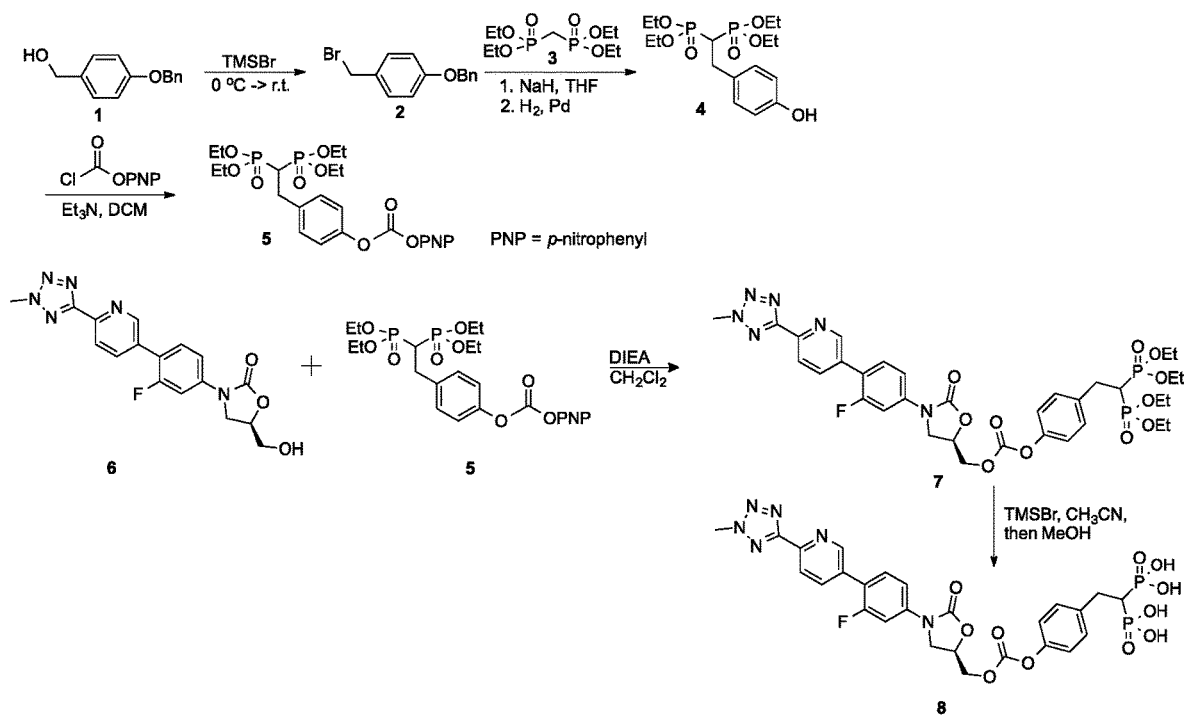
FIG. 9 depicts an exemplary synthesis of a BP-L-TD (L: —OC(O)O—) conjugate.

The synthesis of a BP-linker-tedizolid (BP-L-TD, L: —OC(O)O—) conjugate is exemplified in the synthesis scheme depicted in FIG. 9. This chemistry is also applicable to other oxazolidinones, such as eperezolid, posizolid, et al.

Figure 10:
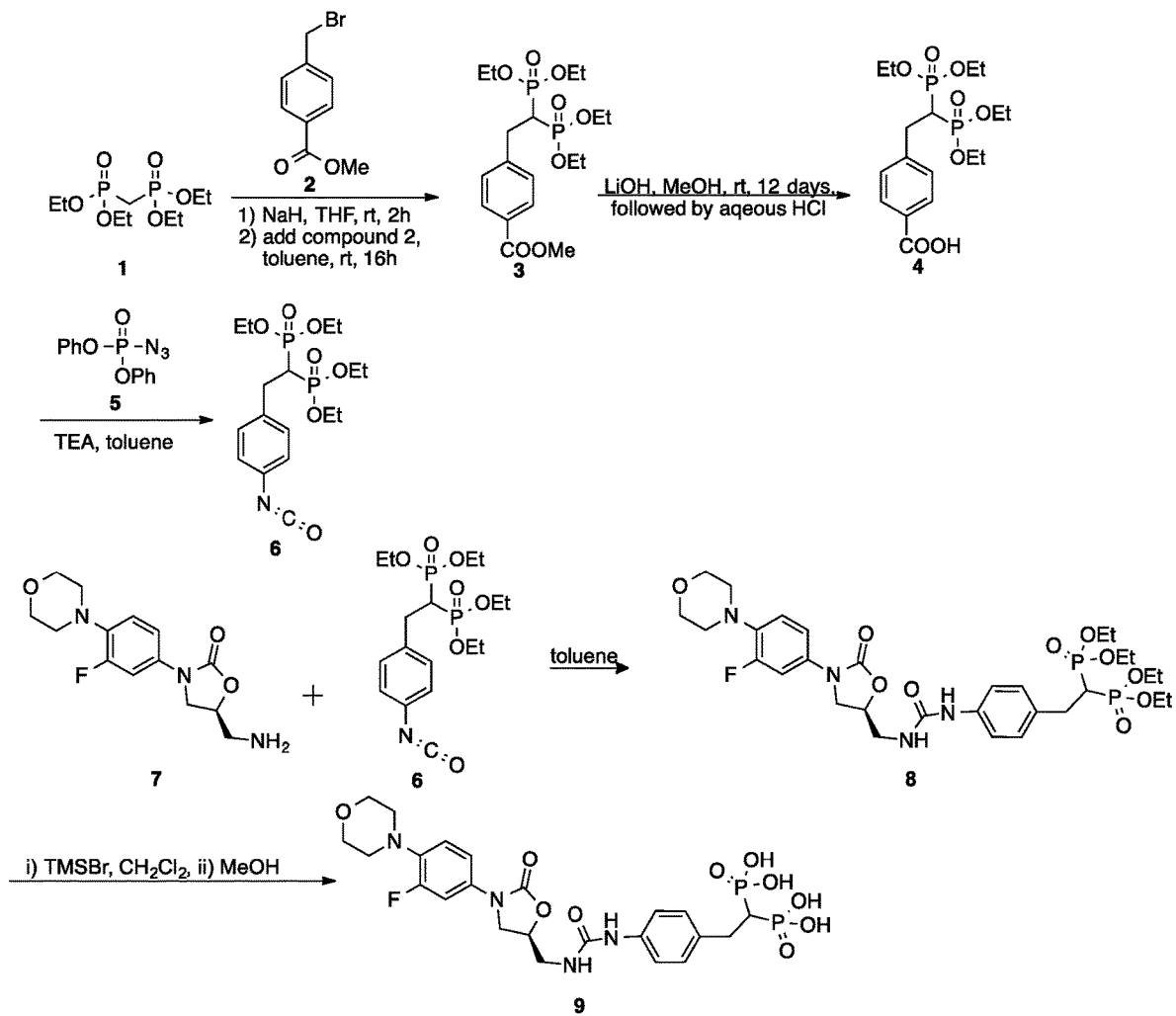
FIG. 10 depicts an exemplary synthesis of a BP-L-dLD (L: —NC(O)N—) conjugate.

The synthesis of a BP-linker-deacetyl-linezolid (BP-L-dLD, L: —NC(O)N—) conjugate is exemplified in the synthesis scheme depicted in FIG. 10. This chemistry is also applicable to other deacetyl-oxazolidinones, such as eperezolid, radezolid, ranbezolid, sutezolid, et al.

As an example, the releasable linker can be a carbamate linkage, an aryl carbamate, a phenyl carbamate linkage, a thiocarbamate, a dithiocarbamate, or a hydrazone linkage. These BP-Ab conjugates are stable in the bloodstream after injection in vivo, but labile at the bone surface to release the antimicrobials at an effective concentration providing detectable antibacterial activity. The rate of release of the antimicrobial agent and amount of drug localized at the surface relative to the amount administered can be tuned by changing the chain length of phenyl alkyl BPs or using different bone affinity BPs.

The detailed syntheses of a BP-linker-tedizolid (BP-L-TD, L: —OC(O)N—) conjugate and (BP-L-TD, L: —C(O)O—) conjugate can be as follows:

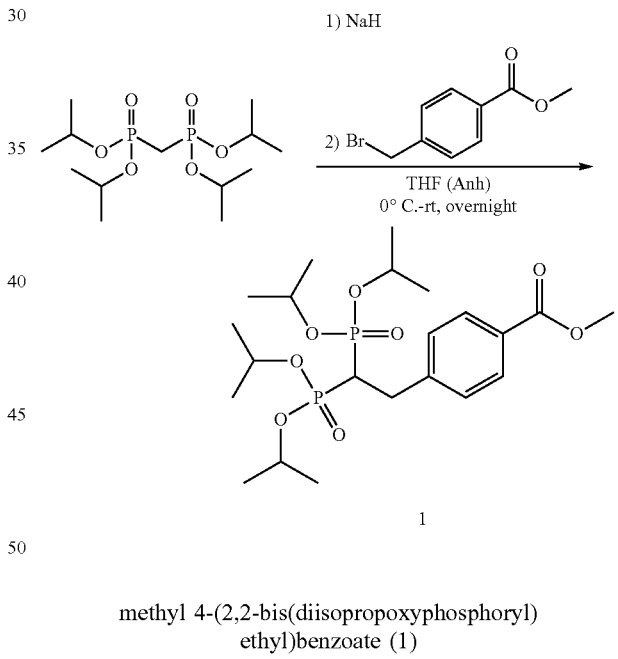

methyl 4-(2,2-bis(diisopropoxyphosphoryl)ethyl)benzoate (1)

Under nitrogen atmosphere, in a 250 mL round bottom flask, THF (35 mL) was added to 60% dispersion of NaH in mineral oil (0.976 g, 24.40 mmol). The suspension was cooled to 0° C., while stirring, and tetraisopropyl methylenediphosphonate (6.480 mL, 20.33 mmol) was added gradually. The reaction was allowed to reach ambient temperature and once hydrogen gas stopped bubbling out of the reaction mixture, the solution was cooled to 0° C. again. Methyl 4(bromomethyl)benzoate (4.660 g, 20.33 mmol) was dissolved in THF (35 mL) and added to the reaction dropwise. The resulting solution was allowed to stir overnight while slowly reaching ambient temperature. Reaction mixture was then cooled to 0° C. and quenched with MeOH (2 mL). NH$_4$Cl$_{(aq)}$ (1 M, 80 mL) was added to the crude and product was extracted with DCM (3×100 mL) combined organics were washed with brine (100 mL), dried on MgSO$_4$, filtered, concentrated under reduced pressure and purified by silica gel column chromatography using a ACN:CHCl$_3$ gradient (0-100%) to afford 1 as clear oil (58% yield).

pH 3. The resulting mixture was extracted with CHCl$_3$ (3×60 mL). Combined organics were dried on MgSO$_4$ and concentrated under reduced pressure to afford a thick faint yellow oil that turned into an off-white solid in the fridge (100% yield).

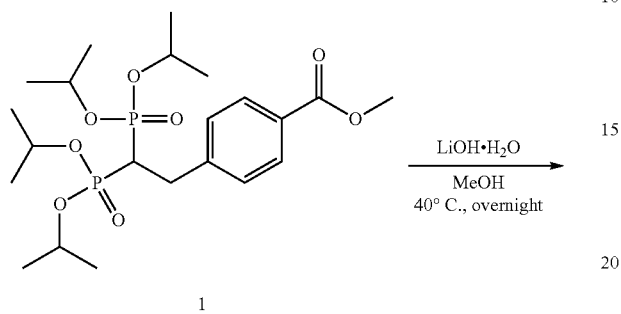

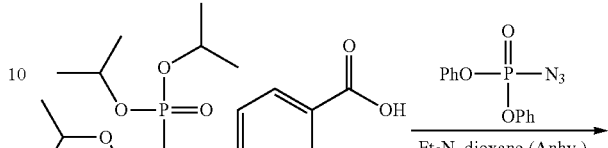

4-(2,2-bis(diisopropoxyphosphoryl)ethyl)benzoic acid (2)

To a solution of 1 (1.968 g, 3.996 mmol) in MeOH (20 mL) in a 100 mL round bottom flask, LiOH.H$_2$O (0.838 g, 19.98 mmol) was added and the resulting solution was stirred at room temperature overnight. The reaction mixture was evaporated to dryness, the residue was dissolved in water (70 mL), and HCl$_{(aq)}$ (1 M) was added slowly to reach tetraisopropyl (2-(4-(azidocarbonyl)phenyl)ethane-1,1-diyl)bis(phosphonate) (3)

Compound 2 (1.913 g, 3.998 mmol) was dissolved in anhydrous dioxane (19 mL). Diphenyl phosphoryl azide (1.100 g, 3.998 mmol), and trimethylamine (0.445 g, 4.400 mmol) were added and the reaction was allowed to stir at room temperature for 2 hours. Ultrapure deionized water (20 ml) was added to the reaction mixture and the product was extracted using hexane (4×40 mL). The hexane extracts were combined, dried over MgSO$_4$, filtered, and concentrated under vacuum to afford 4 which was used without further purification (92% Yield).

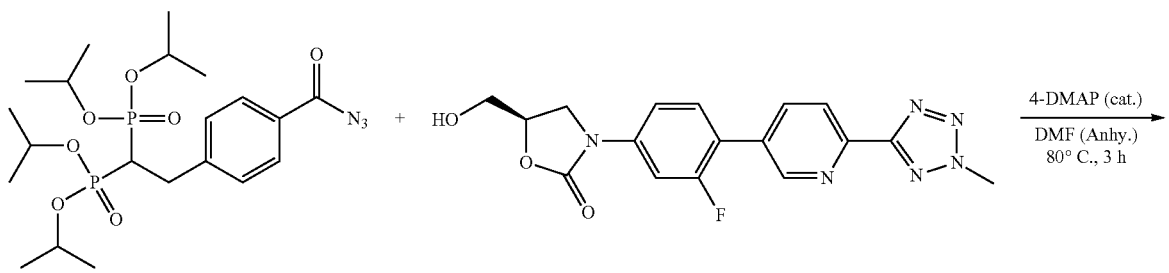

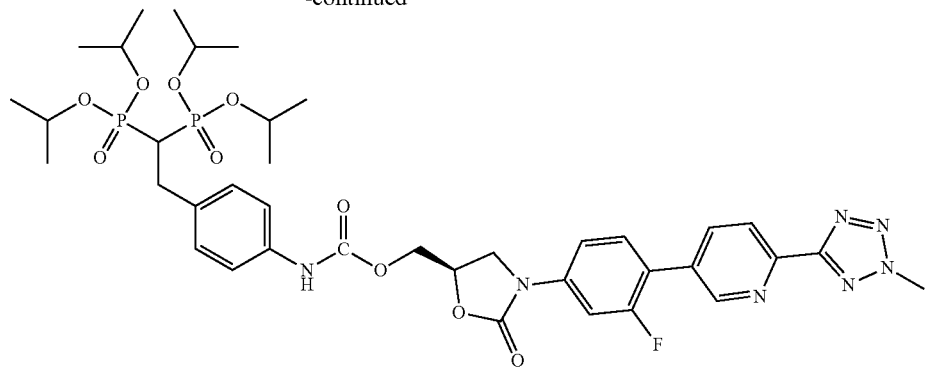

4

In an 8 Dr glass vial flushed with N₂, compound 3 (84.00 mg, 0.167 mmol) and Tedizolid (61.80 mg, 0.167 mmol) were dissolved in anhydrous DMF (1.5 mL) and catalytic amount of DMAP (8.200 mg, 0.067 mmol) was added to the solution. The reaction vial was covered with foil and stirred at 80° C. for 3 hours. Reaction progress was monitored with TLC (1:1 ACN/CHCl₃). Solvent was removed under reduced pressure and purified by silica gel column chromatography using a ACN:CHCl₃ gradient (25-50%) to afford 4 as white foam (81% yield).

(R)-(2-(4-((((3-(3-fluoro-4-(6-(2-methyl-2H-tetrazol-5-yl)pyridin-3-yl)phenyl)-2-oxooxazolidin-5-yl)methoxy)carbonyl)amino)phenyl)ethane-1,1-diyl)bis(phosphonic acid) (5)

In an 8 Dr glass vial, compound 4 (0.104 g, 0.123 mmol) was dissolved in DCM (1.5 mL) and BTMS (324.5 μL, 2.459 mmol) was added. The vial was capped and heated overnight at 35° C. while covered with foil and stirring. The following day, solvent was removed under vacuum and the

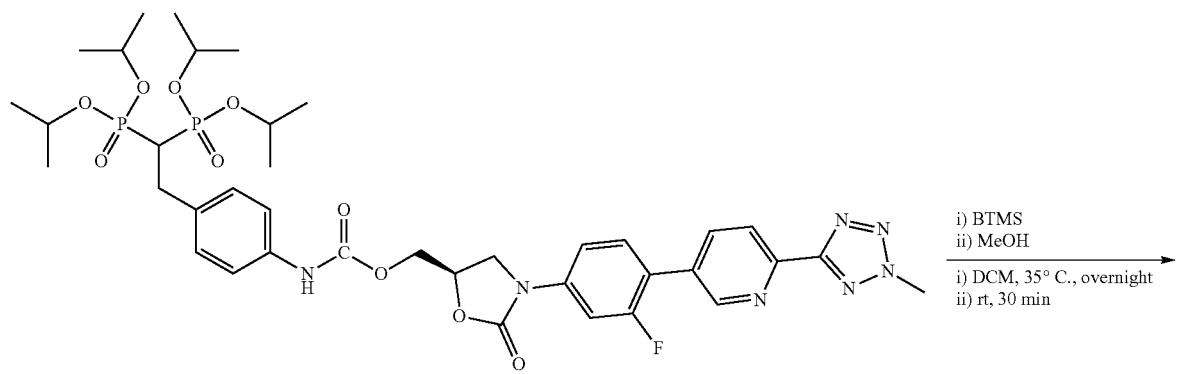

4 i) BTMS
ii) MeOH i) DCM, 35° C., overnight
ii) rt, 30 min

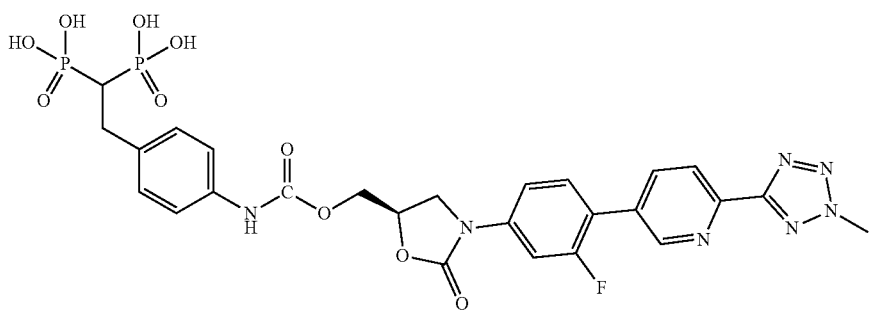

5 crude was quenched with MeOH (3 mL). The resulting solution was stirred at room temperature for 30 minutes. Solvent was removed under reduced pressure and product was precipitated in MeOH and the resulting suspension was filtered using a medium fritted glass funnel. The resulting solid was further washed with MeOH to afford a faint yellow powder (81% yield).

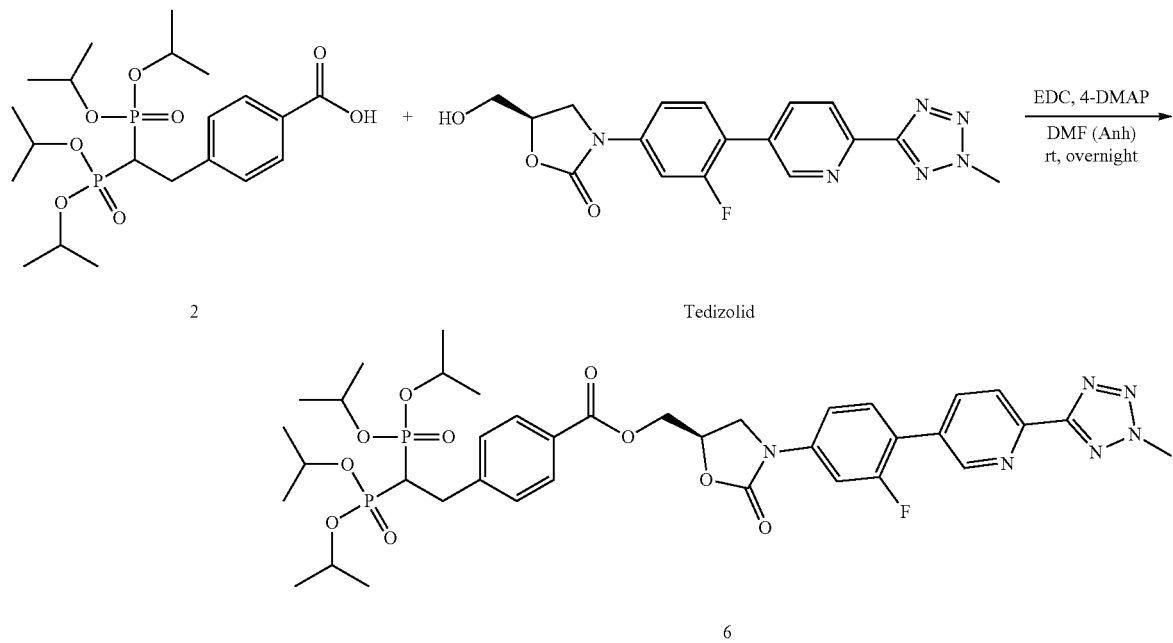

(R)-(3-(3-fluoro-4-(6-(2-methyl-2H-tetrazol-5-yl)pyridin-3-yl)phenyl)-2-oxooxazolidin-5-yl)methyl 4-(2,2-bis(diisopropoxyphosphoryl)ethyl)benzoate (6)

In a 1.5 Dr glass vial flushed with $N_2$, compound 2 (100 mg, 0.209), Tedizolid (77.4 mg, 0.209 mmol), and EDC (64.9 mg, 0.418 mmol) were dissolved in anhydrous DMF (2 mL) and catalytic amount of 4-DMAP (28.1 mg, 0.230 mmol) was added to the solution. The reaction vial was covered with foil and stirred at room temperature overnight. Reaction progress was monitored with TLC (1:1 ACN/CHCl$_3$). Solvent was removed under reduced pressure and purified by silica gel column chromatography using 1:1 CAN/CHCl$_3$ mixture as eluent to afford 6 as faint yellow viscous oil (95% yield).

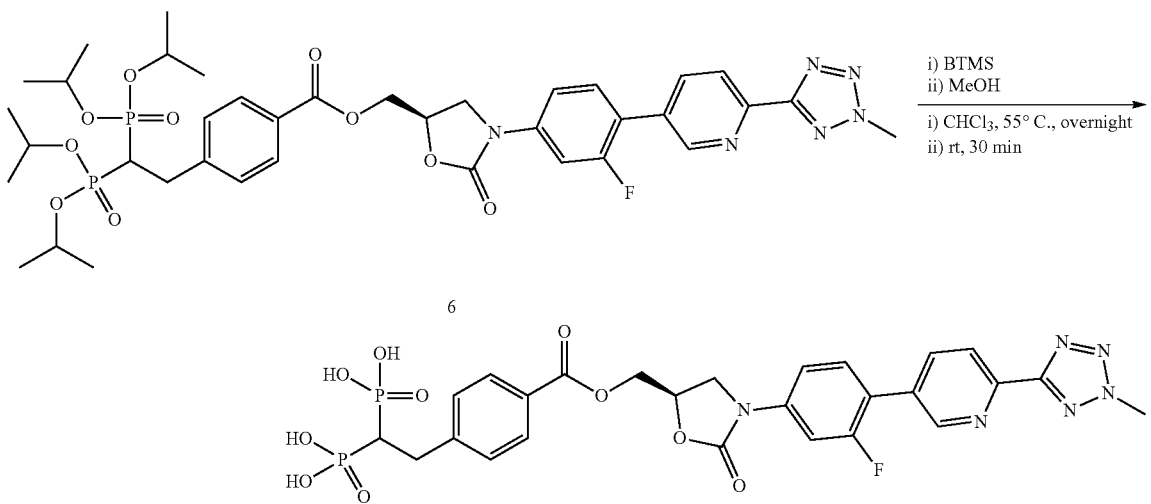

(R)-(2-(4-(((3-(3-fluoro-4-(6-(2-methyl-2H-tetrazol-5-yl)pyridin-3-yl)phenyl)-2-oxooxazolidin-5-yl)methoxy)carbonyl)phenyl)ethane-1,1-diyl)bis(phosphonic acid) (7)

In an 1 Dr glass vial, compound 6 (0.096 g, 0.116 mmol) was dissolved in chloroform (1 mL) and BTMS (610 µL, 4.62 mmol) was added. The vial was capped and heated overnight at 55° C. while covered with foil and stirring. The following day, solvent was removed under vacuum and the crude was quenched with MeOH (2 mL). The resulting solution was stirred at room temperature for 30 minutes. Solvent was removed under reduced pressure and product was precipitated in MeOH and the resulting suspension was filtered using a medium fritted glass funnel. The resulting solid was further washed with MeOH to afford a yellow powder (70% yield).

Figure 11:
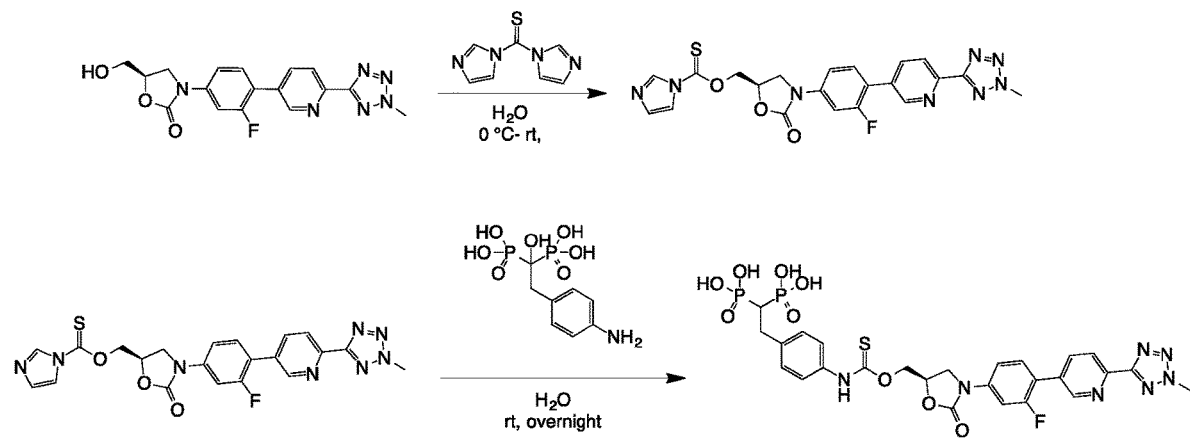
FIG. 11 depicts an exemplary synthesis of a BP-L-TD (L: —OC(S)N—) conjugate.

The synthesis of a BP-linker-tedizolid (BP-L-TD, L: —OC(S)N—) conjugate is exemplified in the synthesis scheme depicted in FIG. 11. This chemistry is also applicable to other oxazolidinones, such as eperezolid, posizolid, et al.

Figure 12:
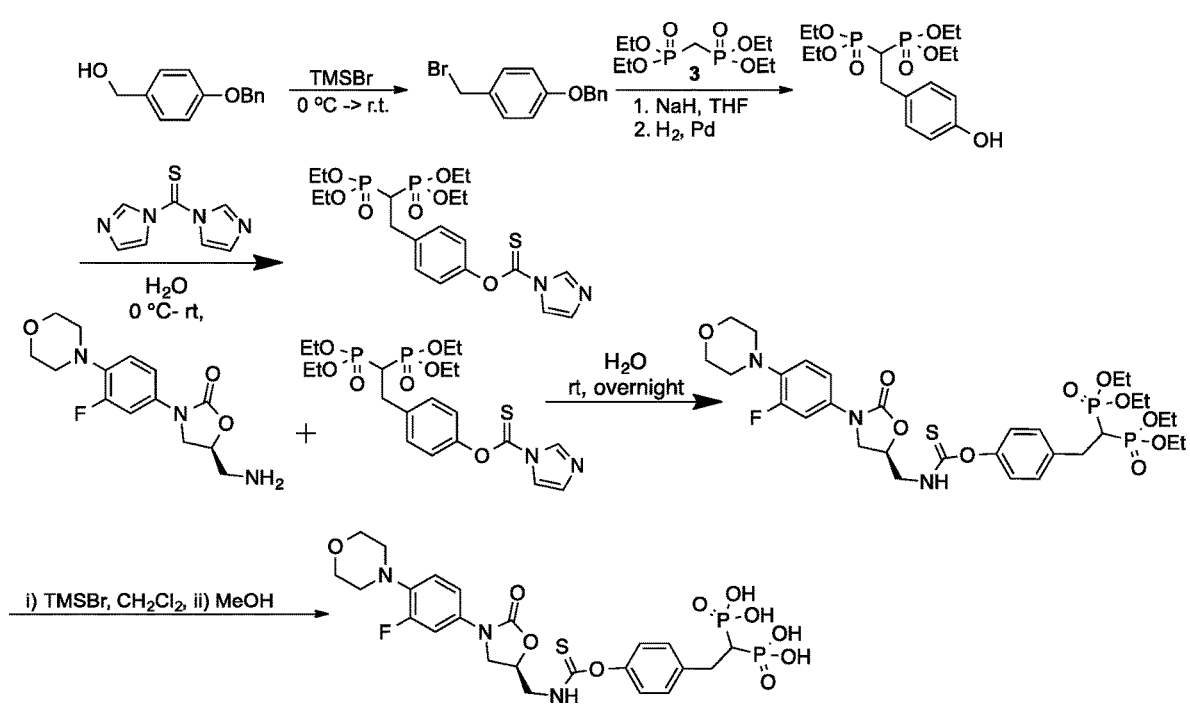
FIG. 12 depicts an exemplary synthesis of a BP-L-dLD (L: —OC(S)N—) conjugate.

The synthesis of a BP-linker-linezolid (BP-L-dLD, L: —OC(S)N—) conjugate is exemplified in the synthesis scheme depicted in FIG. 12. This chemistry is also applicable to other other deacetyl-oxazolidinones, such as eperezolid, radezolid, ranbezolid, sutezolid, et al.

Figure 13:
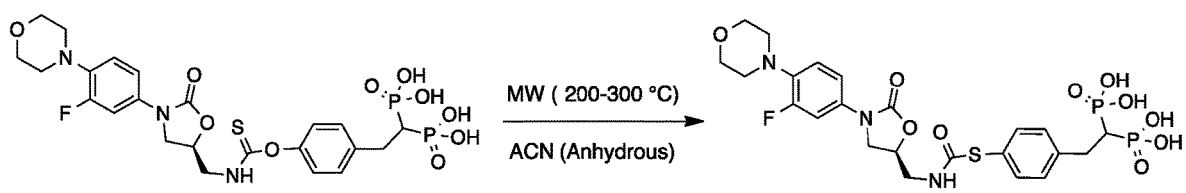
FIG. 13 depicts an exemplary synthesis of a BP-L-dLD (L: —SC(O)N—) conjugate.

The synthesis of a BP-linker-linezolid (BP-L-dLD, L: —SC(O)N—) conjugate is exemplified in the synthesis scheme depicted in FIG. 13. This chemistry is also applicable to other other deacetyl-oxazolidinones, such as eperezolid, radezolid, ranbezolid, sutezolid, et al.

Figure 14:
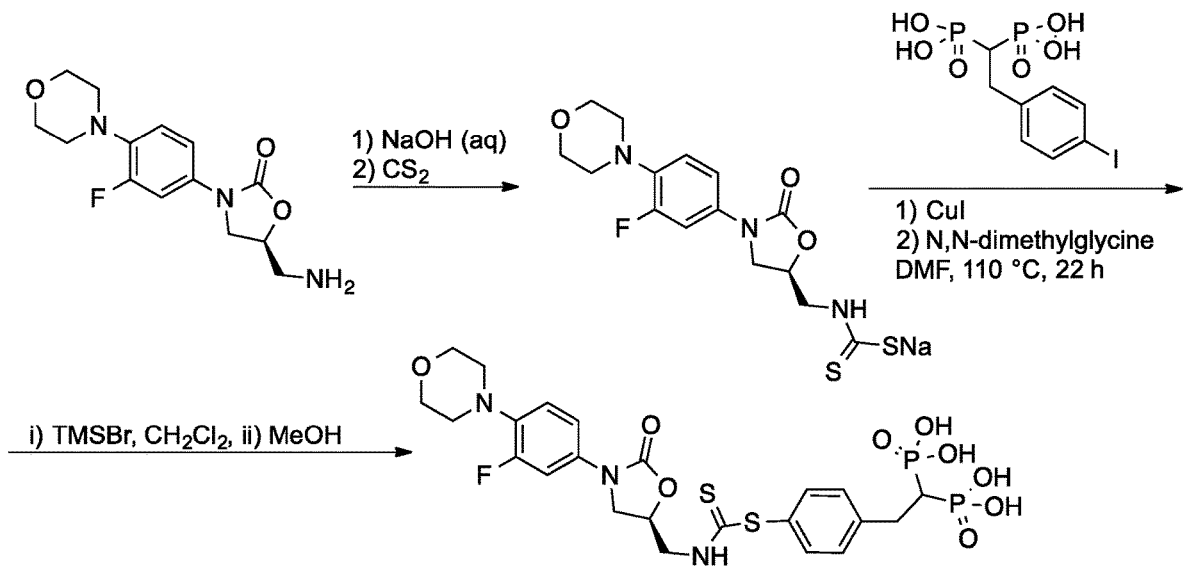
FIG. 14 depicts an exemplary synthesis of a BP-L-dLD (L: —SC(S)N—) conjugate.

The synthesis of a BP-linker-linezolid (BP-L-dLD, L: —SC(S)N—) conjugate is exemplified in the synthesis scheme depicted in FIG. 14. This chemistry is also applicable to other other deacetyl-oxazolidinones, such as eperezolid, radezolid, ranbezolid, sutezolid, et al.

Figure 15:
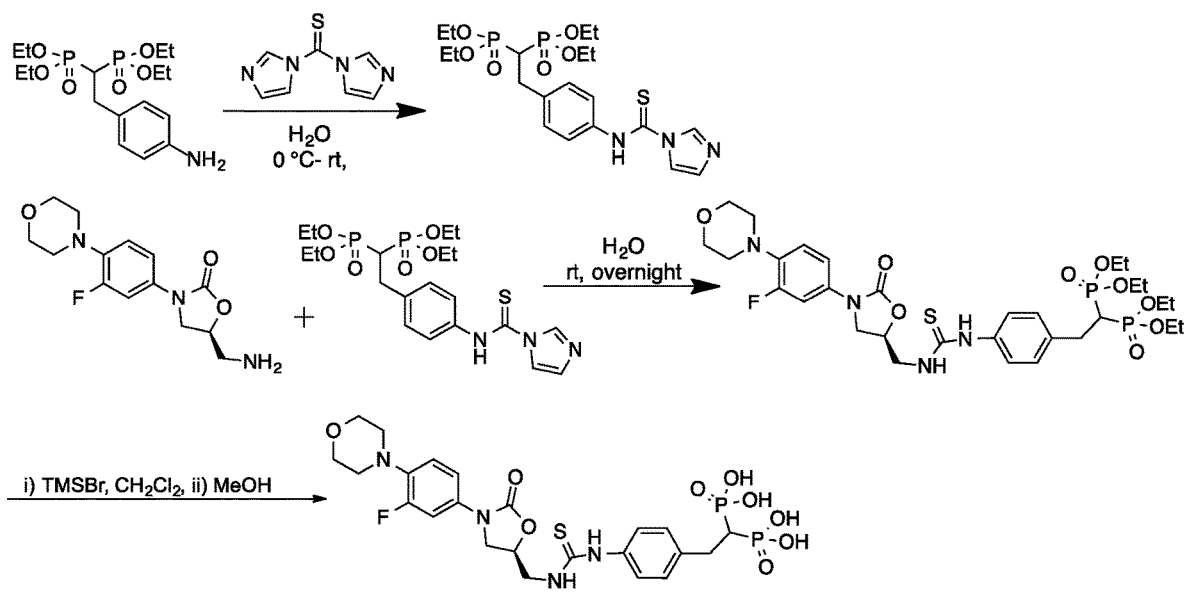
FIG. 15 depicts an exemplary synthesis of a BP-L-dLD (L: —NC(S)N—) conjugate.

The synthesis of a BP-linker-linezolid (BP-L-dLD, L: —NC(S)N—) conjugate is exemplified in the synthesis scheme depicted in FIG. 15. This chemistry is also applicable to other other deacetyl-oxazolidinones, such as eperezolid, radezolid, ranbezolid, sutezolid, et al.

Table 1 below depicts antimicrobial susceptibility results using standards assays for experimental pathogens in polystyrene wells, wherein M—Minocycline; C—Ciprofloxacin; X—Moxifloxacin; T—Tedizolid; V—Vancomycin; BCT—Bisphosphonate-carbamate-tedizolid conjugate (BP-L-TD, L: —NC(O)O—, as exemplified in FIG. 6); BET—Bisphosphonate-ester-tedizolid conjugate ((BP-L-TD, L: —C(O)O—, as exemplified in FIG. 6 cont'd (19)); * spectrum of antimicrobial activity does not cover this specific pathogen and not supported for use against specific bacteria.

Figure 16:
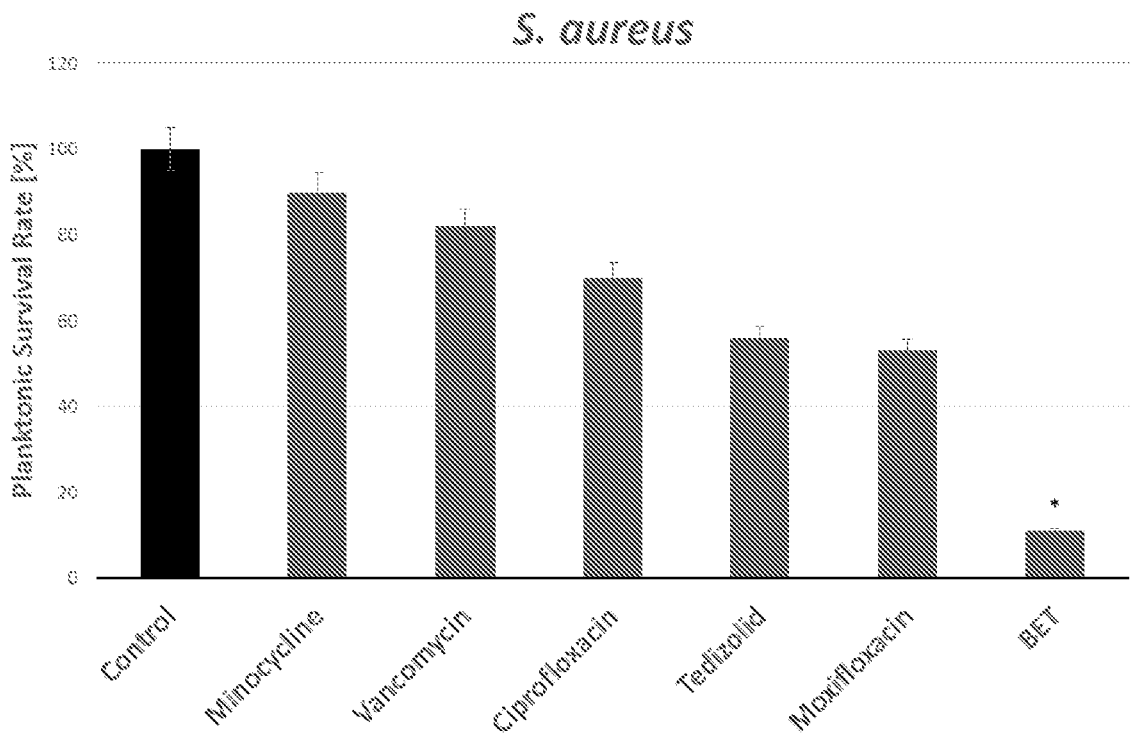
FIG. 16 depicts the results of a preventative hydroxyapatite (HA) experiment with tested compounds against *S. aureus*.

FIG. 16 depicts the results of a preventative hydroxyapatite (HA) experiment with tested compounds against *S. aureus*. The BET conjugate (BP-L-TD, L: —C(O)O—, as exemplified in FIG. 6 cont'd (19)) demonstrated statistically significant efficacy for preventing the growth of staphylococcal cells. (K-W test, * p<0.01; comparator=control). The results were obtained using standard assays.

Figure 17:
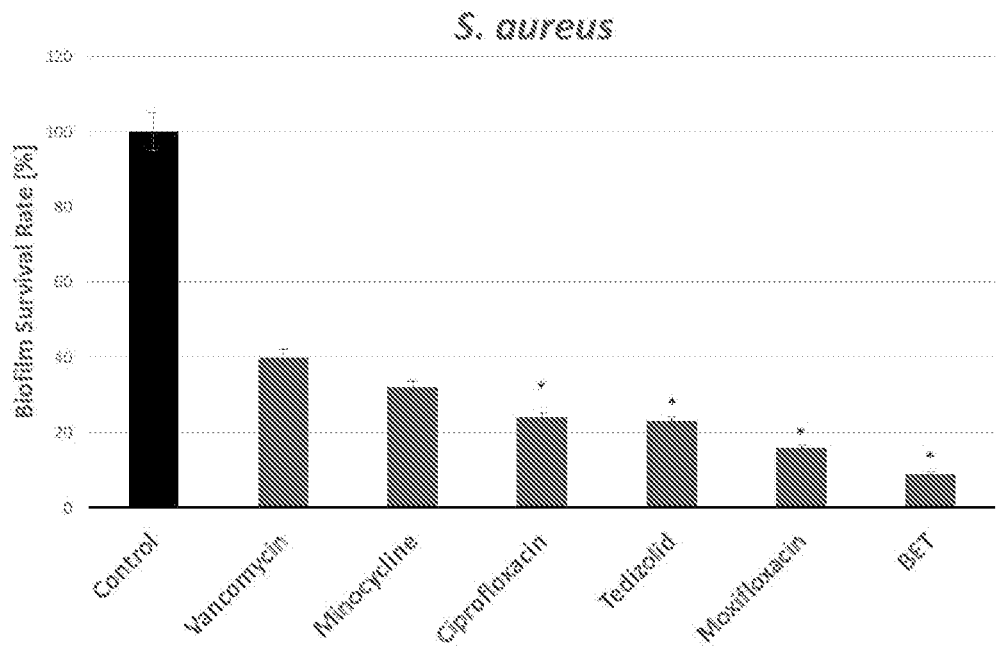
FIG. 17 depicts the results of an eradication experiment with tested compounds against *S. aureus* biofilms on HA.

FIG. 17 depicts the results of an eradication experiment with tested compounds against *S. aureus* biofilms on HA. All tested compounds except vancomycin and minocycline were significantly efficacious in eradicating staphylococcal cells. (K-W test, * p<0.01; comparator=control). BET conjugate is BP-L-TD, L: —C(O)O—, as exemplified in FIG. 7 cont'd (19)). The results were also obtained by using standard assays.

Figure 18B:
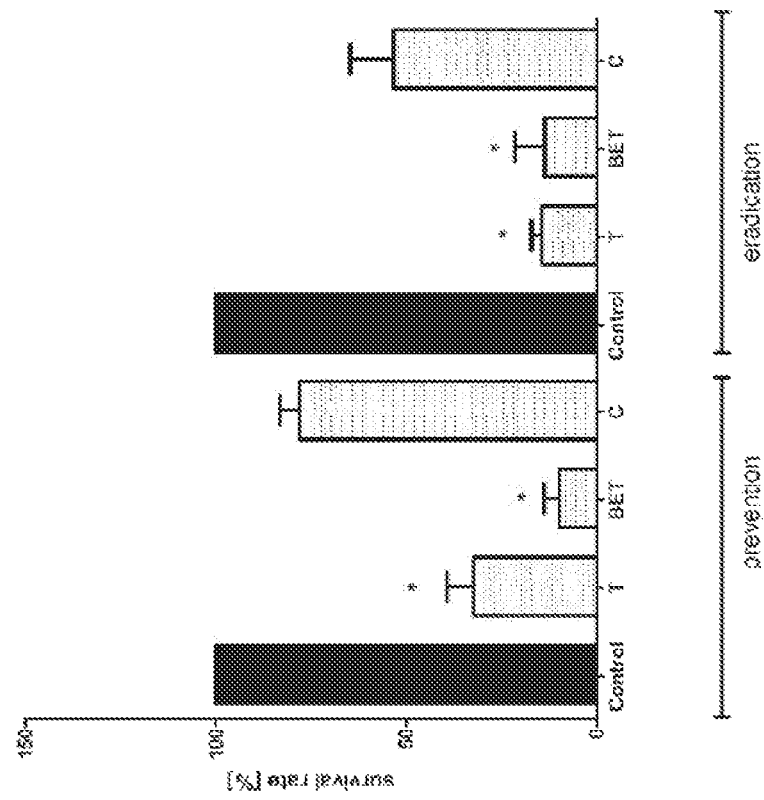
FIG. 18B depicts the results of *S. aureus* biofilm prevention and eradication settings, showing conjugate BET significantly prevented or eradicated biofilm growth on femurs ex vivo, as did tedizolid alone, with greatest efficacy seen with the BET conjugate in both settings (K-W test, * $p<0.01$; comparator=control).
Figure 18A:
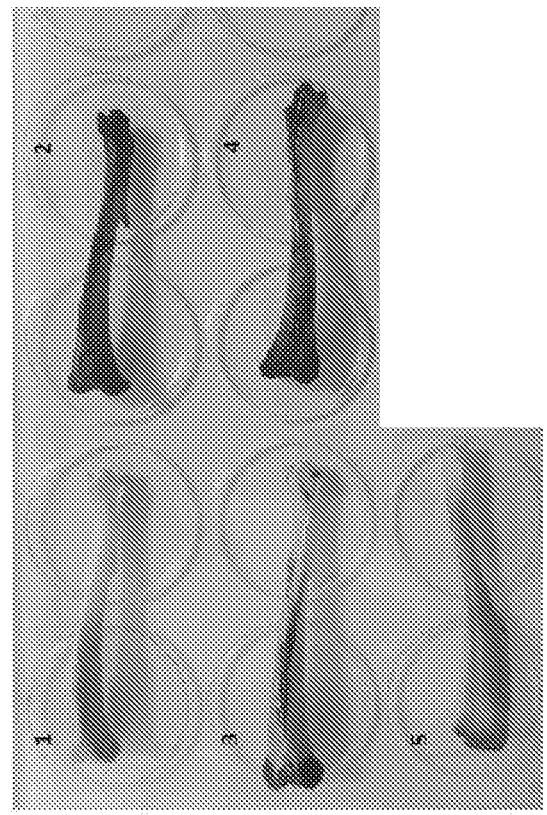
FIG. 18A is a picture of rat femurs saturated with antibiotics or the conjugates after they are introduced to a solution of *S. aureus* in our ex vivo preventative experimental setting. The more the bone appears red, the more staphylococcal biofilms there are adhered to the surface in those regions. Femur 1—negative control sample (no antimicrobial, no *staphylococcus*); 2—positive control sample (no antimicrobial, staphylococcal solution added); 3—bone saturated with tedizolid and introduced to staphylococcal solution; 4—bone saturated with ciprofloxacin and introduced to staphylococcal solution; 5—bone saturated with BET conjugate (BP-L-TD, L: —C(O)O—, as exemplified in FIG. 7 cont'd (19)) and introduced to staphylococcal solution.

FIG. 18A depicts a picture of rat femurs saturated with antibiotics or the conjugates after they are introduced to a solution of *S. aureus* in our ex vivo preventative experimental setting. The more the bone appears red, the more staphylococcal biofilms there are adhered to the surface in those regions. Femur 1—negative control sample (no antimicrobial, no *staphylococcus*); 2—positive control sample (no antimicrobial, staphylococcal solution added); 3—bone saturated with tedizolid and introduced to staphylococcal solution; 4—bone saturated with ciprofloxacin and introduced to staphylococcal solution; 5—bone saturated with BET conjugate (BP-L-TD, L: —C(O)O—, as exemplified in FIG. 7 cont'd (19)) and introduced to staphylococcal solution; FIG. 18B depicts *S. aureus* biofilm prevention and eradication settings, conjugate BET significantly prevented or eradicated biofilm growth on femurs ex vivo, as did tedizolid alone, with greatest efficacy seen with the BET conjugate in both settings (K-W test, * p<0.01; comparator=control).

Ratios, concentrations, amounts, and other numerical data herein may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

TABLE 1

| Microbial pathogens | Antimicrobials [µg/mL] | | | | | | | | | | | | |
|---|---|---|---|---|---|---|---|---|---|---|---|---|---|
| | M | | C | | X | | T | | V | | BCT | | BET | |
| | MIC | MBEC | MIC | MBEC | MIC | MBEC | MIC | MBEC | MIC | MBEC | MIC | MBEC | MIC | MBEC |
| S. aureus | 0.25 | 16 | 0.5 | 32 | 0.05 | 0.5 | 0.5 | 8 | 1 | 8 | 16 | 32 | 4 | 16 |
| Aa | 2 | 8 | 0.5 | 8 | 0.05 | 0.1 | * | * | * | * | * | * | * | * |

We claim:
1. A compound according to Formula (1),

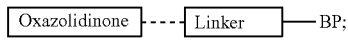 Formula (1)

wherein the Oxazolidinone is an oxazolidinone antimicrobial or antibiotic compound or agent, and the Oxazolidinone includes the structure

to which the Linker is coupled, and
wherein the Linker is a releasable linker that when coupled to the Oxazolidinone and the bisphosphonate (BP) forms a carbamate selected from the group consisting of an aryl carbamate, an O-thioaryl carbamate, an S-thioaryl carbamate, or a phenyl carbamate;
wherein the aryl or phenyl group of the carbamate is coupled to the bisphosphonate (BP); and
wherein the oxazolidinone antimicrobial or antibiotic compound or agent for coupling to the bisphosphonate (BP) by the Linker is selected from the group consisting of: linezolid, tedizolid, eperizolid, posizolid, radezolid, ranbezolid, and sutezolid, antimicrobial or antibiotic compounds and agents.

2. The compound of claim 1, wherein the aryl or phenyl group of the carbamate is coupled to a geminal carbon of the bisphosphonate (BP).

3. The compound of claim 1, wherein the bisphosphonate is selected from the group consisting of: hydroxyl phenyl alkyl or aryl bisphosphonates, hydroxyl aryl alkyl hydroxyl bisphosphonates, amino aryl alkyl bisphosphonates, amino aryl alkyl hydroxyl bisphosphonates, hydroxyl alkyl aryl alkyl bisphosphonates, amino aryl alkyl bisphosphonates, amino aryl alkyl hydroxyl bisphosphonates, etidronate, pamidronate, neridronate, olpadronate, alendronate, ibandronate, risedronate, zoledronate, and minodronate, wherein all the compounds can be optionally further substituted or are unsubstituted.

4. The compound of claim 1, wherein the oxazolidinone antimicrobial or antibiotic derived conjugate compound or agent is 2-oxazolidinone.

5. The compound of claim 1, wherein the oxazolidinone antimicrobial or antibiotic compound or agent prior to being coupled by the Linker to the bisphosphonate (BP) is tedizolid or a substituent or derivative thereof.

6. The compound of claim 1, wherein the bisphosphonate is an inert bisphosphonate.

7. The compound of claim 6, wherein the Linker when coupled to the Oxazolidinone and the bisphosphonate (BP) creates an aryl carbamate.

8. The compound of claim 1, wherein the bisphosphonate is an active bisphosphonate.

9. The compound of claim 8, wherein the bisphosphonate has a geminal hydroxy group and the Linker links to a hydroxy or amino group of the bisphosphonate.

10. The compound of claim 1, wherein the bisphosphonate is either is 4-hydroxyphenylethylidene bisphosphonate, or (1-hydroxy-2-(4-hydroxyphenyl)ethane-1,1-diyl)-bisphosphonate, or 2-(4-aminophenyl)ethylidene-1,1-bisphosphonate or 2-(4-aminophenylethylidene)-1-hydroxy-1,1-bisphosphonate.

11. The compound of claim 1, wherein the bisphosphonate (BP) has a formula of

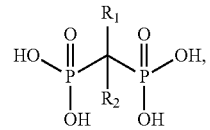

wherein either $R_1$ is H, OH, or Cl, and $R_2$ contains an alkyl (hydroxy phenyl) group, an alkylhydroxyl group, an alkyl phenylamino group, an alkylamino group, an alkyl (hydroxy heterocyclic) group, or an alkyl aminoheterocyclic group, and
the Linker is coupled to the bisphosphonate (BP) $R_2$ group to form the carbamate.

12. The compound of claim 2, wherein the bisphosphonate (BP) has a formula of

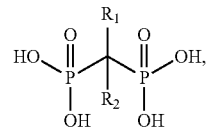

wherein either $R_1$ is H, OH, or Cl, and $R_2$ contains an alkyl (hydroxy phenyl) group, an alkylhydroxyl group, an alkyl phenylamino group, an alkylamino group, an alkyl (hydroxy heterocyclic) group, or an alkyl aminoheterocyclic group, and
the Linker is coupled to the bisphosphonate (BP) $R_2$ group to form the carbamate.

13. The compound of claim 1, wherein the compound consists of any one of the following:
4-aminophenylethylidene bisphosphonate linked via a carbamate to tedizolid (TD) of the general formula (BP-L-TD), wherein BP is 4-aminophenylethylidene bisphosphonate, L is —NC(O)O—, and TD is tedizolid;
4-hydroxyphenylethylidene bisphosphonate linked via a carbonate to tedizolid (TD) of the general formula (BP-L-TD), wherein BP is 4-hydroxyphenylethylidene bisphosphonate, L is —OC(O)O—, and TD is tedizolid;
4-aminophenylethylidene bisphosphonate linked via a carbamate to tedizolid (TD) of the general formula (BP-L-TD), wherein BP is 4-aminophenylethylidene bisphosphonate, L is —NC(S)O—, and TD is tedizolid;
4-hydroxyphenylethylidene bisphosphonate linked via a carbamate to deacetyl-linezolid (dLD) of the general formula (BP-L-dLD), wherein BP is 4-hydroxyphenylethylidene bisphosphonate, L is —OC(O)N—, and dLD is deacetyl-linezolid;
4-hydroxyphenylethylidene bisphosphonate linked via a carbamate to deacetyl-linezolid (dLD) of the general formula (BP-L-dLD), wherein BP is 4-hydroxyphenylethylidene bisphosphonate, L is —OC(S)N— or —SC(O)N— or —SC(S)N—, and dLD is deacetyl-linezolid;
4-aminophenylethylidene bisphosphonate linked via a urea to deacetyl-linezolid (dLD) of the general formula (BP-L-dLD), wherein BP is 4-aminophenylethylidene bisphosphonate, L is —NC(O)N— or —NC(S)N—, and dLD is deacetyl-linezolid;

4-hydroxyphenylethylidene bisphosphonate linked via a carbamate to eperezolid (ED) of the general formula (BP-L-ED), wherein BP is 4-hydroxyphenylethylidene bisphosphonate, L is —NC(O)O—, and ED is eperezolid;

4-hydroxyphenylethylidene bisphosphonate linked via a carbamate to eperezolid (ED) of the general formula (BP-L-ED), wherein BP is 4-hydroxyphenylethylidene bisphosphonate, L is —NC(S)O—, and ED is eperezolid;

4-hydroxyphenylethylidene bisphosphonate linked via a carbonate to eperezolid (ED) of the general formula (BP-L-ED), wherein BP is 4-hydroxyphenylethylidene bisphosphonate, L is —OC(O)O—, and ED is eperezolid;

4-hydroxyphenylethylidene bisphosphonate linked via a carbamate to deacetyl-eperezolid (dED) of the general formula (BP-L-dED), wherein BP is 4-hydroxyphenylethylidene bisphosphonate, L is —OC(O)N—, and dED is deacetyl-eperezolid;

4-hydroxyphenylethylidene bisphosphonate linked via a carbamate to deacetyl-eperezolid (dED) of the general formula (BP-L-dED), wherein BP is 4-hydroxyphenylethylidene bisphosphonate, L is —OC(S)N— or —SC(O)N— or —SC(S)N—, and dED is deacetyl-eperezolid;

4-aminophenylethylidene bisphosphonate linked via a urea to deacetyl-eperezolid (dED) of the general formula (BP-L-dED), wherein BP is 4-aminophenylethylidene bisphosphonate, L is —NC(O)N— or —NC(S)N—, and dED is deacetyl-eperezolid;

4-hydroxyphenylethylidene bisphosphonate linked via a carbamate to deacetyl-sutezolid (dSD) of the general formula (BP-L-dSD), wherein BP is 4-hydroxyphenylethylidene bisphosphonate, L is —OC(O)N—, and dSD is deacetyl-sutezolid;

4-hydroxyphenylethylidene bisphosphonate linked via a carbamate to deacetyl-sutezolid (dSD) of the general formula (BP-L-dSD), wherein BP is 4-hydroxyphenylethylidene bisphosphonate, L is —OC(S)N— or —SC(O)N— or —SC(S)N—, and dSD is deacetyl-sutezolid;

4-aminophenylethylidene bisphosphonate linked via a urea to deacetyl-sutezolid (dSD) of the general formula (BP-L-dSD), wherein BP is 4-aminophenylethylidene bisphosphonate, L is —NC(O)N— or —NC(S)N—, and dSD is deacetyl-sutezolid;

4-aminophenylethylidene bisphosphonate linked via a carbamate to radezolid (RD) of the general formula (BP-L-RD), wherein BP is 4-aminophenylethylidene bisphosphonate, L is —OC(O)N—, and RD is radezolid;

4-aminophenylethylidene bisphosphonate linked via a carbamate to radezolid (RD) of the general formula (BP-L-RD), wherein BP is 4-aminophenylethylidene bisphosphonate, L is —OC(S)N— or —SC(O)N— or —SC(S)N—, and RD is radezolid;

4-aminophenylethylidene bisphosphonate linked via a urea to deacetyl-radezolid (dRD) of the general formula (BP-L-RD), wherein BP is 4-aminophenylethylidene bisphosphonate, L is —NC(O)N— or —NC(S)N—, and RD is radezolid;

4-aminophenylethylidene bisphosphonate linked via a carbamate to deacetyl-radezolid (dRD) of the general formula (BP-L-dRD), wherein BP is 4-aminophenylethylidene bisphosphonate, L is —OC(O)N—, and dRD is deacetyl-radezolid;

4-aminophenylethylidene bisphosphonate linked via a carbamate to deacetyl-radezolid (dRD) of the general formula (BP-L-dRD), wherein BP is 4-aminophenylethylidene bisphosphonate, L is —OC(S)N— or —SC(O)N— or —SC(S)N—, and dRD is deacetyl-radezolid;

4-aminophenylethylidene bisphosphonate linked via a urea to deacetyl-radezolid (dRD) of the general formula (BP-L-dRD), wherein BP is 4-aminophenylethylidene bisphosphonate, L is —NC(O)N— or —NC(S)N—, and dRD is deacetyl-radezolid;

4-hydroxyphenylethylidene bisphosphonate linked via a carbamate to deacetyl-ranbezolid (dRbD) of the general formula (BP-L-dRbD), wherein BP is 4-hydroxyphenylethylidene bisphosphonate, L is —OC(O)N—, and dRbD is deacetyl-ranbezolid;

4-hydroxyphenylethylidene bisphosphonate linked via a carbamate to deacetyl-ranbezolid (dRbD) of the general formula (BP-L-dRbD), wherein BP is 4-hydroxyphenylethylidene bisphosphonate, L is —OC(S)N— or —SC(O)N— or —SC(S)N—, and dRbD is deacetyl-ranbezolid;

4-aminophenylethylidene bisphosphonate linked via a urea to deacetyl-ranbezolid (dRbD) of the general formula (BP-L-dRbD), wherein BP is 4-aminophenylethylidene bisphosphonate, L is —NC(O)N— or —NC(S)N—, and dRbD is deacetyl-ranbezolid;

4-aminophenylethylidene bisphosphonate linked via a carbamate to posizolid (PD) of the general formula (BP-L-PD), wherein BP is 4-aminophenylethylidene bisphosphonate, L is —NC(O)O—, and PD is posizolid;

4-aminophenylethylidene bisphosphonate linked via a carbamate to posizolid (PD) of the general formula (BP-L-PD), wherein BP is 4-aminophenylethylidene bisphosphonate, L is —NC(S)O—, and PD is posizolid; or 4-hydroxyphenylethylidene bisphosphonate linked via a carbonate to posizolid (PD) of the general formula (BP-L-PD), wherein BP is 4-hydroxyphenylethylidene bisphosphonate, L is —OC(O)O—, and PD is posizolid.

14. The compound of claim 1, wherein compound has any one of the following formulas

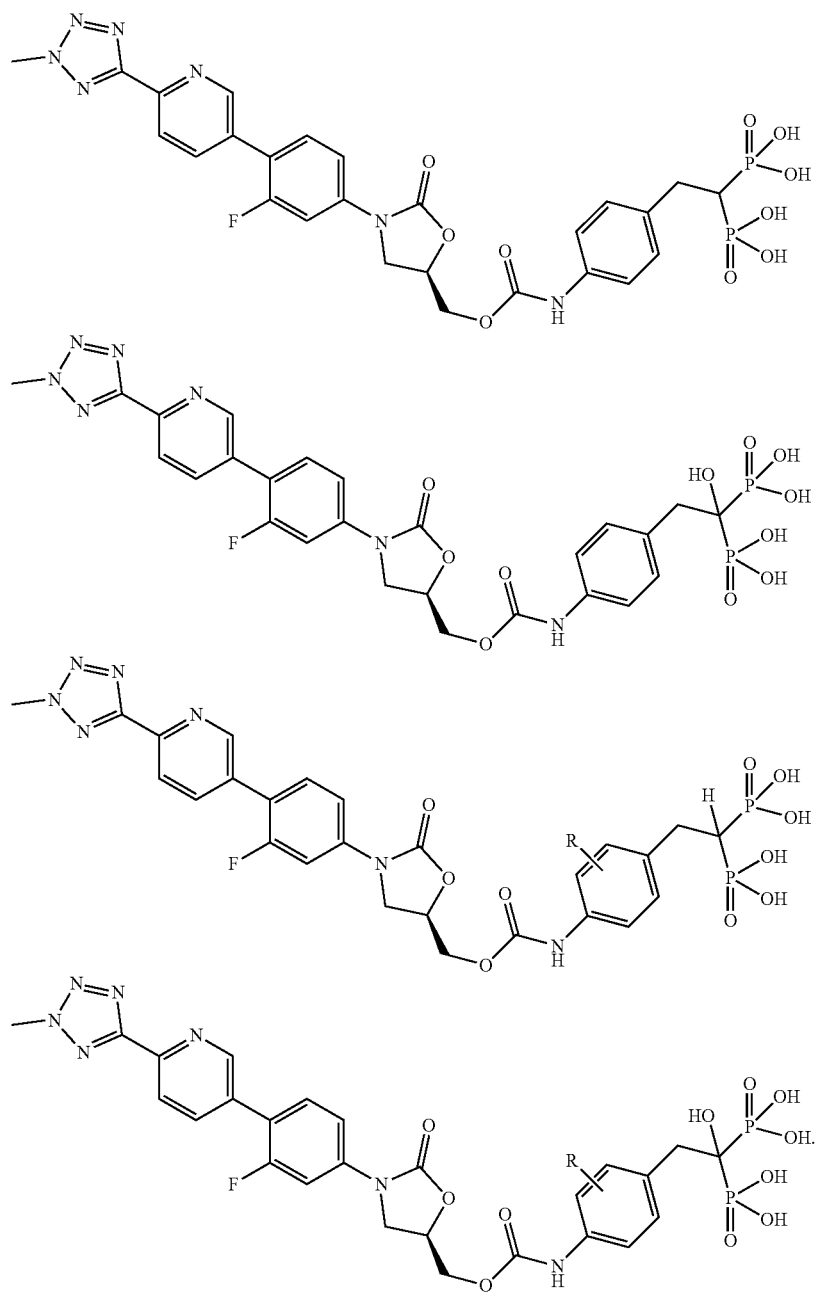

15. A formulation comprising a compound according to claim 1 in the form of an oral rinse solution, a buffered solution for intravenous or parenteral use, or powder/tablet form for enteric administration, or microspheres.

16. The formulation of claim 15, wherein the formulation comprises an effective amount of the compound for the treatment of a bone infectious disease.

17. The formulation of claim 16, wherein the bone infectious disease is selected from the group consisting of osteomyelitis, prosthetic joint infections, osteolytic bone infections, osteonecrosis, diabetic chronic osteomyelitis, diabetic foot, periodontitis and other jaw infections and peripheral infections associated and not associated with bone related infections.

18. A bone graft composition comprising: a bone graft material and a compound according to claim 1, wherein the compound is attached to, integrated with, chemisorbed to, or mixed with the bone graft material.

19. The bone graft composition of claim 18, wherein the bone graft material is autograft bone material, allograft bone material, xenograft bone material, a synthetic bone graft material, or any combination thereof.

20. The composition of claim 18, wherein the compound consists of any one of the following:
  4-aminophenylethylidene bisphosphonate linked via a carbamate to tedizolid (TD) of the general formula (BP-L-TD), wherein BP is 4-aminophenylethylidene bisphosphonate, L is —NC(O)O—, and TD is tedizolid;

4-hydroxyphenylethylidene bisphosphonate linked via a carbonate to tedizolid (TD) of the general formula (BP-L-TD), wherein BP is 4-hydroxyphenylethylidene bisphosphonate, L is —OC(O)O—, and TD is tedizolid;

4-aminophenylethylidene bisphosphonate linked via a carbamate to tedizolid (TD) of the general formula (BP-L-TD), wherein BP is 4-aminophenylethylidene bisphosphonate, L is —NC(S)O—, and TD is tedizolid;

4-hydroxyphenylethylidene bisphosphonate linked via a carbamate to deacetyl-linezolid (dLD) of the general formula (BP-L-dLD), wherein BP is 4-hydroxyphenylethylidene bisphosphonate, L is —OC(O)N—, and dLD is deacetyl-linezolid;

4-hydroxyphenylethylidene bisphosphonate linked via a carbamate to deacetyl-linezolid (dLD) of the general formula (BP-L-dLD), wherein BP is 4-hydroxyphenylethylidene bisphosphonate, L is —OC(S)N— or —SC(O)N— or —SC(S)N—, and dLD is deacetyl-linezolid;

4-aminophenylethylidene bisphosphonate linked via a urea to deacetyl-linezolid (dLD) of the general formula (BP-L-dLD), wherein BP is 4-aminophenylethylidene bisphosphonate, L is —NC(O)N— or —NC(S)N—, and dLD is deacetyl-linezolid;

4-hydroxyphenylethylidene bisphosphonate linked via a carbamate to eperezolid (ED) of the general formula (BP-L-ED), wherein BP is 4-hydroxyphenylethylidene bisphosphonate, L is —NC(O)O—, and ED is eperezolid;

4-hydroxyphenylethylidene bisphosphonate linked via a carbamate to eperezolid (ED) of the general formula (BP-L-ED), wherein BP is 4-hydroxyphenylethylidene bisphosphonate, L is —NC(S)O—, and ED is eperezolid;

4-hydroxyphenylethylidene bisphosphonate linked via a carbonate to eperezolid (ED) of the general formula (BP-L-ED), wherein BP is 4-hydroxyphenylethylidene bisphosphonate, L is —OC(O)O—, and ED is eperezolid;

4-hydroxyphenylethylidene bisphosphonate linked via a carbamate to deacetyl-eperezolid (dED) of the general formula (BP-L-dED), wherein BP is 4-hydroxyphenylethylidene bisphosphonate, L is —OC(O)N—, and dED is deacetyl-eperezolid;

4-hydroxyphenylethylidene bisphosphonate linked via a carbamate to deacetyl-eperezolid (dED) of the general formula (BP-L-dED), wherein BP is 4-hydroxyphenylethylidene bisphosphonate, L is —OC(S)N— or —SC(O)N— or —SC(S)N—, and dED is deacetyl-eperezolid;

4-aminophenylethylidene bisphosphonate linked via a urea to deacetyl-eperezolid (dED) of the general formula (BP-L-dED), wherein BP is 4-aminophenylethylidene bisphosphonate, L is —NC(O)N— or —NC(S)N—, and dED is deacetyl-eperezolid;

4-hydroxyphenylethylidene bisphosphonate linked via a carbamate to deacetyl-sutezolid (dSD) of the general formula (BP-L-dSD), wherein BP is 4-hydroxyphenylethylidene bisphosphonate, L is —OC(O)N—, and dSD is deacetyl-sutezolid;

4-hydroxyphenylethylidene bisphosphonate linked via a carbamate to deacetyl-sutezolid (dSD) of the general formula (BP-L-dSD), wherein BP is 4-hydroxyphenylethylidene bisphosphonate, L is —OC(S)N— or —SC(O)N— or —SC(S)N—, and dSD is deacetyl-sutezolid;

4-aminophenylethylidene bisphosphonate linked via a urea to deacetyl-sutezolid (dSD) of the general formula (BP-L-dSD), wherein BP is 4-aminophenylethylidene bisphosphonate, L is —NC(O)N— or —NC(S)N—, and dSD is deacetyl-sutezolid;

4-aminophenylethylidene bisphosphonate linked via a carbamate to radezolid (dRD) of the general formula (BP-L-RD), wherein BP is 4-aminophenylethylidene bisphosphonate, L is —OC(O)N—, and RD is radezolid;

4-aminophenylethylidene bisphosphonate linked via a carbamate to radezolid (dRD) of the general formula (BP-L-RD), wherein BP is 4-aminophenylethylidene bisphosphonate, L is —OC(S)N— or —SC(O)N— or —SC(S)N—, and RD is radezolid;

4-aminophenylethylidene bisphosphonate linked via a urea to deacetyl-radezolid (dRD) of the general formula (BP-L-RD), wherein BP is 4-aminophenylethylidene bisphosphonate, L is —NC(O)N— or —NC(S)N—, and RD is radezolid;

4-aminophenylethylidene bisphosphonate linked via a carbamate to deacetyl-radezolid (dRD) of the general formula (BP-L-dRD), wherein BP is 4-aminophenylethylidene bisphosphonate, L is —OC(O)N—, and dRD is deacetyl-radezolid;

4-aminophenylethylidene bisphosphonate linked via a carbamate to deacetyl-radezolid (dRD) of the general formula (BP-L-dRD), wherein BP is 4-aminophenylethylidene bisphosphonate, L is —OC(S)N— or —SC(O)N— or —SC(S)N—, and dRD is deacetyl-radezolid;

4-aminophenylethylidene bisphosphonate linked via a urea to deacetyl-radezolid (dRD) of the general formula (BP-L-dRD), wherein BP is 4-aminophenylethylidene bisphosphonate, L is —NC(O)N— or —NC(S)N—, and dRD is deacetyl-radezolid;

4-hydroxyphenylethylidene bisphosphonate linked via a carbamate to deacetyl-ranbezolid (dRbD) of the general formula (BP-L-dRbD), wherein BP is 4-hydroxyphenylethylidene bisphosphonate, L is —OC(O)N—, and dRbD is deacetyl-ranbezolid;

4-hydroxyphenylethylidene bisphosphonate linked via a carbamate to deacetyl-ranbezolid (dRbD) of the general formula (BP-L-dRbD), wherein BP is 4-hydroxyphenylethylidene bisphosphonate, L is —OC(S)N— or —SC(O)N— or —SC(S)N—, and dRbD is deacetyl-ranbezolid;

4-aminophenylethylidene bisphosphonate linked via a urea to deacetyl-ranbezolid (dRbD) of the general formula (BP-L-dRbD), wherein BP is 4-aminophenylethylidene bisphosphonate, L is —NC(O)N— or —NC(S)N—, and dRbD is deacetyl-ranbezolid;

4-aminophenylethylidene bisphosphonate linked via a carbamate to posizolid (PD) of the general formula (BP-L-PD), wherein BP is 4-aminophenylethylidene bisphosphonate, L is —NC(O)O—, and PD is posizolid;

4-aminophenylethylidene bisphosphonate linked via a carbamate to posizolid (PD) of the general formula (BP-L-PD), wherein BP is 4-aminophenylethylidene bisphosphonate, L is —NC(S)O—, and PD is posizolid; or 4-hydroxyphenylethylidene bisphosphonate linked via a carbonate to posizolid (PD) of the general formula (BP-L-PD), wherein BP is 4-hydroxyphenylethylidene bisphosphonate, L is —OC(O)O—, and PD is posizolid.

21. A method of treating or preventing a bone infectous disease at an osseous site or at an implant surgical site, comprising: applying the bone graft composition of claim 18 to the osseous site or at an implant surgical site.

\* \* \* \* \*